US008007797B2

(12) United States Patent
Dietrich et al.

(10) Patent No.: US 8,007,797 B2
(45) Date of Patent: Aug. 30, 2011

(54) JUNCTIONAL ADHESION MOLECULE-C (JAM-C) BINDING COMPOUNDS AND METHODS OF THEIR USE

(75) Inventors: Pierre-Yves Dietrich, St Julien en Genevois (FR); Mirna Tenan, Geneva (CH); Michel Aurrand-Lions, Marseilles (FR); Beat Albert Imhof, Conches (CH)

(73) Assignee: Merck Serono S.A., Coinsins, Vaud (CH)

(*) Notice: Subject to any disclaimer, the term of this patent is extended or adjusted under 35 U.S.C. 154(b) by 233 days.

(21) Appl. No.: 12/443,231

(22) PCT Filed: Sep. 28, 2007

(86) PCT No.: PCT/IB2007/002861
§ 371 (c)(1),
(2), (4) Date: Mar. 27, 2009

(87) PCT Pub. No.: WO2008/038127
PCT Pub. Date: Apr. 3, 2008

(65) Prior Publication Data
US 2010/0034737 A1    Feb. 11, 2010

Related U.S. Application Data

(60) Provisional application No. 60/827,389, filed on Sep. 28, 2006.

(51) Int. Cl.
*A61K 39/395* (2006.01)

(52) U.S. Cl. ............ 424/138.1; 424/141.1; 424/155.1; 424/174.1; 424/182.1; 424/1.49

(58) Field of Classification Search .................. None
See application file for complete search history.

(56) References Cited

U.S. PATENT DOCUMENTS

| | | | |
|---|---|---|---|
| 5,545,806 A | 8/1996 | Lonberg et al. |
| 5,545,807 A | 8/1996 | Surani et al. |
| 5,569,825 A | 10/1996 | Lonberg et al. |
| 5,624,659 A | 4/1997 | Bigner et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,712,120 A | 1/1998 | Rodriguez et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 6,399,763 B1 | 6/2002 | Frenken et al. |
| 6,469,155 B1 | 10/2002 | Fiume et al. |
| 6,635,468 B2 | 10/2003 | Ashkenazi et al. |
| 6,930,172 B2 | 8/2005 | Ferrara et al. |
| 7,393,651 B2 | 7/2008 | Imhof et al. |
| 7,642,341 B2 | 1/2010 | Imhof et al. |
| 7,670,826 B2 | 3/2010 | Imhof et al. |
| 7,790,863 B2 | 9/2010 | Imhof et al. |
| 2003/0017534 A1 | 1/2003 | Buelow et al. |
| 2003/0073149 A1 | 4/2003 | Archer et al. |
| 2004/0208873 A1 | 10/2004 | Teeling et al. |
| 2005/0136060 A1 | 6/2005 | Imhof et al. |
| 2005/0266426 A1 | 12/2005 | Imhof et al. |
| 2007/0202110 A1 | 8/2007 | Imhof et al. |
| 2010/0267649 A1 | 10/2010 | Imhof et al. |
| 2010/0279307 A1 | 11/2010 | Imhof et al. |

FOREIGN PATENT DOCUMENTS

| | | |
|---|---|---|
| EP | 0843961 | 5/1996 |
| EP | 1533617 A1 | 5/2005 |
| WO | WO 92/03918 | 3/1992 |
| WO | WO 92/22645 | 12/1992 |
| WO | WO 93/01227 | 1/1993 |
| WO | WO 94/25585 | 11/1994 |
| WO | WO 95/35374 A1 | 12/1995 |
| WO | WO 97/07671 | 3/1997 |
| WO | WO 98/24897 A1 | 6/1998 |
| WO | WO 98/42739 A2 | 10/1998 |
| WO | WO 99/06551 A2 | 2/1999 |
| WO | WO 98/24884 | 6/1999 |
| WO | WO 99/45962 | 9/1999 |
| WO | WO 00/36102 A2 | 6/2000 |
| WO | WO 00/53749 A2 | 9/2000 |
| WO | WO 01/14404 A1 | 3/2001 |
| WO | WO 01/14424 | 3/2001 |
| WO | WO 02/43478 | 6/2002 |
| WO | WO 03/006673 A2 | 1/2003 |
| WO | WO 03/008541 A2 | 1/2003 |
| WO | WO 03/059282 | 7/2003 |
| WO | WO 2004/055056 | 7/2004 |
| WO | WO 2005/050213 | 6/2005 |
| WO | WO 2006/084078 A2 | 8/2006 |

OTHER PUBLICATIONS

Allgayer, H. et al., "Activation of Src Kinase in Primary Colorectal Carcinoma", *Cancer*, Jan. 15, 2002, pp. 344-351, vol. 94, No. 2.
Arrate, M.P. et al., "Cloning of Human Junctional Adhesion Molecule 3 (JAM3) and its Identification as the JAM2 Counter-receptor", *The Journal of Biological Chemistry*, Dec. 7, 2001, pp. 45826-45832, vol. 276, No. 49.
Aurrand-Lions, M. et al., "JAM-2, a Novel Immunoglobulin Superfamily Molecule, Expressed by Endothelial and Lymphatic Cells", *The Journal of Biological Chemistry*, Jan. 26, 2001, pp. 2733-2741, vol. 276, No. 4.
Aurrand-Lions, M. et al., "Heterogeneity of endothelial junctions is reflected by differential expression and specific subcellular localization of the three JAM family members", *Blood*, Dec. 15, 2001, pp. 3699-3707, vol. 98, No. 13.
Ausman, J.I. et al., "Studies on the Chemotherapy of Experimental Brain Tumors: Development of an Experimental Model", *Cancer Research*, Sep. 1970, pp. 2394-2400, vol. 30.
Bendell, J.C. et al. "Central Nervous System Metastases in Women who Receive Trastuzumab-Based Therapy for Metastatic Breast Carcinoma", *Cancer*, Jun. 15, 2003, pp. 2972-2977, vol. 97, No. 12.
Binz, H.K. et al., "High-affinity binders selected from designed ankyrin repeat protein libraries", *Nature Biotechnology*, May 2004, pp. 575-582, vol. 22, No. 5, Nature Publishing Group.

(Continued)

*Primary Examiner* — Sheela J Huff
(74) *Attorney, Agent, or Firm* — Saliwanchik, Lloyd & Eisenschenk

(57) ABSTRACT

The present invention relates to the use of a compound that specifically binds to JAM-C or JAM-B for the treatment of gliomas. More specifically the invention relates to the use of an antagonist of JAM-B or JAM-C for the treatment of glioma, in particular astrocytoma.

17 Claims, 27 Drawing Sheets

OTHER PUBLICATIONS

Bitonti, A.J. et al., "Pulmonary administration of therapeutic proteins using an immunoglobulin transport pathway", *Advanced Drug Delivery Reviews*, 2006, pp. 1106-1118, vol. 58, Elsevier B.V.

Bitonti, A.J. et al., "Pulmonary delivery of an erythropoietin Fc fusion protein in non-human primates through an immunoglobulin transport pathway", *Proc. Natl. Acad. Sci. USA*, Jun. 29, 2004, pp. 9763-9768, vol. 101, No. 26.

Chavakis, T. et al., "The Junctional Adhesion Molecule-C Promotes Neutrophil Transendothelial Migration in Vitro and in Vivo", *The Journal of Biological Chemistry*, Dec. 31, 2004, pp. 55602-55608, vol. 279, No. 53.

Cunningham, S.A. et al., "A Novel Protein with Homology to the Junctional Adhesion Molecule", *The Journal of Biological Chemistry*, Nov. 3, 2000, pp. 34750-34756, vol. 275, No. 44.

Dall'Acqua, W.F. et al., "Antibody humanization by framework shuffling", *Methods*, 2005, pp. 43-60, vol. 36, Elsevier Inc.

Dall'Acqua, W.F. et al., "Increasing the Affinity of a Human IgG1 for the Neonatal Fc Receptor: Biological Consequences", *The Journal of Immunology*, 2002, pp. 5171-5180, vol. 169.

Damschroder, M.M. et al., "Framework shuffling of antibodies to reduce immunogenicity and manipulate functional and biophysical properties", *Molecular Immunology*, 2007, pp. 3049-3060, vol. 44, Elsevier Ltd.

Datta-Mannan, A. et al., "Humanized IgG$_1$ Variants with Differential Binding Properties to the Neonatal Fc Receptor: Relationship to Pharmacokinetics in Mice and Primates", *Drug Metabolism and Disposition*, 2007, pp. 86-94, vol. 35, No. 1.

Datta-Mannan, A. et al., "Monoclonal Antibody Clearance: Impact of Modulating the Interaction of IgG with the Neonatal Fc Receptor", *The Journal of Biological Chemistry*, Jan. 19, 2007, pp. 1709-1717, vol. 282, No. 3.

Dufner, P. et al., "Harnessing phage and ribosome display for antibody optimisation", *TRENDS in Biotechnology*, 2006, pp. 523-529, vol. 24, No. 11, Elsevier Ltd.

Dumont, J.A. et al., "Delivery of an Erythropoietin-Fc Fusion Protein by Inhalation in Humans through an Immunoglobulin Transport Pathway", *Journal of Aerosol Medicine*, 2005, pp. 294-303, vol. 18, No. 3.

Edelman, G.M. et al., "The Covalent Structure of an Entire γG Immunoglobulin Molecule", *Biochemistry*, 1969, pp. 78-85, vol. 63.

Gerber, D.E. et al., "Emerging monoclonal antibody therapies for malignant gliomas", *Expert Opin. Investig. Drugs*, 2007, pp. 477-494, vol. 16, No. 4, Informa UK Ltd.

Ghetie, V. et al., "Increasing the serum persistence of an IgG fragment by random mutagenesis", *Nature Biotechnology*, Jul. 1997, pp. 637-640, vol. 15, Nature Publishing Group.

Gill, D.S et al., "Biopharmaceutical drug discovery using novel protein scaffolds", *Current Opinion in Biotechnology*, 2006, pp. 653-658, vol. 17, Elsevier Ltd.

Gonzales, N. R. et al., "SDR grafting of a murine antibody using multiple human germline templates to minimize its immunogenicity", *Molecular Immunology*, 2004, pp. 863-872, vol. 41, Elsevier Ltd.

Green, L.L., "Antibody engineering via genetic engineering of the mouse: XenoMouse strains are a vehicle for the facile generation of therapeutic human monoclonal antibodies", *Journal of Immunological Methods*, 1999, pp. 11-23, vol. 231, Elsevier Science B.V.

Groves, M.A.T. et al., "Applications of ribosome display to antibody drug discovery", *Expert Opin. Biol. Ther.*, 2005, pp. 125-135, vol. 5, No. 1, Ashley Publications.

Hinton, P.R. et al., "Engineered Human IgG Antibodies with Longer Serum Half-lives in Primates", *The Journal of Biological Chemistry*, Feb. 20, 2004, pp. 6213-6216, vol. 279, No. 8.

Hinton, P.R. et al., "An Engineered Human IgG1 Antibody with Longer Serum Half-Life", *The Journal of Immunology*, 2006, pp. 346-356, vol. 176.

Holliger, P. and Hudson, P.J., "Engineered antibody fragments and the rise of single domains", *Nature Biotechnology*, Sep. 2005, pp. 1126-1136, vol. 23, No. 9, Nature Publishing Group.

Hwang, W.Y.K. et al., "Use of human germline genes in a CDR homology-based approach to antibody humanization", *Methods*, 2005, pp. 35-42, vol. 36, Elsevier Inc.

Johnson-Léger, C.A. et al., "Junctional adhesion molecule-2 (JAM-2) promotes lymphocyte transendothelial migration", *Blood*, Oct. 1, 2002, pp. 2479-2486, vol. 100, No. 7.

Kabat, E.A., "Antibody Complementarity and Antibody Structure", *J Immunol*, 1988, pp. S25-S36.

Kamei, D.T. et al. "Quantitative Methods for Developing Fc Mutants With Extended Half-Lives", *Biotechnology and Bioengineering*, Dec. 20, 2005, pp. 748-760, vol. 92, No. 6, Wiley Periodicals, Inc.

Kashmiri, S.V.S. et al., "SDR grafting—a new approach to antibody humanization", *Methods*, 2005, pp. 25-34, vol. 36, Elsevier Inc.

Kellerman, S.A. and Green, L.L., "Antibody discovery: the use of transgenic mice to generate human monoclonal antibodies for therapeutics", *Current Opinion in Biotechnology*, 2002, pp. 593-597, vol. 13, Elsevier Science Ltd.

Kim, J.K. et al., "Mapping the site on human IgG for binding of the MHC class I-related receptor, FcRn", *Eur. J. Immunol.*, 1999, pp. 2819-2825, vol. 29, Wiley-VCH Verlag GmbH, Weinheim, Germany.

Kleihues, P. et al., "Histopathology, Classification, and Grading of Gliomas", *GLIA*, 1995, pp. 211-221, vol. 15, Wiley-Liss, Inc.

Kontermann, R.E., "Immunoliposomes for cancer therapy", *Current Opinion in Molecular Therapeutics*, 2006, pp. 39-45, vol. 8, No. 1, The Thompson Corporation.

Kretzschmar, T. and Von Rüden, T., "Antibody discovery: phage display", *Current Opinion in Biotechnology*, 2002, pp. 598-602, vol. 13, Elsevier Science Ltd.

Lai, R. et al., "The Risk of Central Nervous System Metastases after Trastuzumab Therapy in Patients with Breast Carcinoma", *Cancer*, Aug. 15, 2004, pp. 810-816, vol. 101, No. 4.

Lamagna, C. et al., "Antibody against Junctional Adhesion Molecule-C Inhibits Angiogenesis and Tumor Growth", *Cancer Res.*, Jul. 1, 2005, pp. 5703-5710, vol. 65, No. 13.

Lamagna, C. et al., "Dual Interaction of JAM-C with JAM-B and $\alpha_m\beta_2$ Integrin: Function in Junctional Complexes and Leukocyte Adhesion", *Molecular Biology of the Cell*, Oct. 2005, pp. 4992-5003, vol. 16.

Lamszus, K. et al., "Invasion as limitation to anti-angiogenic glioma therapy", *Acta Neurochir*, 2003, pp. 169-177, vol. suppl. 88, Springer-Verlag, Austria.

Lamszus, K. et al., "Inhibition of Glioblastoma Angiogenesis and Invasion by Combined Treatments Directed Against Vascular Endothelial Growth Factor Receptor-2, Epidermal Growth Factor Receptor, and Vascular Endothelial-Cadherin", *Clinical Cancer Res.* 2005, Jul. 1, 2005, pp. 4934-4940, vol. 11, No. 13.

Lazar, G.A. et al., "A molecular immunology approach to antibody humanization and functional optimization", *Molecular Immunology*, 2007, pp. 1986-1998, vol. 44, Elsevier Ltd.

Li, J. et al., "Human antibodies for immunotherapy development generated via a human B cell hybridoma technology", *Proc. Natl. Acad. Sci. USA*, Mar. 7, 2006, pp. 3557-3562, vol. 103, No. 10.

Liang, T.W. et al., "Vascular Endothelial-Junctional Adhesion Molecule (VE-JAM)/ JAM 2 Interacts with T, NK, and Dendritic Cells Through JAM 3", *The Journal of Immunology*, 2002, pp. 1618-1626, vol. 168.

Lo, B.K.C., "Antibody Humanization by CDR Grafting", *Methods in Molecular Biology*, 2004, pp. 135-159, vol. 248, Humana Press Inc., Totowa, United States.

Lonberg, N., "Human antibodies from transgenic animals", *Nature Biotechnology*, Sep. 2005, pp. 1117-1125, vol. 23, No. 9, Nature Publishing Group.

Low, S.C. et al., "Oral and pulmonary delivery of FSH-Fc fusion proteins via neonatal Fc receptor-mediated transcytosis", *Human Reproduction*, 2005, pp. 1805-1813, vol. 20, No. 7, Oxford University Press.

MacDonald, T.J. et al., "Preferential Susceptibility of Brain Tumors to the Antiangiogenic Effects of an αv Integrin Antagonist", *Neurosurgery*, Jan. 2001, pp. 151-157, vol. 48, No. 1.

Mandell, K.J. and Parkos, C.A., "The JAM family of proteins", *Advanced Drug Delivery Reviews*, 2005, pp. 857-867, vol. 57, Elsevier B.V.

Mirza, M. et al. "Coxsackievirus and adenovirus receptor (CAR) is expressed in male germ cells and forms a complex with the differentiation factor JAM-C in mouse testis", *Experimental Cell Research*, 2006, pp. 817-830, vol. 312, Elsevier Inc.

Mosavi, L.K. et al. "The ankyrin repeat as molecular architecture for protein recognition", *Protein Science*, 2004, pp. 1435-1448, vol. 13, Cold Spring Harbor Laboratory Press.

Muller, W.A., "Leukocyte-endothelial-cell interactions in leukocyte transmigration and the inflammatory response", *TRENDS in Immunology*, Jun. 2003, pp. 326-333, vol. 24, No. 6, Elsevier Science Ltd.

Nicholson, I.C. et al., "Antibody Repertoires of Four- and Five-Feature Translocus Mice Carrying Human Immunoglobulin Heavy Chain and κ and λ Light Chain Yeast Artificial Chromosomes", *The Journal of Immunology*, 1999, pp. 6898-6906, vol. 163.

Nilsson, F.Y. and Tolmachev, V., "Affibody®molecules: New protein domains for molecular imaging and targeted tumor therapy", *Current Opinion in Drug Discovery & Development*, 2007, pp. 167-175, vol. 10, No. 2, The Thomson Corporation.

Nishibori, N. et al. "Humanization of chicken monoclonal antibody using phage-display system", *Molecular Immunology*, 2006, pp. 634-642, vol. 43, Elsevier Ltd.

O'Brien, S. and Jones, T., "Humanization of Monoclonal Antibodies by CDR Grafting", *Methods in Molecular Biology*, 2003, pp. 81-100, vol. 207, Humana Press Inc., Totowa, United States.

Palmeri, D. et al., "Vascular Endothelial Junction-associated Molecule, a Novel Member of the Immunoglobulin Superfamily, is Localized to Intercellular Boundaries of Endothelial Cells", *The Journal of Biological Chemistry*, Jun. 23, 2000, pp. 19139-19145, vol. 275, No. 25.

Pardridge, W.M., "Molecular Trojan horses for blood-brain barrier drug delivery", *Current Opinion in Pharmacology*, 2006, pp. 494-500, vol. 6, Elsevier Ltd.

Sampson, J.H. et al. "Unarmed, tumor-specific monoclonal antibody effectively treats brain tumors", *Proc. Natl. Acad. Sci USA*, Jun. 20, 2000, pp. 7503-7508, vol. 97, No. 13.

Santoso, S. et al., "The Junctional Adhesion Molecule 3 (JAM-3) on Human Platelets is a Counterreceptor for the Leukocyte Integrin Mac-1", *J. Exp. Med.*, Sep. 2, 2002, pp. 679-691, vol. 196, No. 5, The Rockefeller University Press.

Shields, R.L. et al., "High Resolution Mapping of the Binding Site on Human IgG1 for FcβRI, FcγRII, FcγRIII, and FcRn and Design of IgG1 Variants with Improved Binding to the FcγR", *The Journal of Biological Chemistry*, Mar. 2, 2001, pp. 6591-6604, vol. 276, No. 9.

Sillerud, L.O. and Larson, R.S., "Design and Structure of Peptide and Peptidomimetic Antagonists of Protein-Protein Interaction", *Current Protein and Peptide Science*, 2005, pp. 151-169, vol. 6, No. 2, Bentham Science Publishers Ltd.

Takenaka, N. et al., "Immunohistochemical Detection of the Gene Product of Rous Sarcoma Virus in Human Brain Tumors", *Brain Research*, 1985, pp. 201-207, vol. 337, Elsevier Science Publishers B.V.

Tomlinson, I.M., "Next-generation protein drugs", *Nature Biotechnology*, May 2004, pp. 521-522, vol. 22, No. 5, Nature Publishing Group.

Tsurushita, N. et al., "Design of humanized antibodies: From anti-Tac to Zenapax", *Methods*, 2005, pp. 69-83, vol. 36, Elsevier Inc.

Tuettenberg, J. et al. "Angiogenesis in malignant glioma—A target for antitumor therapy?" *Critical Reviews in Oncology/Hematology*, 2006, pp. 181-193, vol. 59, Elsevier Ireland Ltd.

Vaughn, D.E. et al., "Identification of Critical IgG Binding Epitopes on the Neonatal Fc Receptor", *J. Mol. Biol.*, 1997, pp. 597-607, vol. 274, Academic Press Limited.

Walker, P.R. et al., "The Brain Parenchyma Is Permissive for Full Antitumor CTL Effector Function, Even in the Absence of CD4 T Cells", *The Journal of Immunology*, 2000, pp. 3128-3135, vol. 165.

Ward, E.S. and Ghetie, V., "The effector functions of immunoglobulins: implications for therapy", *Therapeutic Immunology*, 1995, pp. 77-94, vol. 2, Blackwell Science Ltd.

Winter, G. et al., "Making Antibodies by Phage Display Technology", *Annu. Rev. Immunol.*, 1994, pp. 433-455, vol. 12.

Zen, K. et al., "JAM-C is a Component of Desmosomes and a Ligand for CD11b/CD18-mediated Neutrophil Transepithelial Migration", *Molecular Biology of the Cell*, Aug. 2004, pp. 3926-3937, vol. 15.

Hoogenboom, H.R., "Overview of Antibody Phage-Display Technology and its Applications", *Methods in Molecular Biology*, pp. 1-37, vol. 178, Humana Press Inc., Totowa, United States, 2002.

Aurrand-Lions, M. et al. "Heterogeneity of endothelial junctions is reflected by differential expression and specific subcellular localization of the three JAM family members" *Blood*, Dec. 15, 2001, pp. 3699-3707, vol. 98, No. 13.

Skolnick, J. et al. "From genes to protein structure and function: novel applications of computational approaches in the genomic era" *Trends in Biotech*, Jan. 2000, pp. 34-39, vol. 18, No. 1.

Attwood, T. K. "The Babel of Bioinformatics" *Science*, Oct. 20, 2000, pp. 471-473, vol. 290.

Database EMBL (Online), Accession No. AI154320, Oct. 1, 1998, Marra, M. "EST: Mouse mammary gland cDNA clone IMAGE:1447499", XP-002144155, pp. 1-2.

Database EMBL (Online), Accession No. AI663309, May 11, 1999, Marra, M. "EST: *M. musculus* cDNA clone IMAGE:1970215 similar to Junctional Adhesion Molecule", XP-002144156, pp. 1-2.

Database EMBL (Online), Accession No. AW162934, Nov. 11, 1999, Hillier, L. "EST: *H. sapiens* cDNA clone IMAGE:2783568 similar to Junctional Adhesion Molecule", XP-002144157, pp. 1-2.

Martin-Padura, I. et al. "Junctional Adhesion Molecule, a Novel Member of the Immunoglobulin Superfamily That Distributes at Intercellular Junctions and Modulates Monocyte Transmigration" *J. Cell. Biol.*, Jul. 13, 1998, pp. 117-127, vol. 142, No. 1.

Heath, J.K. et al. "The human A33 antigen is a transmembrane glycoprotein and a novel member of the immunoglobulin superfamily" *Proc. Natl. Acad. Sci. USA*, Jan. 21, 1997, pp. 469-474, vol. 94, No. 2.

Jermutus, L. et al. "Recent advances in producing and selecting functional proteins by using cell-free translation" *Current Opinion in Biotechnology*, Oct. 1998, pp. 534-548, vol. 9, No. 5.

Dufresne, G. et al. "Genetic sequences: how are they patented?" *Nature Biotechnology*, Feb. 2004, pp. 231-232, vol. 22, No. 2.

Hanes, J. et al. "In vitro selection and evolution of functional proteins by using ribosome display" *Proc. Natl. Acad. Sci. USA*, May 13, 1997, pp. 4937-4942, vol. 94, No. 10.

Webber, C. et al. "Genes and homology" *Current Biology*, May 4, 2004, pp. R332-R333, vol. 14, No. 9.

Lewin, R. "When Does Homology Mean Something Else?" *Science*, Sep. 25, 1987, p. 1570, vol. 237, No. 4822.

Sczakiel, G. The design of antisense RNA *Antisense Nucleic Acid Drug Dev.*, Aug. 1997, pp. 439-444, vol. 7, No. 4, abstract only.

Johnstone, C. N. et al. "Characterization of mouse A33 antigen, a definitive marker for basolateral surfaces of intestinal epithelial cells" *Am. J. Physiol Gastrointest Liver Physiol.*, Sep. 2000, pp. G500-G510, vol. 279, No. 3.

Orlova, V. V. et al. "Junctional adhesion molecule-C regulates vascular endothelial permeability by modulating VE-cadherin-mediated cell-cell contacts" *The Journal of Experimental Medicine*, Nov. 27, 2006, pp. 2703-2714, vol. 203, No. 12.

Office Action mailed Feb. 6, 2002 in U.S. Appl. No. 09/524,531, filed Mar. 13, 2000.

Office Action mailed Dec. 3, 2003 in U.S. Appl. No. 09/524,531, filed Mar. 13, 2000.

Office Action mailed Jun. 30, 2004 in U.S. Appl. No. 09/524,531, filed Mar. 13, 2000.

Office Action mailed Jun. 14, 2006 in U.S. Appl. No. 11/025,834, filed Dec. 30, 2004.

Office Action mailed Jan. 30, 2007 in U.S. Appl. No. 11/025,834, filed Dec. 30, 2004.

Office Action mailed Aug. 24, 2007 in U.S. Appl. No. 11/025,834, filed Dec. 30, 2004.

Office Action mailed Nov. 15, 2010 in U.S. Appl. No. 12/703,439, filed Feb. 10, 2010.

Office Action mailed Mar. 23, 2011 in U.S. Appl. No. 12/703,439, filed Feb. 10, 2010.

Bazzoni, G. "The JAM family of junctional adhesion molecules", *Current Opinion in Cell Biology*, 2003, pp. 525-530, vol. 15, No. 5.

Naik, M.U. et al. "Signaling through JAM-1 and $\alpha_v\beta_3$ is required for the angiogenic action of bFGF: dissociation of the JAM-1 and $\alpha_v\beta_3$ complex", *Blood*, Sep. 15, 2003, pp. 2108-2114, vol. 102, No. 6.

Vestweber, D. "Regulation of endothelial cell contacts during leukocyte extravasation", *Current Opinion in Cell Biology*, 2002, pp. 587-593, vol. 14, No. 5.

Vestweber, D. "Molecular mechanisms that control endothelial cell contacts", *Journal of Pathology*, 2000, pp. 281-291, vol. 190, No. 3.

Chen, J. et al. "B cell development in mice that lack one or both immunoglobulin κ light chain genes", *The EMBO Journal*, 1993, pp. 821-830, vol. 12, No. 3.

Chen, J. et al. "Immunoglobulin gene rearrangement in B cell deficient mice generated by targeted deletion of the $J_H$ locus", *International Immunology*, 1993, pp. 647-656, vol. 5, No. 6.

Choi, T.K. et al. "Transgenic mice containing a human heavy chain immunoglobulin gene fragment cloned in a yeast artificial chromosome", *Nature Genetics*, Jun. 1993, pp. 117-123, vol. 4.

Crowther, M. et al. "Microenvironmental influence on macrophage regulation of angiogenesis in wounds and malignant tumors", *Journal of Leukocyte Biology*, Oct. 2001, pp. 478-490, vol. 70.

Fishwild, D.M. et al. "High-avidity human IgGκ monoclonal antibodies from a novel strain of minilocus transgenic mice", *Nature Biotechnology*, Jul. 1996, pp. 845-851, vol. 14.

Harding, F.A. et al. "Class switching in human immunoglobulin transgenic mice", *Annals New York Academy of Sciences*, 1995, pp. 536-546, vol. 764.

Jones, P.T. et al. "Replacing the complementarity-determining regions in a human antibody with those from a mouse", *Nature*, May 29, 1986, pp. 522-525, vol. 321.

Joosten, V. et al. "The production of antibody fragments and antibody fusion proteins by yeasts and filamentous fungi", *Microbial Cell Factories*, 2003, pp. 1-15, vol. 2, No. 1.

Kohler, G. et al. "Continuous cultures of fused cells secreting antibody of predefined specificity", *Nature*, Aug. 7, 1975, pp. 495-497, vol. 256.

Lonberg, N. et al. "Antigen-specific human antibodies from mice comprising four distinct genetic modifications", *Nature*, Apr. 28, 1994, pp. 856-859, vol. 368.

Lonberg, N. et al. "Human antibodies from transgenic mice", *Intern. Rev. Immunol.*, 1995, pp. 65-93, vol. 13.

Lonberg, N. "Transgenic approaches to human monoclonal antibodies", *Handbook of Experimental Pharmacology*, 1994, pp. 49-101, vol. 113.

Merino, R. et al. "The Yaa gene abrogates the major histocompatibility complex association of murine lupus in (NZB × BXSB)$F_1$ Hybrid Mice", *J. Clin. Invest.*, Aug. 1994, pp. 521-525, vol. 94, No. 2.

Morrison, S.L. et al. "Transfectomas provide novel chimeric antibodies", *Science*, Sep. 20, 1985, pp. 1202-1207, vol. 229.

Murdock, C. et al. "Mechanisms regulating the recruitment of macrophages into hypoxic areas of tumors and other ischemic tissues", *Blood*, Oct. 15, 2004, pp. 2224-2234, vol. 104, No. 8.

Padlan, E.A. "A possible procedure for reducing the immunogenicity of antibody variable domains while preserving their ligand-binding properties", *Molecular Immunology*, 1991, pp. 489-498, vol. 28, No. 4/5.

Padlan, E.A. "Anatomy of the antibody molecule", *Molecular Immunology*, 1994, pp. 169-217, vol. 31, No. 3.

Queen, C. et al. "A humanized antibody that binds to the interleukin 2 receptor", *Proc. Natl. Acad. Sci. USA*, Dec. 1989, pp. 10029-10033, vol. 86.

Riechmann, L. et al. "Reshaping human antibodies for therapy", *Nature*, Mar. 24, 1988, pp. 323-327, vol. 332, No. 24.

Taylor, L.D. et al. "A transgenic mouse that expresses a diversity of human sequence heavy and light chain immunoglobulins", *Nucleic Acids Research*, 1992, pp. 6287-6295, vol. 20, No. 23.

Tuaillon, N. et al. "Human immunoglobulin heavy-chain minilocus recombination in transgenic mice: Gene-segment use in μ and γ transcripts", *Proc. Natl. Acad. Sci. USA*, Apr. 1993, pp. 3720-3724, vol. 90.

Tuaillon, N. et al. "Biased utilization of $D_{HQ52}$ and $J_H$A gene segments in a human Ig transgenic minilocus is independent of antigenic selection", 1994, pp. 2912-2920, vol. 152.

Verhoeyen, M. et al. "Reshaping human antibodies: grafting an antilysozyme activity", *Science*, Mar. 25, 1988, pp. 1534-1536, vol. 239.

Antibody/Collaborator Table, Aug. 14, 2002, 1 page.

Mountain, A. et al. "Engineering Antibodies for Therapy", *Biotechnology and Genetic Engineering Reviews*, Dec. 1992, pp. 1-142, vol. 10.

de Haard, H. et al. "Creating and engineering human antibodies for immunotherapy", *Advanced Drug Delivery Reviews*, 1998, pp. 5-31, vol. 31.

Figini, M. et al. "Isolation of Human Monoclonal Antibodies Using Guided Selection with Mouse Monoclonal Antibodies", *Methods in Molecular Biology*, 2002, pp. 207-217, vol. 178.

Rader, C. et al. "A phage display approach for rapid antibody humanization: Designed combinatorial V gene libraries", *Proc. Natl. Acad. Sci. USA*, Jul. 1998, pp. 8910-8915, vol. 95.

Klimka, A. et al. "Human anti-CD30 recombinant antibodies by guided phage antibody selection using cell panning", *British Journal of Cancer*, 2000, pp. 252-260, vol. 83, No. 2.

Beiboer, S. et al. "Guided Selection of a Pan Carcinoma Specific Antibody Reveals Similar Binding Characteristics yet Structural Divergence Between the Original Murine Antibody and its Human Equivalent", *J. Mol. Biol.*, 2000, pp. 833-849, vol. 296.

Schmidt, A. et al. "Generation of human high-affinity antibodies specific for the fibroblast activation protein by guided selection", *Eur. J. Biochem.*, 2001, pp. 1730-1738, vol. 268.

Ditzel, H. et al. "Determinants of Polyreactivity in a Large Panel of Recombinant Human Antibodies from HIV-1 Infection", *The Journal of Immunology*, 1996, pp. 739-749, vol. 157.

Rudikoff, et al. "Single amino acid substitution altering antigen-binding specificity" *Proc. Natl. Acad. Sci. USA*, 1982, pp. 1979-1983, vol. 79.

Padlan, et al. "Identification of specificity-determining residues in antibodies" *FASEB Journal*, 1995, pp. 133-139, vol. 9.

Li, C. H. et al. "β-Endorphin omission analogs: Dissociation of immunoreactivity from other biological activities", *Proc. Natl. Acad. Sci. USA*, Jun. 1980, pp. 3211-3214, vol. 77, No. 6.

MacCallum, R. M. et al. "Antibody-antigen Interactions: Contact Analysis and Binding Site Topography", *J. Mol. Biol.*, 1996, pp. 732-745, vol. 262.

Lederman, S. et al. "A Single Amino Acid Substitution in a Common African Allele of the CD4 Molecule Ablates Binding of the Monoclonal Antibody, OKT4", *Molecular Immunology*, 1991, pp. 1171-1181, vol. 28, No. 11.

Bendig, M. M. "Humanization of Rodent Monoclonal Antibodies by CDR Grafting", *Methods: A Companion to Methods in Enzymology*, 1995, pp. 83-93, vol. 8.

Colman, P. M. "Effects of amino acid sequence changes on antibody-antigen interactions", *Research in Immunology*, 1994, pp. 33-36.

Casset, F. et al. "A peptide mimetic of an anti-CD4 monoclonal antibody by rational design", *Biochemical and Biophysical Research Communications*, 2003, pp. 198-205, vol. 307.

Taylor, L. D. et al. "Human immunoglobulin transgenes undergo rearrangement, somatic mutation and class switching in mice that lack endogenous IgM", *International Immunology*, 1994, pp. 579-591, vol. 6, No. 4.

Paul, W. E., Fundamental Immunology, 3$^{rd}$ Edition, Chapter 9, Immunoglobulins, Structure and Function, 1993, pp. 284-314, Raven Press, Ltd., New York.

Author Guide—*Blood* (from Internet), 2007, pp. 8-9.

Office Action mailed Feb. 21, 2007 in U.S. Appl. No. 10/738,123, filed Dec. 18, 2003.

Office Action mailed Sep. 7, 2007 in U.S. Appl. No. 10/738,123, filed Dec. 18, 2003.

Office Action mailed Aug. 7, 2008 in U.S. Appl. No. 10/738,123, filed Dec. 18, 2003.

Office Action mailed Apr. 27, 2009 in U.S. Appl. No. 10/738,123, filed Dec. 18, 2003.

Office Action mailed Jul. 8, 2009 in U.S. Appl. No. 10/579,105, filed Feb. 6, 2007.

Office Action mailed Jan. 5, 2010 in U.S. Appl. No. 10/579,105, filed Feb. 6, 2007.

Office Action mailed Apr. 5, 2011 in U.S. Appl. No. 12/608,029, filed Oct. 29, 2009.

JUNCTIONAL ADHESION MOLECULE-C (JAM-C) BINDING COMPOUNDS AND METHODS OF THEIR USE

CROSS-REFERENCE TO RELATED APPLICATIONS

This application is the U.S. national stage application of International Patent Application No. PCT/IB2007/002861, filed Sep. 28, 2007, which claims the benefit of U.S. Provisional Patent Application No. 60/827,389, filed Sep. 28, 2006, the disclosure of which is hereby incorporated by reference in its entirety, including all figures, tables and amino acid or nucleic acid sequences.

FIELD OF THE INVENTION

The instant invention relates to the treatment of cancer, in particular brain cancer. More specifically the invention relates to the treatment of glioma with compounds that specifically bind to JAM-B or JAM-C, such as antibodies and antagonists specifically binding to JAM-B or JAM-C.

BACKGROUND OF THE INVENTION

Gliomas

The major cell types of the brain are neurons, oligodendrocytes, which are the cells forming the myelin sheaths around neuronal axons in the Central Nervous System (CNS), and astrocytes, the cells supporting both neuron and oligodendrocyte functions. Oligodendrocytes and astrocytes, together with ependymal cells that line the ventricular system, constitute the glia, the specialised connective tissue of the CNS.

Gliomas are tumours that show predominant glial differentiation and are the most frequent subtype of primary brain tumours, with an incidence of 5-10 per 100.000 in the general population per year. The vast majority of gliomas are of sporadic origin, but some genetic diseases have been associated with an increased predisposition to their development like Neurofibromatosis type 1 (a familial syndrome characterised by mutations in the NF1 tumour suppressor gene), Li-Fraumeni (inherited germ-line mutations in the TP53 gene) and Turcot syndromes (a familial syndrome characterised by polyposis cancers linked to inherited mutations in the APC gene). The severity of gliomas appears absolutely obvious given the fundamental role of the brain and the damages that can be caused by neurological destruction. Furthermore, even the so-called benign forms are in reality most often lethal, mainly because of the high propensity of these tumours to spread into normal brain structures and to progress towards malignancy. Therefore, gliomas are considered to be among the most devastating of human malignancies, and despite progress in therapy, including surgery, radiation and chemotherapy, the prognosis for patients affected by these diseases is often dismal.

The clinical signs that lead to diagnosis of gliomas include seizures, an increasing intracranial pressure leading to leakage of the blood-brain-barrier and oedema, which provokes nausea, vomiting, and headache, and progressive neurological and cognitive deficits. Magnetic Resonance Imaging (MRI) is then useful to identify the location and features of the tumour mass. The classification and grading of the type of glioma is possible after histological examination of a tumour sample, and is based on the hypothetical line of differentiation of the tumour cell. According to the World Health Organization (WHO) classification, gliomas include tumours composed mainly by ependymal cells (ependymomas), oligodendrocytes (oligodendrogliomas), mixtures of different glial cells (mixed gliomas, for instance oligoastrocytomas) and astrocytes (astrocytomas).

Astrocytoma

Classification and Histopathology

Among gliomas, the most common are astrocytomas, which are composed of astrocyte-like cells and often arise in the cerebrum. In children, they occur mainly in the cerebellum, in brain stem, and optic chiasma. Astrocytomas include tumours with highly variable natural behaviour and prognosis. They are usually classified in 4 grades (see Table 1) mainly on the basis of histopathological parameters.

WHO grade I astrocytoma (pilocytic astrocytoma) is more frequent in children, generally has low proliferative potential and is cured by surgery in most cases.

WHO grade II astrocytomas (diffuse astrocytoma) are poorly defined tumours that infiltrate the normal brain tissue, with isolated tumoral cells often observed at extraordinary distance from the primary tumour. They show a moderate cellularity and sporadic nuclear atypia. Most patients with grade II astrocytoma will recur with a higher grade tumour within 6 to 8 years.

WHO grade III astrocytomas (anaplastic astrocytoma) are distinguished from grade II tumours by their greater cellularity, increased mitotic activity and nuclear pleomorphism (anaplasia). Despite some long-term survivors, the median survival of patients with grade III astrocytoma is around 3 years.

WHO grade IV astrocytomas (or glioblastomas) preferentially arise in the cerebral hemispheres of adults and are highly devastating tumours. Compared to anaplastic astrocytomas they are characterized by the additional presence of endothelial cell proliferation and necrosis. They may develop after a history of lower grade astrocytoma (secondary glioblastoma) or de novo (primary glioblastoma). The prognosis is dismal for both types, with a median survival around 1 year, despite some advances with combined treatments (irradiation and chemotherapy).

TABLE 1

WHO classification and grade criteria for astrocytoma.

| WHO Grade | WHO Designation | Histological Criteria |
|---|---|---|
| I | Pilocytic Astrocytoma | |
| II | Diffuse Astrocytoma | One criterion: usually nuclear atypia |
| III | Anaplastic Astrocytoma | Two criteria: usually nuclear atypia and mitotic activity |
| IV | Glioblastoma | Three criteria: nuclear atypia, mitosis, endothelial proliferation and/or necrosis |

Primary and Secondary Glioblastoma

As mentioned above, two subtypes of glioblastoma are distinguished on the basis of their clinical features: primary glioblastoma, which develop very rapidly, usually in elderly people, without any evidence of pre-existing lesions, and secondary glioblastoma, which derives from the malignant evolution of previously diagnosed low grade astrocytoma and is more frequent in young patients. Histologically these two tumour types are indistinguishable and the clinical outcome is also similar, but genetically they are different.

Secondary Glioblastoma

Secondary glioblastomas in their initial phase as low grade astrocytomas are characterised by the frequent disruption of the TP53 locus (over 60% of grade II astrocytomas), with mutations in the gene (65%) and Loss of Heterozygosity (LOH) on the chromosome (17p13). Disruption of the p53 pathway dismantles two important cellular processes, as p53 functions as tumour suppressor by controlling cell cycle progression at the G1/S and G2/M checkpoints and apoptosis in response to several extracellular stimuli including DNA damage. Therefore a non-functional p53 pathway confers a growth advantage and genomic instability to astrocytoma cells, although alone is not sufficient for astrocytoma initiation.

The additional genetic alterations found in low grade astrocytomas that seem to be necessary for their initiation involve activation of Receptor Tyrosine Kinases (RTKs) in order to render astrocytoma cells independent from growth factors for their survival. A crucial mediator of RTKs signalling is the c-Src non-receptor tyrosine kinase. c-Src directly associate to RTKs activated by the binding of their corresponding growth factors and is concomitantly activated thereby synergising and cooperating in the stimulation of the multiple pathways activated by RTKs.

Primary Glioblastoma

Primary glioblastomas show deregulation of the same genetic pathways as secondary glioblastomas, namely the p53, the RTK-Ras, the RB and the AKT pathways, but they use different mechanisms.

In primary glioblastomas the p53 pathway is not disrupted by direct mutations of the TP53 gene, but rather through amplification and overexpression of the MDM2 gene (10% and 50%, respectively) and loss of p19 (40%). MDM2 functions as a negative regulator of the p53 transcriptional activity by targeting it for ubiquitin-mediated degradation through direct protein-protein binding. Furthermore MDM2 transcription is induced by p53 thus establishing a negative feedback loop that regulates the activity of both proteins. P19 prevents p53 degradation by directly binding to MDM2. p19 is encoded in the same CDKN2A gene as p16 by an alternative reading frame (ARF, another name of p19). This might explain why LOH of the CDKN2A locus on chromosome 9p21 is very frequent in primary glioblastomas (~40%) since it disrupts two pathways at the same time: the p53 and the RB pathways. Whether the simultaneous deregulation of two crucial pathways for gliomagenesis might be one of the reasons for the extremely rapid development of primary glioblastoma remains to be clarified.

Angiogenesis and Anti-angiogenic Therapy of Glioma

Gliomas are among the most vascularised of human cancers. The process of angiogenesis, that is the formation of new vessels by sprouting of pre-existing ones or incorporation of endothelial cell progenitors, is critical for a tumour to develop. Without supply of oxygen and nutrients cancer cells cannot sustain all their malignant activities including indiscriminate growth, survival and invasion. Therefore, induction of an active production of new blood vessels is a crucial step during tumour progression.

In gliomas, control of angiogenesis is disturbed. There is often a poorly functional vasculature incapable of adequate oxygen supply inside the tumour resulting in the generation of large regions of low oxygen tension and subsequent necrosis. The presence of hypoxic areas in the tumour is at the origin of a vicious cycle, where hypoxia stimulates the formation of new blood vessels and these, given their structural and functional abnormalities are unable to provide sufficient oxygen supply, thereby causing new hypoxia to form.

Anti-angiogenic therapies have been proposed for the treatment of glioma (Tuettenberg et al., 2006). It has been noted, however, that inhibition of angiogenesis, while inhibiting glioma growth, leads to a substantial increase in glioma invasiveness (Lamszus et al., 2003), thus limiting the applicability of such approach. It has therefore been proposed to combine anti-angiogenic therapy of glioma with a therapy that inhibits gloma spreading (Lamszus et al., 2005).

Spreading

One of the main reasons accounting for glioma and astrocytoma lethality is the property of such tumours to spread. Astrocytomas very rarely metastasize outside the CNS, but the invasive cells remaining after surgical resection, regardless of its extension, will inevitably spread everywhere within the brain and lead to recurrence with a significant contribution to the demise of the patients. Already several decades ago neurosurgeons realised that even a radical resection, as hemispherectomy could not prevent astrocytoma recurrence and improve the survival of the patient. Astrocytoma cells can be found at large distances from the core lesion (several centimeters) and mainly disseminate as single cells in an integrin-dependent mechanism of migration defined as mesenchymal. They typically invade throughout the brain following three main anatomical structures: (i) the myelinated fiber tracts, usually of the corpus callosum; (ii) the abluminal surface of blood vessels and (iii) the glia limitans, the structure formed by astrocytes foot processes underneath the pia mater at the periphery of the brain parenchyma. The reason for these preferences are not yet clear, but the composition of the substrates supporting glioma cell migration is very likely to be of relevance.

Invasion of glioma cells requires the activation of several cellular processes. First, the cells need to adhere to the extracellular matrix. This step is important because the simultaneous link of membrane proteins with the extracellular environment and the cell cytoskeleton provides the cells the necessary force for traction and motility. Second, the cells have to detach from adjacent cells by disrupting their junctions. Third, to generate the space for movement, the cells have to locally degrade the extracellular matrix (ECM). This is accomplished through the release by glioma cells of active proteases. Fourth, an entire rearrangement of the cytoskeleton is needed for the cell to extend protrusions, lamellipodia and filopodia, establish adhesions in the direction of migration and finally retract its cell body. All these cell behaviors are orchestrated by an array of molecules; interaction with the ECM is mainly mediated by integrins establishing focal contacts, cell detachment from neighboring cells requires disruption of cadherins cell-cell junctions, degradation of the ECM is accomplished by metalloproteinases (MMPs) and the urokinase-plasminogen proteolytic system, and rearrangement of the cytoskeleton is governed by Rho family small GTPases.

In the US, approximately, 15,000 patients die from glioblastoma per year. The median survival time does not exceed 15 months. In view of the poor prognosis of glioma and in particular anaplastic astrocytoma and glioblastoma and the inavailibity of efficient treatment there is thus a need for new drug targets and compounds for the treatment of said disorders. In particular there is a need for compounds that inhibit growth of glioma and in particular anaplastic astrocytoma and glioblastoma. There is a need for compounds that inhibit or reduce spreading of glioma and in particular anaplastic astrocytoma and glioblastoma. New compounds for the treatment of glioma must be able to cross the blood-brain barrier. Additionally new targets and compounds for the treatment of glioma must be very specific, as cross-reactivity with normal brain tissue may lead to neurotoxicity with intolerable side effects (Gerber and Laterra, 2007).

While monoclonal antibodies have become standard therapy for breast and colon cancer as well as other malignancies, they were only used experimentally in the treatment of glioma, which poses unique challenges to antibody therapies (Gerber and Laterra, 2007). In particular, the blood-brain barrier is considered to be a major problem for successful application of high molecular weight compounds such as antibodies or other proteins to the treatment of glioma and other brain tumours as such high molecular weight compounds generally do not cross this barrier (Pardridge, 2006). The anti-cancer antibody trastuzumab, for example, fails to cross the blood-brain barrier leading to brain metastasis of breast cancer patients (Lai et al., 2004; Bendell et al., 2003). As anti-tumour antibodies that were systemically delivered had no therapeutic effect, while being effective when locally administered into the brain, local delivery of large molecular entities such as antibodies for the treatment of glioma has been the mainstay of therapy (Sampson et al., 2000).

Junctional Adhesion Molecules (JAMs)

General Features

Junctional Adhesion Molecules (JAMs) are a family of proteins belonging to the immunoglobulin Superfamily (IgSf) class of adhesion molecules. They are generally localised at sites of cell-cell contacts and particularly abundant in tight junctions, the specialised cellular structures that keep cell polarity and serve as barriers to prevent the diffusion of molecules across intercellular spaces and along the basolateral-apical regions of the plasma membrane.

Several human and mouse Junctional Adhesion Molecules (JAMs) have been simultaneously cloned in different laboratories and the amino and nucleic acid sequences published. This has raised confusion in their nomenclature which was the subject of a complete revision (Muller, 2003; Mandell and Parkos, 2005). The current nomenclature described in Table 2 will be used herein.

TABLE 2

JAM nomenclature

| Current Nomenclature | Previous Nomenclature | Species |
|---|---|---|
| JAM-A | JAM/JAM-1 | Mouse |
|  | JAM/JAM-1 | Human |
|  | F11 Receptor | Human |
| JAM-B | JAM-3 | Mouse |
|  | VE-JAM | Mouse, Human |
|  | JAM2 | Human |
| JAM-C | JAM-2 | Mouse |
|  | JAM3 | Human |
|  | JAM-3 | Human |

Among the family members JAM-A, JAM-B, and JAM-C share a similar protein structure with 31-36% amino acid identity, and molecular masses ranging from 40-45 kDa. JAMs are characterised by two extracellular immunoglobulin domains, one membrane distal of $V_H$-type and one membrane proximal of $C_2$-type, a trans-membrane domain and a cytoplasmic domain. The extracellular domains contain several putative N-glycosylation sites.

In addition, the $V_H$-type Ig domain mediates cis dimerisation of JAM-A and trans homotypic associations between JAM-A dimers emanating from opposing cells. The cis dimerisation motif is conserved in JAM-B and JAM-C which dimerise and trans-interact in a similar way (Lamagna et al., 2005b).

The cytoplasmic domains contain potential tyrosine as well as serine/threonine phosphorylation sites and are characterised by the presence of type II PDZ-binding motifs. PDZ binding motifs are often found in scaffolding proteins where they mediate protein-protein interactions, and the first proteins identified with such structures were PSD-95, Discs-large A and Zonula Occludens-1, hence the name PDZ. Additional JAM proteins representing a distinct subfamily containing type I PDZ binding motifs have recently been described. These JAMs include Coxsackie and adenovirus Receptor (CAR), Endothelial cell-selective Adhesion Molecule (ESAM), and JAM-4. However, the presence of a diverse type of PDZ binding motif suggests that they might interact with diverse sets of intracellular partner molecules and exert different functions.

JAM-A, JAM-B and JAM-C have different patterns of tissue and cell distribution, intracellular and extracellular molecular partners and functions.

TABLE 3

Expression of JAM-A, JAM-B and JAM-C in mouse and human.

|  | Mouse | Human |
|---|---|---|
| JAM-A | Endothelial cells | Endothelial cells |
|  | Epithelial cells | Epithelial cells |
|  | Platelets | Platelets |
|  | Dendritic cells | Monocytes |
|  |  | Lymphocytes |
|  |  | Neutrophils |
| JAM-B | Endothelial cells | Endothelial cells |
|  | Lymphatic | Lymphatic |
|  | Endothelial cells | Endothelial cells |
| JAM-C | Endothelial cells | Endothelial cells |
|  | Lymphatic | Lymphatic |
|  | Endothelial cells | Endothelial cells |
|  | Spermatids | Epithelial cells |
|  |  | Platelets |
|  |  | Dendritic cells |
|  |  | Lymphocytes |

TABLE 4

Extracellular ligands of JAM-A, JAM-B and JAM-C.

|  | JAM ligands | Integrin ligands |
|---|---|---|
| JAM-A | JAM-A | LFA-1 (CD11a/CD18, $\alpha_L\beta_2$) |
|  |  | reovirus |
|  |  | $\alpha_V\beta_3$ |
| JAM-B | JAM-B | VLA-4 ($\alpha_4\beta_1$) |
|  | JAM-C |  |
| JAM-C | JAM-B | MAC-1 ($\alpha_M\beta_2$, CD11b/CD18) |
|  | JAM-C | p150, 95 ($\alpha_X\beta_2$, CD11c/CD18) |
|  | CAR |  |

JAM-B

JAM-B expression has been shown in endothelial cells and lymphatic endothelial cells in both mouse and human. JAM-B expression was detected on human endothelial cells in inflammatory sites and tumour foci. In the brain, Northern blot analysis revealed a weak expression of JAM-B mRNA, but no analysis was performed at the protein level, and the cell types expressing JAM-B in brain were not identified (Palmeri et al., 2000).

The cellular localisation of JAM-B seems to differ from that of other family members. JAM-B does not appear to be situated in tight junction structures but rather to be more diffusely distributed on the plasma membrane, as demonstrated by the ectopic expression of JAM-B in Madin-Darby canine kidney (MDCK) epithelial cells.

JAM-B can establish both homophilic trans-interactions and heterophilic associations with JAM-C. It appears that these heterophilic bindings mediate interaction of JAM-B on endothelial cells with JAM-C on leukocytes and platelets. JAM-B also interacts with integrin $\alpha_4\beta_1$ and this binding seems to require prior engagement of JAM-C.

JAM-C

JAM-C expression has been observed in both mouse and human endothelial cells and lymphatic endothelial cells, and in several human leukocytes and platelets. In addition, JAM-C was found in human intestinal epithelia and in mouse spermatids. In the human brain, by Northern blot analysis JAM-C mRNA was expressed in several regions, but no investigations of protein expression and of the cell types expressing JAM-C was performed (Arrate et al., 2001).

JAM-C is localised in tight junctions by confocal analysis and co-distribution with the known tight junction protein occludin (Aurrand-Lions et al., 2001a). However, in intestinal human epithelia JAM-C was detected in the basolateral membrane of the cells in desmosomal structures (Zen et al., 2004), suggesting the existence of cell-type specific sub-cellular localisation of JAM-C and consequently potential different functions for this protein.

JAM-C can engage in homotypic and, with higher affinity, in heterotypic trans-interactions with JAM-B (Lamagna et al., 2005b). In addition, other ligands for JAM-C include integrins $\alpha_M\beta_2$ (MAC-1, CD11b/CD18) and $\alpha_X\beta_2$ (p150/95, CD11c/CD18) (Chavakis et al., 2004; Santoso et al., 2002; Zen et al., 2004) and CAR (Mirza et al., 2006).

To date JAM-C has been implicated in leukocyte trafficking, angiogenesis and cell polarity. It has been shown that anti-JAM-C antibodies block lymphocyte trans-endothelial migration in vitro (Johnson-Leger et al., 2002a), and that JAM-C promotes neutrophil trans-endothelial migration in vitro and in vivo in a $\alpha_M\beta_2$ dependent manner.

The role of JAM-C in angiogenesis has been demonstrated both in vitro and in vivo (Imhof and Aurrand-Lions, 2000; Imhof and Aurrand-Lions, 2005; Lamagna et al., 2005a). In particular, an antibody against JAM-C was shown to block the in vitro outgrowth of blood vessels in an aortic ring assay. In addition, an anti-JAM-C was shown to block the in vitro outgrowth of blood vessels in an aortic ring assay. In addition, an anti-JAM-C antibody inhibited in vivo growth and reduced tumour associated angiogenesis of a Lewis Lung Carcinoma (LLC) mouse tumour model (Lamagna et al., 2005a). The reduction in tumour-associated angiogenesis was attributed to a decreased recruitment of macrophages to the tumour bed, since the anti-JAM-C antibody had no effect on endothelial cell proliferation and apoptosis in vitro.

WO 2006/084078 reports on immunohistochemistry staining of different tumour tissues with the murine anti-human JAM-C antibodies PACA4 and LUCA14. The staining pattern was heterogenous with no consistent positive staining of the tumour tissues tested with PACA4 and LUCA14. Various normal and tumour cell lines were also tested for JAM-C expression with PACA4 and LUCA14. A number of glioma-derived cell lines stained weakly positive or positive with only PACA4. The staining pattern on non-tumour brain tissue; i.e. astrocytes, however, was not reported. It thus, remains unclear whether JAM-C is expressed highly and specifically on astrocytoma or glioblastoma, in order to be a suitable target for the treatment of glioma. Additionally it remains unclear whether anti-JAM-C antibodies or other high molecular weight compounds specifically binding to JAM-C would cross the blood-brain barrier in order to be effective in the treatment of glioma or other brain tumours when administered systemically.

SUMMARY OF THE INVENTION

It has now surprisingly been found by the present inventors that JAM-C is specifically expressed on glioma tumour cells, whereas it is essentially absent from non-tumour astrocytes.

It has also surprisingly been found by the present inventors that JAM-B is specifically expressed on glioma tumour cells, whereas it is essentially absent from non-tumour astrocytes.

It has also surprisingly been found by the present inventors that compounds that specifically bind to JAM-C inhibit the growth of gliomas, independent of inhibition of angiogenesis.

It has also surprisingly been found by the present inventors that compounds that specifically bind to JAM-C inhibit the growth of gliomas in vivo when administered systemically.

Furthermore, no negative side effects were observed in vivo after treatment with an antibody specifically binding to JAM-C.

Even more surprisingly it has been found by the present inventors that an antibody that specifically binds to JAM-C inhibits the spreading of gliomas. This was completely unexpected since antibodies binding specifically to JAM-C are anti-angiogenic, and anti-angiogenic compounds were known to lead to increased spreading of gliomas.

Consequently, it has been found by the present inventors that a compound that specifically binds to JAM-C, such as an antibody to JAM-C (e.g. the monoclonal antibody D33), can be used for the treatment of glioma without the requirement for a concomitant treatment for the inhibition of glioma spreading.

One aspect of the invention is the use of a compound that specifically binds to JAM-C for the treatment of glioma.

Another aspect of the invention is the use of a compound that specifically binds to JAM-B for the treatment of glioma.

Another aspect of the instant invention relates to use of an antibody or antigen binding fragment thereof that specifically binds to JAM-C for the inhibition of growth of glioma or the spreading of glioma.

Another aspect of the invention is the use of a compound that specifically binds to JAM-B and a compound that specifically binds to JAM-C in combination for the treatment of glioma.

Another aspect of the invention is the rat monoclonal antibody D33, which specifically binds to JAM-C and is produced by the hybridoma cell line that has been deposited at the European Collection of Cell Cultures (ECACC) under accession no. 06092701.

Another aspect of the invention is the hybridoma cell line that has been deposited at the European Collection of Cell Cultures (ECACC) under accession no. 06092701, which produces the antibody D33.

DETAILED DESCRIPTION OF THE INVENTION

Figure 1:
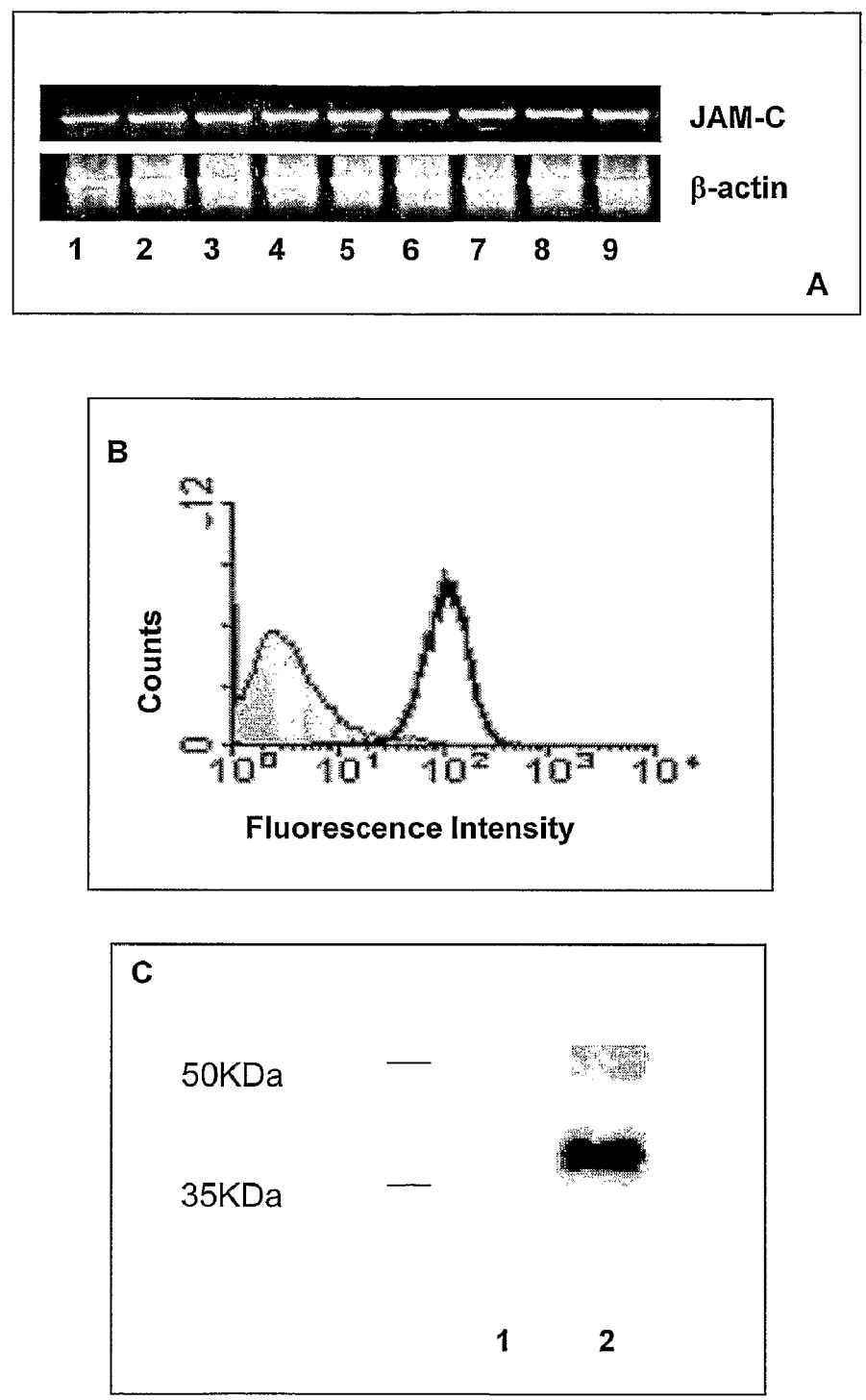
FIG. 1: JAM-C expression in human gliomas. A. RT-PCR for human JAM-C on glioma cell lines. Lanes 1, 6, 8: astrocytomas (grade III) Ge182, Ge299, Ge328 respectively, lanes 2, 3, 4, 5, 9: glioblastomas Ge224, Ge242, Ge258, Ge285, Ge360, respectively, lane 7: oligoastrocytoma Ge314. B. Cytofluorimetric analysis of JAM-C expression on Ge258 human glioblastoma cells. The histogram shows the profile obtained with the anti-JAM-C monoclonal antibody (black open curve) and the isotype control antibody (gray-filled curve). C. Immunoprecipitation of human JAM-C in Ge258 human glioblastoma cells. Lane 1: pre-immune rabbit serum, lane 2: polyclonal anti-human JAM-C.

The first aspect of the instant invention relates to use of a compound that specifically binds to JAM-C for the treatment of glioma.

The first embodiment of the first aspect of the invention is the use of a compound that specifically binds to JAM-C for the treatment of glioma.

The second embodiment of the first aspect of the invention is the use according to the first embodiment of the first aspect of the invention, wherein the compound is an antagonist of JAM-C.

The third embodiment of the first aspect of the invention is the use according to the second embodiment of the first aspect of the invention, wherein the antagonist inhibits the interaction of JAM-C with JAM-B.

The fourth embodiment of the first aspect of the invention is the use according to the first, second or third embodiment of the first aspect of the invention, wherein the compound is an antibody or antigen binding fragment thereof specifically binding to JAM-C.

The fifth embodiment of the first aspect of the invention is the use according to the fourth embodiment of the first aspect of the invention, wherein the antibody or antigen binding fragment thereof that specifically binds to JAM-C exhibits an avidity effect.

The sixth embodiment of the first aspect of the invention is the use according to the fourth embodiment of the first aspect of the invention, wherein the antibody or antigen binding fragment thereof that specifically binds to JAM-C has a dissociation constant $k_d$ of $\geq 10^{-4}$ s$^{-1}$, preferably $\geq 10^{-2}$ s$^{-1}$ and more preferably $\geq 5 \times 10^{-2}$ s$^{-1}$ as determined by surface plasmon resonance using solid phase bound JAM-C and said anti-JAM-C antibody as analyte.

The seventh embodiment of the first aspect of the invention is the use according to the fourth or fifth embodiment of the first aspect of the invention, wherein the antibody is the rat monoclonal antibody D33 that is produced by the hybridoma cell line that has been deposited at the European Collection of Cell Cultures (ECACC) under accession no. 06092701; or a humanized or primatized variant thereof; or a fragment comprising the antigen binding region thereof.

The eighth embodiment of the first aspect of the invention is the use according to the first, second, third, fourth, fifth, sixth or seventh embodiment of the first aspect of the invention, wherein the compound, antagonist, antibody or antigen binding fragment of an antibody is linked to a cytotoxic agent such as a toxin, a radionuclide or a cytokine.

The nineth embodiment of the first aspect of the invention is the use according to the first, second, third, fourth, fifth, sixth, seventh or eighth embodiment of the first aspect of the invention, wherein the glioma is an astrocytoma.

The tenth embodiment of the first aspect of the invention is the use according to the nineth embodiment of the first aspect of the invention, wherein the astrocytoma is of grade I, grade II or grade III.

The eleventh embodiment of the first aspect of the invention is the use according to the nineth embodiment of the first aspect of the invention, wherein the astrocytoma is a glioblastoma.

The twelfth embodiment of the first aspect of the invention is the use according to the eleventh embodiment of the first aspect of the invention, wherein the glioblastoma is characterized in that the mRNA expression of at least 1, 2, 3, 4, 5, 6, 7, 8, 9 or 10 of the genes selected from the group consisting of Fos, FosL2, PAK3, Tspan6, PVR, BDNF, RapGEF2, Ptgfrn, AFAP and Eps8 is upregulated as compared to the mRNA expression in non-tumour astrocytes.

The thirteenth embodiment of the first aspect of the invention is the use according to the first, second, third, fourth, fifth, sixth, seventh, eighth, nineth, tenth, eleventh or twelfth embodiment of the first aspect of the invention, wherein the glioma has spread.

The fourteenth embodiment of the first aspect of the invention is the use according to the thirteenth embodiment of the first aspect of the invention, wherein the glioma has metastasized.

The fifteenth embodiment of the first aspect of the invention is the use according to the first, second, third, fourth, fifth, sixth, seventh, eighth, ninth, tenth, eleventh, twelfth, thirteenth or fourteenth embodiment of the first aspect of the invention, wherein the compound is administered systemically.

The invention also relates a method for treating a patient with glioma comprising administering to the patient an effective amount of a compound that specifically binds to JAM-C, whereby the glioma ameliorates.

In a preferred embodiment, the glioma patient is a human or a domestic animal such a dog or a cat. The patient may have an astrocytoma. Astrocytomas may be of any grade including but not limited to, pilocytic astrocytomas (grade I), diffuse astrocytomas (grade II), anaplastic astrocytomas (grade III) and glioblastomas (grade IV).

The invention also relates a method for treating a patient with glioma according to any one of the methods described supra, wherein the compound binding specifically to JAM-C, or the anti-JAM-C antibody is administered systemically.

The second aspect of the instant invention thus relates to use of an antibody or antigen binding fragment thereof that specifically binds to JAM-C for the inhibition of the growth of glioma or the spreading of glioma.

The first embodiment of the second aspect of the invention is the use of an antibody or antigen binding fragment thereof that specifically binds to JAM-C for the inhibition of the growth of glioma.

The second embodiment of the second aspect of the invention is the use of an antibody or antigen binding fragment thereof that specifically binds to JAM-C for the inhibition of glioma spreading.

The third embodiment of the second aspect of the invention is the use according to the first or second embodiment of the second aspect of the invention, wherein the antibody inhibits the interaction of JAM-C with JAM-B.

The fourth embodiment of the second aspect of the invention is the use according to the first, second or third embodiment of the second aspect of the invention, wherein the antibody or antigen binding fragment thereof that specifically binds to JAM-C exhibits an avidity effect.

The fifth embodiment of the second aspect of the invention is the use according to the first, second or third embodiment of the second aspect of the invention, wherein the antibody or antigen binding fragment thereof that specifically binds to JAM-C has a dissociation constant $k_d$ of $\geq 10^{-4}$ s$^{-1}$, preferably $\geq 10^{-2}$ s$^{-1}$ and more preferably $\geq 5 \times 10^{-2}$ s$^{-1}$ as determined by surface plasmon resonance using solid phase bound JAM-C and said anti-JAM-C antibody as analyte.

The sixth embodiment of the second aspect of the invention is the use according to the first, second, third or fourth embodiment of the second aspect of the invention, wherein the antibody is the rat monoclonal antibody D33 that is produced by the hybridoma cell line that has been deposited at the European Collection of Cell Cultures (ECACC) under accession no. 06092701; or a humanized or primatized variant thereof; or a fragment comprising antigen binding region thereof.

The seventh embodiment of the second aspect of the invention is the use according to the first, second, third, fourth, fifth or sixth embodiment of the second aspect of the invention, wherein the antibody is linked to a cytotoxic agent such as a toxin, a radionuclide or a cytokine.

The eighth embodiment of the second aspect of the invention is the use according to the first, second, third, fourth, fifth, sixth or seventh embodiment of the second aspect of the invention, wherein the glioma is an astrocytoma.

The nineth embodiment of the second aspect of the invention is the use according to the eighth embodiment of the second aspect of the invention, wherein the astrocytoma is of grade I, grade II or grade III.

The tenth embodiment of the second aspect of the invention is the use according to the eighth embodiment of the second aspect of the invention, wherein the astrocytoma is a glioblastoma.

The eleventh embodiment of the second aspect of the invention is the use according to the first, second, third, fourth, fifth, sixth, seventh, eighth, nineth or tenth embodiment of the second aspect of the invention, wherein the glioma has spread.

The twelfth embodiment of the second aspect of the invention is the use according to the eleventh embodiment of the second aspect of the invention, wherein the glioma has metastasized.

The thirteenth embodiment of the second aspect of the invention is the use according to the first, second, third, fourth, fifth, sixth, seventh, eighth, nineth, tenth, eleventh or twelfth embodiment of the second aspect of the invention, wherein the antibody or antigen binding fragment thereof is administered systemically.

The third aspect of the instant invention relates to use of a compound that specifically binds to JAM-B for the treatment of glioma.

The first embodiment of the third aspect of the invention is the use of a compound that specifically binds to JAM-B for the treatment of glioma.

The second embodiment of the third aspect of the invention is the use according to the first embodiment of the third aspect of the invention, wherein the compound is an antagonist of JAM-B.

The third embodiment of the third aspect of the invention is the use according to the second embodiment of the third aspect of the invention, wherein the antagonist inhibits the interaction of JAM-B with JAM-C.

The fourth embodiment of the third aspect of the invention is the use according to the first, second or third embodiment of the third aspect of the invention, wherein the compound is an antibody or antigen binding fragment thereof specifically binding to JAM-B.

The fifth embodiment of the third aspect of the invention is the use according to the fourth embodiment of the third aspect of the invention, wherein the antibody or antigen binding fragment thereof that specifically binds to JAM-B exhibits an avidity effect.

The sixth embodiment of the third aspect of the invention is the use according to the fourth embodiment of the third aspect of the invention, wherein the antibody or antigen binding fragment thereof that specifically binds to JAM-B has a dissociation constant $k_d$ of $\geq 10^{-4}$ s$^{-1}$, preferably $\geq 10^{-2}$ s$^{-1}$ and more preferably ≧5×10$^{-2}$ s$^{-1}$ as determined by surface plasmon resonance using solid phase bound JAM-B and said anti-JAM-B antibody as analyte.

The seventh embodiment of the third aspect of the invention is the use according to the first, second, third, fourth, fifth or sixth embodiment of the third aspect of the invention, wherein the compound, antagonist, antibody or antigen binding fragment of an antibody is linked to a cytotoxic agent such as a toxin, a radionuclide or a cytokine.

The eighth embodiment of the third aspect of the invention is the use according to the first, second, third, fourth, fifth, sixth or seventh embodiment of the third aspect of the invention, wherein the glioma is an astrocytoma.

The nineth embodiment of the third aspect of the invention is the use according to the eighth embodiment of the third aspect of the invention, wherein the astrocytoma is of grade I, grade II or grade III.

The tenth embodiment of the third aspect of the invention is the use according to the eighth embodiment of the third aspect of the invention, wherein the astrocytoma is a glioblastoma.

The eleventh embodiment of the third aspect of the invention is the use according to the tenth embodiment of the third aspect of the invention wherein the glioblastoma is characterized in that the mRNA expression of at least 1, 2, 3, 4, 5, 6, 7, 8, 9 or 10 of the genes selected from the group consisting of Fos, FosL2, PAK3, Tspan6, PVR, BDNF, RapGEF2, Ptgfrn, AFAP and Eps8 is upregulated as compared to the mRNA expression in non-tumour astrocytes.

The twelfth embodiment of the third aspect of the invention is the use according to the first, second, third, fourth, fifth, sixth, seventh, eighth, nineth, tenth or eleventh embodiment of the third aspect of the invention, wherein the glioma has spread.

The thirteenth embodiment of the third aspect of the invention is the use according to the twelfth embodiment of the third aspect of the invention, wherein the glioma has metastasized.

The fourteenth embodiment of the third aspect of the invention is the use according to the first, second, third, fourth, fifth, sixth, seventh, eighth, nineth, tenth, eleventh, twelfth or thirteenth embodiment of the third aspect of the invention, wherein the compound is administered systemically.

The invention also relates a method for treating a patient with glioma comprising administering to the patient an effective amount of a compound that specifically binds to JAM-B, whereby the glioma ameliorates.

In a preferred embodiment, the glioma patient is a human or a domestic animal such a dog or a cat. The patient may have an astrocytoma. Astrocytomas may be of any grade including but not limited to, pilocytic astrocytomas (grade I), diffuse astrocytomas (grade II), anaplastic astrocytomas (grade III) and glioblastomas (grade IV).

The invention also relates a method for treating a patient with glioma according to any one of the methods described supra, wherein the compound binding specifically to JAM-C, or the anti-JAM-C antibody is administered systemically.

A fourth aspect of the invention is the use according to any of the embodiments of the first, second or third aspects of the invention, wherein the compound that specifically binds to JAM-B and the compound that specifically binds to JAM-C are used in combination.

The first embodiment of the fourth aspect of the invention is the use of a compound that specifically binds to JAM-B and a compound that specifically binds to JAM-C in combination for the treatment of glioma.

The second embodiment of the fourth aspect of the invention is the use according to the first embodiment of the fourth aspect of the invention, wherein at least one of the compounds is an antagonist of JAM-B, or an antagonist of JAM-C.

The third embodiment of the fourth aspect of the invention is the use according to the second embodiment of the fourth aspect of the invention, wherein one compound is an antagonist of JAM-B and one compound is an antagonist of JAM-C.

The fourth embodiment of the fourth aspect of the invention is the use according to the second or third embodiment of the fourth aspect of the invention, wherein the at least one of the antagonists inhibits the interaction of JAM-B with JAM-C.

The fifth embodiment of the fourth aspect of the invention is the use according to the first, second, third or fourth embodiment of the fourth aspect of the invention, wherein at least one of the compounds is an antibody or antigen binding fragment thereof specifically binding to JAM-B or to JAM-C.

The sixth embodiment of the fourth aspect of the invention is the use according to the first, second, third, fourth or fifth embodiment of the fourth aspect of the invention, wherein at least one of the compounds, antagonists, antibodies or antigen binding fragments of an antibody is linked to a cytotoxic agent such as a toxin, a radionuclide or a cytokine.

The seventh embodiment of the fourth aspect of the invention is the use according to the first, second, third, fourth, fifth or sixth embodiment of the fourth aspect of the invention, wherein the glioma is an astrocytoma.

The eighth embodiment of the fourth aspect of the invention is the use according to the seventh embodiment of the fourth aspect of the invention, wherein the astrocytoma is of grade I, grade II or grade III.

The nineth embodiment of the fourth aspect of the invention is the use according to the seventh embodiment of the fourth aspect of the invention, wherein the astrocytoma is a glioblastoma.

The tenth embodiment of the fourth aspect of the invention is the use according to the nineth embodiment of the fourth aspect of the invention, wherein the glioblastoma is characterized in that the mRNA expression of at least 1, 2, 3, 4, 5, 6, 7, 8, 9 or 10 of the genes selected from the group consisting of Fos, FosL2, PAK3, Tspan6, PVR, BDNF, RapGEF2, Ptgfrn, AFAP and Eps8 is upregulated as compared to the mRNA expression in non-tumour astrocytes.

The eleventh embodiment of the fourth aspect of the invention is the use according to the first, second, third, fourth, fifth, sixth, seventh, eighth, nineth or tenth embodiment of the fourth aspect of the invention, wherein the glioma has spread.

The twelfth, embodiment of the fourth aspect of the invention is the use according to the eleventh embodiment of the fourth aspect of the invention, wherein the glioma has metastasized.

The thirteenth embodiment of the fourth aspect of the invention is the use according to the first, second, third, fourth, fifth, sixth, seventh, eighth, ninth, tenth, eleventh or twelfth embodiment of the fourth aspect of the invention, wherein at least one of the compounds is administered systemically.

A fifth aspect of the invention is the rat monoclonal antibody D33, which specifically binds to JAM-C and is produced by the hybridoma cell line that has been deposited at the European Collection of Cell Cultures (ECACC) under accession no. 06092701.

The first embodiment of the fifth aspect of the invention is the rat monoclonal antibody D33 produced by the hybridoma cell line that has been deposited at the European Collection of Cell Cultures (ECACC) under accession no. 06092701.

The second embodiment of the fifth aspect of the invention is the hybridoma cell line that has been deposited at the European Collection of Cell Cultures (ECACC) under accession no. 06092701, which produces the antibody D33.

The third embodiment of the fifth aspect of the invention is an antibody comprising the antigen binding region of the rat monoclonal antibody D33 produced by the hybridoma cell line that has been deposited at the European Collection of Cell Cultures (ECACC) under accession no. 06092701.

The fourth embodiment of the fifth aspect of the invention is a humanized or primatized form of the rat monoclonal antibody D33 produced by the hybridoma cell line that has been deposited at the European Collection of Cell Cultures (ECACC) under accession no. 06092701. In the humanized antibody at least part of the rodent antibody sequences are replaced with sequences from a human equivalent antibody. For instance, the constant region of monoclonal antibody D33 may be replaced with the sequences from a human immunoglobulin molecule. In a primatized antibody the rodent antibody sequences are replaced with suitable primate antibody sequences in an analogous manner.

In the fifth embodiment of the fifth aspect the invention provides a recombinant antibody comprising the antigen binding regions of monoclonal antibody D33, wherein the antibody has been modified to optimize expression or compatibility with the human immune system. For example, an antibody of the invention may be a single chain antibody. Such antibodies may be produced in large quantities in bacterial cells and efficiently purified as a single polypeptide.

The sixth embodiment of the fifth aspect the invention is an antibody according to the first, third, fourth of fifth embodiment of the fifth aspect of the invention for use as a medicament.

The seventh embodiment of the fifth aspect of the invention is a pharmaceutical composition comprising the antibody according to the first, third, fourth or fifth embodiment of the fifth aspect of the invention, optionally together with a pharmaceutically acceptable carrier or excipient.

The term "antagonist" or "antagonists" as used herein refers to a binding partner (ligand) of a target molecule, which ligand inhibits or reduces at least one biological activity of said target molecule.

The term "antagonist of JAM-C" or "antagonists of JAM-C" as used herein refers to a compound that binds to and inhibits at least one biological activity of JAM-C. The term "antagonist of JAM-B" or "antagonists of JAM-B" is used herein in analogous manner. Biological activities of JAM-C are known in the art and include but are not limited to the homophilic binding to JAM-C and the heterophilic binding to JAM-B. Biological activities of JAM-B are known in the art and include but are not limited to the homophilic binding to JAM-B and the heterophilic binding to JAM-C. "Antagonists of JAM-B or JAM-C" are for example proteins that inhibit at least one biological activity of JAM-B or JAM-C, respectively, such as for example antibodies, or other protein or polypeptide compounds comprising more than 10 amino acids that are based on protein scaffolds e.g. from lipocalin ("anticalins"), fibronectin ("adnectins", trinectins), kunitz domains, C-type lectin, transferrin, gamma-crystalline, cysteine-nots, ankyrin repeats ("DARPins") or protein A ("affibodies") as known in the art (Tomlinson, 2004; Mosavi et al., 2004; Gill and Damle, 2006; Nilsson and Tolmachev, 2007; Binz et at, 2004). "Antagonists of JAM-B or JAM-C" include also small molecular weight compounds that inhibit at least one biological activity of JAM-B or JAM-C, respectively, such as for example, organic molecules, other than polypeptides comprising more than 10 amino acids, but including peptides and cyclic peptides comprising not more than 10 amino acids as well as peptidomimetics. Peptidomimetics are compounds that are based on the amino acid sequences found at protein-protein interaction sites and are known in the art (Sillerud and Larson, 005).

The term "spreading" of the tumour (e.g. the glioma) as used herein refers (a) to the transfer of the tumour (e.g. glioma) from one part of the organ (e.g. the brain) to another part, which is also referred to as infiltration or invasion, and (b) to the transfer of the tumour (e.g. glioma) from one organ to another organ not directly connected with it, which is also referred to as metastasis. The spreading of the tumour (e.g. glioma) can e.g. occur from the primary tumour to one or more secondary sites (e.g. in the brain), or from a secondary site to one or more tertiary sites (e.g. in the brain).

The term "antibody" or "antibodies" as used herein refers to monoclonal or polyclonal antibodies. The term immunoglobulin is used synonymously with antibody. The term "antibody" or "antibodies" as used herein includes but is not limited to recombinant antibodies that are generated by recombinant technologies as known in the art. "Antibody" or "antibodies" include antibodies of any species, in particular of mammalian species; such as human antibodies; non-human primate antibodies, e.g. from chimpanzee, baboon, rhesus or cynomolgus monkey; rodent antibodies, e.g. from mouse, rat or rabbit; goat or horse antibodies; and camelid antibodies; or of bird species such as chicken antibodies or of fish species such as shark antibodies.

The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences.

"Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human disease. Humanized antibodies and several different technologies to generate them are well known in the art (Hwang et al., 2005a; Damschroder et al., 2007; Lazar et al., 2007; Nishibori et al., 2006; Tsurushita et al., 2005; Dall'Acqua et al., 2005; Hwang et al., 2005b; Kashmiri et al., 2005; Gonzales et al., 2004; Lo, 2004; O'Brien and Jones, 2003).

The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art (Lonberg, 2005; Green, 1999; Kellermann and Green, 2002; Nicholson et al., 1999). Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody.

Other methods for obtaining human antibodies antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art (Winter et al., 1994; Hoogenboom, 2002; Kretzschmar and von Ruden, 2002; Groves and Osbourn, 2005; Dufner et al., 2006).

Human antibodies may also be generated from isolated human B cells that are ex-vivo immunized with an antigen of interest and subsequently fused to generate hybridomas which can then be screened for the optimal human antibody (Grasso et al., 2004; Li et al., 2006).

The term "monoclonal antibody" as used herein refers to a composition of a plurality of individual antibody molecules, wherein each individual antibody molecule is identical at least in the primary amino acid sequence of the heavy and light chains. For the most part, "monoclonal antibodies" are produced by a plurality of cells and are encoded in said cells by the identical combination of immunoglobulin genes. Generally "monoclonal antibodies" are produced by cells that harbor antibody genes, which are derived from a single ancestor B cell.

"Polyclonal antibody" or "polyclonal antibodies", in contrast, refers to a composition of a plurality of individual antibody molecules, wherein the individual antibody molecules are not identical in the primary amino acid sequence of the heavy or light chains. For the most part, "polyclonal antibodies" bind to the same antigen but not necessarily to the same part of the antigen; i.e. antigenic determinant (epitope). Generally, "polyclonal antibodies" are produced by a plurality of cells and are encoded by at least two different combinations of antibody genes in said cells.

The term "antibody fragment" or "antibody fragments" as used herein refers to a portion of an intact antibody that consists of two complete heavy and two complete light chains, preferably comprising the antigen binding region thereof. Examples of antibody fragments according to the invention include Fab, Fab', F(ab')$_2$, and Fv and scFv fragments; as well as diabodies; triabodies; tetrabodies; minibodies; domain antibodies; single-chain antibodies; bispecific, trispecific, tetraspecific or multispecific antibodies formed from antibody fragments or antibodies. Antibody fragments as defined above are known in the art (Holliger and Hudson, 2005).

As used herein the term "antigen binding domain" refers the antibody variable domain that undergoes rearrangement in antibody producing cells (e.g. B-cells or hybridoma cells) and directly interacts with the antibodies' target antigen, in this case JAM-C. Thus, an antibody comprising the antigen binding region of the monoclonal antibody D33 may comprise any isotype. For instance, an antibody according to the invention may be an IgA, IgM, IgE or IgG antibody. Furthermore, the term antibody also includes antibody fragments such as Fab, F(ab')$_2$, single domain antibodies or antibody paratope peptides. Antibodies for use in the current invention may be produced in animals and harvested as ascites fluid. However, in a preferred embodiment, an antibody comprising an antigen binding region of monoclonal antibody D33 are produced in mammalian cells (e.g., in a bioreactor) or in insect, yeast or bacterial cells.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

The term "Fc region" herein is used to define a C-terminal region of an immunoglobulin heavy chain, including native sequence Fc regions and variant Fc regions. The Fc fragment consists of $CH_2$, $CH_3$, and part of the hinge region. Although the boundaries of the Fc region of an immunoglobulin heavy chain might vary, the human IgG heavy chain Fc region is usually defined to stretch from an amino acid residue at position Cys-226, or from Pro-230, to the carboxyl-terminus thereof. In human IgG molecules, the Fc fragment is generated by papain cleavage of the hinge region N-terminal to Cys-226. Therefore, the human IgG heavy chain Fc region is usually defined as stretching from the amino acid residue at position 226 to the C-terminus. The above numbering is according to Kabat (Kabat, 1988), who had based it on the sequence of a myeloma protein later identified as the immunoglobulin EU (Edelman et al., 1969).

"Fv" is the minimum antibody fragment that comprises a complete antigen-recognition and antigen-binding site. This region consists of a dimer of one heavy chain and one light chain variable domain in tight, non-covalent association. In an "scFV" molecule the heavy chain variable domain is covalently bound to the light chain variable domain via a linker. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also comprises the constant domain of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The term "avidity effect" refers to an increase in affinity of multivalent binding of a first molecule to a second molecule as compared to monovalent binding of the same first molecule to the same second molecule. An antibody may show an avidity effect; i.e. the affinity is higher when both arms of the y-shaped antibody bind to the target antigen (bivalent binding) as compared to when only one arm of the y-shaped antibody binds to the target antigen (monovalent binding). An "avidity effect" of an antibody or antigen binding fragment thereof that specifically binds to JAM-C can be determined e.g. by measuring the (bivalent) binding affinity of the antibody that specifically binds to JAM-C, or the bivalent antigen binding fragment thereof, to a glioma cell line (e.g. the human glioma cell line U-251, BT-325, U-373, A-172, M059K, M059J, LN-18 or Hs 683), measuring the (monovalent) binding affinity of a monovalent antigen binding fragment of said antibody, or the bivalent antigen binding fragment thereof, to the same glioma cell line, and comparing the binding affinities, wherein the antibody or antigen binding fragment thereof that specifically binds to JAM-C exhibits an avidity effect if the bivalent binding affinity is higher than the monovalent binding affinity.

Depending on the amino acid sequence of the constant domain of their "heavy chains," (if present) antibodies can be assigned to different classes. There are five major classes of intact antibodies: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy chain constant domains that correspond to the different classes of antibodies are called alpha, delta, epsilon, gamma, and mu, respectively. The subunit structures and three-dimensional configurations of different classes of immunoglobulins are well known in the art.

It is well known that the Fc region of an antibody mediates "effector functions", which include binding of the complement component C1q leading to complement dependent cytotoxicity (CDC); antibody-dependent cell-mediated cytotoxicity (ADCC); phagocytosis and down regulation of cell surface receptors (e.g. B cell receptor).

It may be desirable to modify the antagonist or antibody of the invention with respect to effector function, e.g. so as to enhance antigen-dependent cell-mediated cyotoxicity (ADCC) and/or complement dependent cytotoxicity (CDC) of the antagonist or antibody. This may be achieved by introducing one or more amino acid substitutions in an Fc region of an antibody antagonist or antibody as it is known in the art. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC).

It has also been recognized that the Fc region is critical for maintaining the serum half-life of an immunoglobulin of class G (IgG) (Ward and Ghetie, 1995). Studies have found that the serum half-life of an IgG is mediated by binding of Fc to the neonatal Fc receptor (FcRn). FcRn is a heterodimer consisting of a transmembrane a chain and a soluble β-chain (β$_2$-microglobulin). The α$_1$ and α$_2$ domains of FcRn interact with the CH$_2$ and CH$_3$ domains of the Fc region. The site on the Fc fragment of human IgG that interacts with FcRn has been mapped (Kim et al., 1999; Vaughn et al., 1997).

The correlation between the affinity for FcRn binding and the serum half-life of an immunoglobulin is well known in the art (Datta-Mannan et al., 2007b). Significantly, such a correlation has been extended to engineered antibodies with higher affinity for FcRn than their wild-type parent molecules. A large number of publications and patents based upon mutagenesis studies support this correlation (Ward and Ghetie, 1995; Ghetie et al., 1997; Dall'Acqua et al., 2002; Hinton et al., 2004; Hinton et al., 2006; Shields et al., 2001; Datta-Mannan et al., 2007a; Karnei et al., 2005).

The Fc region can also be used to achieve oral or pulmonary delivery of therapeutic proteins. Fc fusion proteins have been successfully delivered via these routes (Bitonti and Dumont, 2006; Bitonti et al., 2004; Low et al., 2005; Dumont et al., 2005).

A "native sequence Fc region" comprises an amino acid sequence identical to the amino acid sequence of an Fc region found in nature. Native sequence human Fc regions include a native sequence human IgG$_1$ Fc region (non-A and A allotypes); native sequence human IgG$_2$ Fc region; native sequence human IgG$_3$ Fc region; and native sequence human IgG$_4$ Fc region; as well as naturally occurring variants of any of the above. A "variant Fc region" comprises an amino acid sequence which differs from that of a native sequence.

The antagonist or antibody according to the invention is optionally conjugated to another agent, such as a cytotoxic agent (e.g. a toxin such as diphtheria toxin, maytansine, maytansinoid, doxorubicin, calicheamicin, ozogamicin, auristatin, a derivative of auristatin (e.g. monomethyl auristatin), *Pseudomonas* exotoxin, ricin, ricin A chain, brin, abrin, mistletoe lectin, modeccin, pokeweed antiviral protein, PAP, saporin, bryodin 1, bouganin, gelonin, or alpha-sarcin), a radionuclide (e.g. scandium-47, copper-64, copper-67, gallium-67, yttrium-90, yttrium-91, palladium-103, rhodium-105, indium-111, tin-117m, iodine-125, iodine-131, samarium-153, dysprosium-166, holmium-166, ytterbium-175, rhenium-186, rhenium-188, lutetium-177, iridium-192, osmium-194, gold-198 or bismuth-213) or a cytokine (for example IL-2 or TNF). The antagonist or antibody according to the invention may also be conjugated to therapeutic agents such as chemotherapeutic agents, therapeutic polypeptides, nanoparticles, liposomes or therapeutic nucleic acids, or to imaging agents such as enzymes, radionuclides or fluorophores. In one embodiment, the antagonist or antibody according to the invention is conjugated or linked to molecules that increase the serum half life of the antibody such as polyethylene glycol (PEG) chains.

Conjugation will ordinarily be achieved through a covalent linkage. Typically, a non-peptidic agent is modified by the addition of a linker that allows conjugation to the JAM-B or JAM-C antagonist or antibody through its amino acid side chains, carbohydrate chains, or reactive groups introduced on the JAM-B or JAM-C antagonist or antibody by chemical modification. For example, a drug may be attached through the ε-amino group of a lysine residue, through a free α-amino group, by disulfide exchange to a cysteine residue, or by oxidation of the 1,2-diols in a carbohydrate chain with periodic acid to allow attachment of drugs containing various nucleophiles through a Schiff-base linkage. Protein modifying agents include amine-reactive reagents (e.g., reactive esters, isothiocyantates, aldehydes, and sulfonyl halides), thiol-reactive reagents (e.g., haloacetyl derivatives and maleimides), and carboxylic acid-and aldehyde-reactive reagents. JAM-B or JAM-C antagonist or antibodies can be covalently joined to peptidic agents through the use of bifunctional cross-linking reagents. Heterobifunctional reagents are more commonly used and permit the controlled coupling of two different proteins through the use of two different reactive moieties (e.g., amine-reactive plus thiol, iodoacetamide, or maleimide). The use of such linking agents is well known in the art. Peptidic linkers can also be employed. In the alternative, a JAM-B or JAM-C antagonist or antibody can be linked to a peptidic moiety through preparation of a fusion polypeptide.

Examples of further bifunctional protein coupling agents include N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Alternatively, a fusion protein comprising the antagonist or antibody and the agent may be made, e.g. by recombinant techniques or peptide synthesis. Other modifications of the antagonist or antibody are contemplated herein. For example, the antagonist or antibody may be linked to one of a variety of nonproteinaceous polymers, e.g., polyethylene glycol, polypropylene glycol, polyoxyalkylenes, or copolymers of polyethylene glycol and polypropylene glycol.

The invention also contemplates that the antagonist or antibody that specifically binds to JAM-B or JAM-C is linked (e.g. in a fusion protein) to a peptide or protein in order to achieve receptor-mediated transport of said antagonist or antibody through the blood-brain barrier. Examples for such peptides and proteins are insulin, transferrin, the insulin-like growth factors and leptin.

The antagonist or antibody that specifically binds to JAM-B or JAM-C may also be coupled to liposomes in order to yield immunoliposomes as known in the art (Kontermann, 2006). Such immunoliposomes may comprise a cytoxic agent (e.g. a toxin, radionuclide or cytokine) as described supra.

Pharmaceutical formulations of the antagonist or antibody used in accordance with the present invention are prepared for storage by mixing an antagonist or antibody having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (not more than about 10 residues) peptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes {e.g. Zn-protein complexes); and/or non-ionic surfactants such as TWEEN, PLURONICS or polyethylene glycol (PEG).

The methods and uses of the invention further contemplate administration of a second therapeutic agent; i.e. a combination therapy with a compound that specifically binds to JAM-B or JAM-C, and e.g. an anti-CD20 antibody [e.g. rituximab, ibritumomab tiuxetan, ofatumumab, ocrelizumab, hA20 (IMMU-106)]; a compound that inhibits the activity or activation of the EGF-R pathway (e.g. cetuximab, panatimumab, zalutumumab, nimotuzumab, matuzumab, trastuzumab, pertuzumab, gefitinib, erlotinib, lapatinib, EKB-569, HKI-272, CI-1033, vandetanib or BIBW2992); a tyrosine kinase inhibitor (e.g. sorafenib, sutinib, imatinib, dasatinib, valatinib, sonitinib, ofimatinib, AEE788); an anti-angiogenic agent, such as thalidomide, lenalidomide, a VEGF or a VEGF-R (e.g. VEGF-R1, VEGF-R2) antagonist (e.g. bevacizumab, VEGF-trap, pegaptanib, vandetanib, vatalanib, cediranib, ranibizumab, aflibercept, enzastaurin, cediranib, SU-4984, SU-5402, PD-173074), a FGF (e.g. FGF1, FGF2, FGF-3, FGF4, FGF5, FGF6, FGF7, FGF84, FGF9, FGF10, FGF11, FGF12, FGF13, FGF14, FGF16, FGF17, FGF18, FGF19, FGF20, FGF21, FGF22, FGF23) or FGF-R (e.g. FGF-R1, FGF-R2, FGF-R3, FGF-R4) antagonist; an IL-8 antagonist (e.g. an anti-IL-8 antibody such as MDX018/Hu-Max-Inflam); procarbazine; mechlorethamine; cyclophosphamide; camptothecin; carmustine; ifosfamide; melphalan; chlorambucil; busulfan; dactinomycin; daunorubicin; doxorubicin; bleomycin; plicomycin; mitomycin; tamoxifen; raloxifene; an estrogen receptor binding agent; paclitaxel; gemcitabine; navelbine; a farnesyltransferase inhibitor (e.g. lonafarnib, tipifarnib); an inhibitor of mTOR (mammalian target of rapamycin) (e.g. sirolimus; temirolimus; everolimus, deforolimus); an integrin inhibitor (e.g. cilengitide, the monoclonal antibodies CNTO 95 and etaracizumab all blocking the $\alpha_v\beta_3$ integrin, or the monoclonal antibody volociximab blocking the $\alpha_5\beta_1$ integrin); an inhibitor of the poliovirus receptor (PVR/CD155/Necl-5); an inhibitor of the cytoskeleton (e.g. taxol, eleutherobin, colcimid, nocodazole, discodermolide, epithilone, ixabepilone, epothilone B, cemadotin, dolastin, rhizoxin, combretastatin, maytansine, monomethylauristatin E, or other auristatin derivatives, extramustine, cytochalasin, vincristin or coichicin); an inhibitor of protein disulfide isomerase; an MMP inhibitor; a c-SRC inhibitor (e.g. AP22408, AZD0530, AZM475271, BMS-354825, CGP77675, 17-AAG, PP2, SKI-606, SU6656, anilinoquinazolines, PD173952, PD173955, terphenylquinone or UCS15A); transplatinum; 5-fluorouracil; capecitabine; tegafur-uracil; bortezomib; gemcitabine; methotrexate; temozolomide; nitrosourea; cisplatin; carboplatin; satraplatin; vincristin; vinblastin; vindesine; bendamustine; ecteinascidin-743; netropsin; podophyllotoxin; etoposide; teniposide; lexitropsin; enediyne; duocarmycine; irinotecan; oxiplatin; edotecarin or an inhibitor of topoisomerase I or II (e.g. topotecan).

In another embodiment of the invention, articles of manufacture containing materials useful for the treatment of a glioma as described above are provided. In one aspect, the article of manufacture comprises (a) a container comprising an antagonist (e.g. an antibody) that specifically binds to JAM-B or JAM-C, optionally in a pharmaceutically acceptable carrier or diluent; and (b) a package insert with instructions for treating a glioma in a human subject. The package insert is on or associated with the container. Suitable containers include, for example, bottles, vials, syringes, etc. The containers may be formed from a variety of materials such as glass or plastic. The container holds or contains a composition that is effective for treating glioma and may have a sterile access port (for example the container may be an intravenous solution bag or a vial having a stopper pierceable by a hypodermic injection needle). At least one active agent in the composition is the antagonist or antibody specifically binding to JAM-B or JAM-C. The label or package insert indicates that the composition is used for treating a human subject eligible for treatment, e.g., one having glioma, including astrocytoma, with specific guidance regarding dosing amounts and intervals of antagonist or antibody and any other medicament being provided. The article of manufacture may further comprise an additional container comprising a pharmaceutically acceptable diluent buffer, such as bacteriostatic water for injection, phosphate-buffered saline, Ringer's solution, and/or dextrose solution. The article of manufacture may further include other materials desirable from a commercial and user standpoint, including other buffers, diluents, filters, needles, and syringes.

The article of manufacture herein optionally further comprises a container comprising a second medicament, wherein the antagonist or antibody specifically binding to JAM-B or JAM-C is a first medicament, and which article further comprises instructions on the package insert for treating the subject with the second medicament, in an effective amount. The second medicament may be another monoclonal antibody such as an anti-CD20 antibody [e.g. rituximab, ibritumomab tiuxetan, ofatumumab, ocrelizumab, hA20 (IMMU-106)]; a compound that inhibits the activity or activation of the EGF-R pathway (e.g. cetuximab, panatimumab, zalutumumab, nimotuzumab, matuzumab, trastuzumab, pertuzumab, gefitinib, erlotinib, lapatinib, EKB-569, HKI-272, CI-1033, vandetanib or BIBW2992); a tyrosine kinase inhibitor (e.g. sorafenib, sutinib, imatinib, dasatinib, valatinib, sonitinib, ofimatinib, AEE788); an anti-angiogenic agent, such as thalidomide, lenalidomide, a VEGF or a VEGF-R antagonist (e.g. VEGF-R1, VEGF-R2) (e.g. bevacizumab, VEGF-trap, pegaptanib, vandetanib, vatalanib, cediranib, ranibizumab, aflibercept, enzastaurin, cediranib, SU-4984, SU-5402, PD-173074), a FGF (e.g. FGF1, FGF2, FGF-3, FGF4, FGF5, FGF6, FGF7, FGF84, FGF9, FGF10, FGF11, FGF12, FGF13, FGF14, FGF16, FGF17, FGF18, FGF19, FGF20, FGF21, FGF22, FGF23) or FGF-R (e.g. FGF-R1, FGF-R2, FGF-R3, FGF-R4) antagonist; an IL-8 antagonist (e.g. an anti-IL-8 antibody such as MDX018/HuMax-Inflam); procarbazine; mechlorethamine; cyclophosphamide; camptothecin; carmustine; ifosfamide; melphalan; chlorambucil; busulfan; dactinomycin; daunorubicin; doxorubicin; bleomycin; plicomycin; mitomycin; tamoxifen; raloxifene; an estrogen receptor binding agent; paclitaxel; gemcitabine; navelbine; a farnesyltransferase inhibitor (e.g. lonafarnib, tipifarnib); an inhibitor of mTOR (mammalian target of rapamycin) (e.g. sirolimus; temirolimus; everolimus, deforolimus); an integrin inhibitor (e.g. cilengitide, the monoclonal antibodies CNTO 95 and etaracizumab all blocking the $\alpha_v\beta_3$ integrin, or the monoclonal antibody volociximab blocking the $\alpha_5\beta_1$ integrin); an inhibitor of the poliovirus receptor (PVR/CD155/Necl-5); an inhibitor of the cytoskeleton (e.g. taxol, eleutherobin, colcimid, nocodazole, discodermolide, epithilone, ixabepilone, epothilone B, cemadotin, dolastin, rhizoxin, combretastatin, maytansine, monomethylauristatin E, or other auristatin derivatives, extramustine, cytochalasin, vincristin or colchicin); an inhibitor of protein disulfide isomerase; an MMP inhibitor; a c-SRC inhibitor (e.g. AP22408, AZD0530, AZM475271, BMS-354825, CGP77675, 17-MG, PP2, SKI-606, SU6656, anilinoquinazolines, PD173952, PD173955, terphenylquinone or UCS15A); transplatinum; 5-fluorouracil; capecitabine; tegafur-uracil; bortezomib; gemcitabine; methotrexate; temozolomide; nitrosourea; cisplatin; carboplatin; satraplatin; vincristin; vinblastin; vindesine; bendamustine; ectein-ascidin-743; netropsin; podophyllotoxin; etoposide; teniposide; lexitropsin; enediyne; duocarmycine; irinotecan; oxiplatin; edotecarin or an inhibitor of topoisomerase I or II (e.g. topotecan).

The methods and uses according to the contemplate systemic or local administration of a compound that specifically bind to JAM-C or JAM-B, such as antibodies that bind specifically to JAM-C or JAM-B, or the pharmaceutical composition according to the invention to an individual. One highly advantageous aspect of the antibodies of the invention is their ability to diffuse into tissues. For instance, the antibodies may traverse the blood brain barrier thereby enabling methods of administration via a variety of systemic routes.

Systemic administration is, for example, achieved by administration through the digestive tract (enteral administration) or through other routes (parenteral administration). Parenteral administration routes are, for example, intravenous, intraarterial, subcutaneous, transdermal, intradermal, intramuscular, intraperitoneal, nasal, intracranial, intrathecal, intracardiac, intraosseous or transmucosal routes. Enteral administration routes are, for example, oral, rectal, sublingual, or buccal routes.

Local administration is achieved, for example, through topical, epidural, epicutaneous, inhalational, nasal, intraarticular, vaginal, auricular or intravitreal routes. Local administration is also achieved by intracranial or intratumoral injection.

The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

The optimal dose of the pharmaceutical composition may be appropriately selected according to the route of administration, patient conditions and characteristics (sex, age, body weight, health, size), extent of symptoms, concurrent treatments, frequency of treatment and the effect desired. Adjustment and manipulation of established dosage ranges are well within the ability of those skilled. Any other therapeutically efficacious route of administration can be used, for example absorption through epithelial or endothelial tissues. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active ingredient can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The therapeutically effective amounts of the active ingredient will be a function of many variables, including but without limitation, the route of administration, the clinical condition of the patient, the pharmacokinetics of the active ingredient in a patient.

A "therapeutically effective amount" is amount of a polypeptide according to any of the embodiments of the invention that when administered to a patient in need of treatment with said polypeptide, such as e.g. a patient suffering from a from glioma such as astrocytoma, the amount of said polypeptide results in an improvement of the disorder in that patient vis-à-vis a patient who did not receive a therapeutically effective amount of said polypeptide. An improvement of the disorder can be measured by methods known in the art, the methods including the measurement of laboratory parameters taken from blood, urine, synovial fluid or cerebrospinal fluid, or other body fluids, the measurement of the functional status, pain or disability of the patient; the methods also including imaging such as magnetic resonance imaging (MRI) or X-ray.

The dosage administered, as single or multiple doses, to an individual will vary depending upon a variety of factors, including pharmacokinetic properties of a polypeptide according to any of the embodiments of the invention, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the effect of said polypeptide in an individual.

The invention contemplates the use of a compound, an antagonist or an antibody according to any of the embodiments of the invention in an amount in the range of 0.01 to 100 mg/kg or 0.01 to 10 mg/kg or body weight, or 0.1 to 5 mg/kg of body weight, or 1 to 10 mg/kg of body weight, or 1 to 3 mg/kg of body weight, or 2 mg/kg of body weight, or 5 mg/kg of body weight.

The invention further contemplates the administration of a compound, an antagonist or an antibody according to any of the embodiments of the invention to a patient daily or every other day or three times per week, once per week, every other week, once per month, every 6 weeks, every other month, 3 times per year, 2 times per year or once per year, at similar doses, or at doses increasing or decreasing with the time.

Second or subsequent administrations can be performed at a dosage which is the same, less than or greater than the initial or previous dose administered to the individual. In a preferred embodiment the compound, antagonist or antibody according to any of the embodiments of the invention is administered at a first dose and one or more subsequent higher dose(s).

Embodiments discussed in the context of the methods, uses and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

EXAMPLES

Example 1

JAM-C and JAM-B Expression in Human Gliomas

Results
JAM-C

By RT-PCR analysis, we first observed JAM-C mRNA expression in a series of human astrocytoma/glioma cell lines of different malignant grade (FIG. 1 A). All glioma cell lines analysed did express JAM-C mRNA. The expression of JAM-C protein by tumour cells was then confirmed by flow cytometry analysis (FACS) and immunoprecipitation of selected glioma cell lines (FIGS. 1 B and C).

Figure 2:
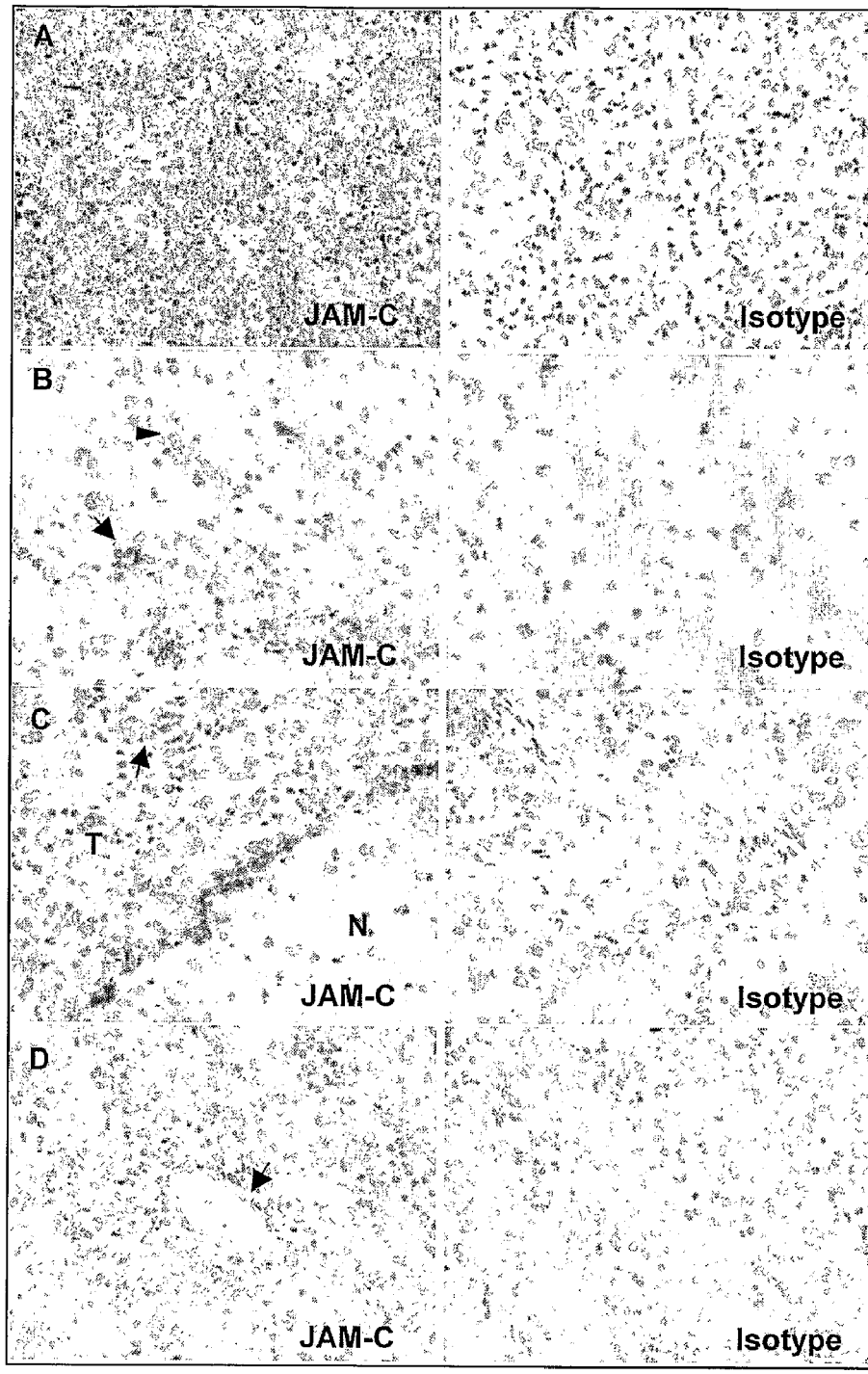
FIG. 2: Heterogeneous expression of JAM-C in human astrocytomas. A Ge 258 glioblastoma showing strong JAM-C expression on the great majority of tumour cells. B Ge 280 astrocytoma (grade III), single isolated tumour cells express high levels of JAM-C (indicated by an arrowhead), the arrow indicates a positive blood vessel. C Ge 305 glioblastoma where strong immunoreactivity for JAM-C is detected at the tumour margin with the normal brain. The arrow indicates a positive blood vessel, (T: tumour, N: normal brain). D Ge 299 astrocytoma (grade III) showing uniform JAM-C expression on all tumour cells. The arrow indicates a stained blood vessel. (Magnification: A 20×, B 20×, C 20×, D 20×).

Then JAM-C expression was assessed by immunohistochemistry on a series of human astrocytomas/gliomas of different grade of malignancy (N=21) (FIG. 2). JAM-C expression, as expected, was detected in all tumour blood vessels (FIGS. 2 B and D) with high levels at points of endothelial cell contacts, a pattern that corresponded to previous descriptions of JAM-C localisation at sites of inter-endothelial cell junctions. In addition, JAM-C was found to be expressed also by glioma tumour cells. JAM-C expression on astrocytomas was heterogeneous, with cases of both low and high grade astrocytomas expressing high levels of JAM-C on single isolated cells (FIG. 2 B), and cases where the expression was very high on the great majority of tumour cells (FIG. 2 A).

Figure 3:
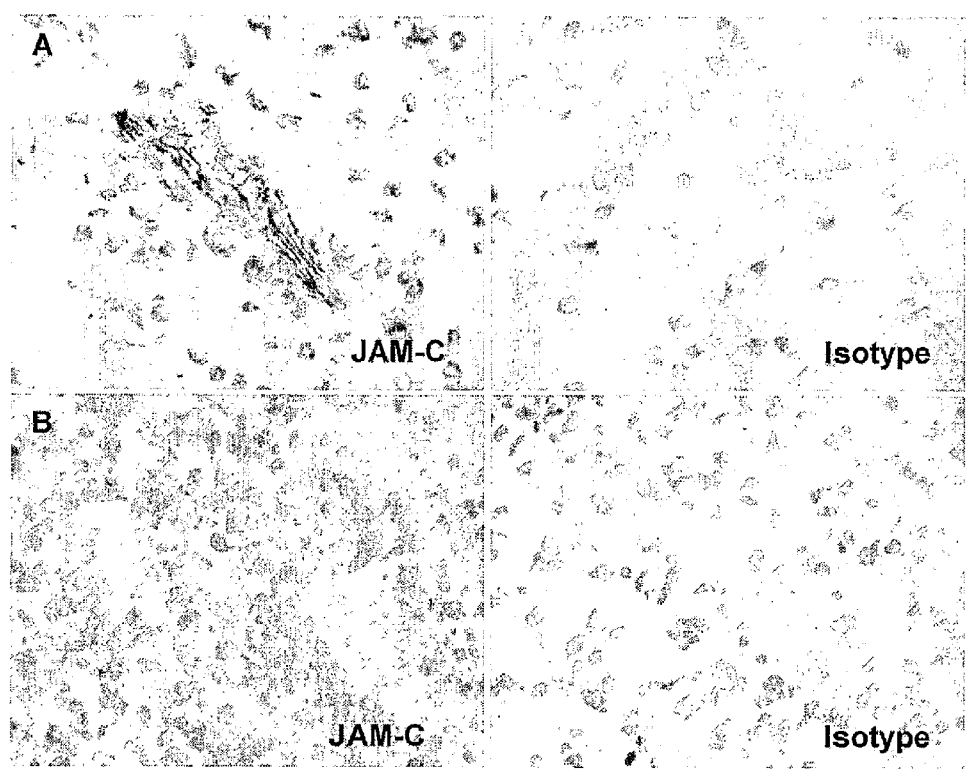
FIG. 3: Expression of JAM-C at sites of cell-cell contacts and intra-tumor heterogeneity. A. Ge262 astrocytoma (Grade II) showing high levels of JAM-C expression at points of cell-cell contacts. B. Ge258 glioblastoma showing cells expressing high levels of JAM-C intermingled with cells negative for JAM-C expression. (Magnifications: A 40×, B 40×).

The strongest levels of JAM-C expression were observed at sites of cell-cell contacts (FIG. 3 A) and lower levels were more uniformly distributed on cell membranes (FIG. 2 D). Interestingly, in one case strong expression of JAM-C was observed at the border between the tumour mass and the normal brain tissue (FIG. 2 C), the region corresponding to the invasive front of the tumour. Furthermore, a high heterogeneity in JAM-C expression was also observed in different regions of the same tumour sample, with highly JAM-C expressing tumour cells intermingled with tumour cells where JAM-C expression appeared completely absent (FIG. 3 B).

Figure 4:
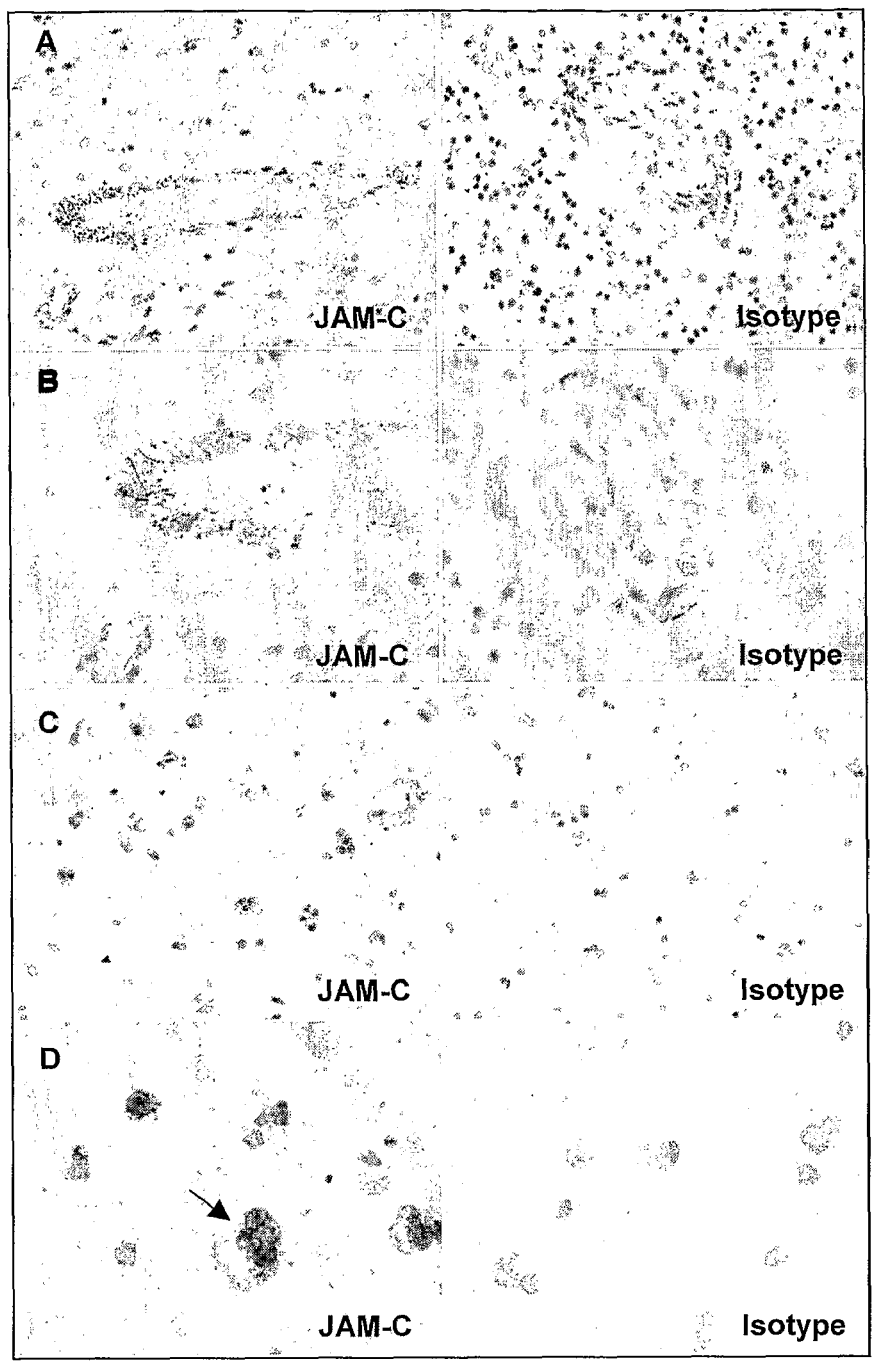
FIG. 4: In human non-tumoral brain (epilepsy biopsies) JAM-C is preferentially expressed by vascular endothelial cells and oligodendrocytes. A. Blood vessels showing strong JAM-C staining B. High levels of JAM-C expression in points of endothelial cell contacts. C. Oligodendrocytes showing strong expression of JAM-C at sites of interactions with neurons. D. High magnification of JAM-C expression on oligodendrocytes at contacts with a neuron and (indicated by the arrow) (Magnification: A 20×, B 40×, C 40×, D 63×).

The unexpected expression of JAM-C protein by glioma tumour cells prompted us to analyse the pattern of JAM-C expression in the normal human brain. We profited of the availability of non-tumoral human brain samples to investigate the expression of JAM-C in non-tumoral astrocytes. On non-tumoral brain tissues obtained from epileptic surgery we observed an expected JAM-C staining in blood vessels (FIG. 4 A). The pattern of JAM-C expression in endothelial cells was highly suggestive of its localization at inter-endothelial cell junctions as previously described (FIG. 4 B). In addition, JAM-C was also detected in oligodendrocytes at points of cell junctions with the neuronal cell bodies (FIG. 4 B). Non-tumoral astrocytes did not appear to express JAM-C. However, since this is not an extensive analysis of the normal human brain, it cannot be excluded that some level of JAM-C expression by astrocytes might be present in particular structures of the normal human brain.

Overall these findings suggested that astrocytoma cells abnormally up-regulate the expression of JAM-C possibly in light of the acquisition of a specific advantage for their malignant behaviour.

TABLE 5

Summary of the results of expression analysis of JAM-C and JAM-B in human gliomas as assessed by immunohistochemistry.

| | | JAM-C | | JAM-B | |
|---|---|---|---|---|---|
| Patient | Tumour | Majority of Cells | Few Cells | Majority of Cells | Few Cells |
| Ge 52  | Ependymoma       | ++  |     | +   |     |
| Ge 140 | Oligodendroglioma| ND  | ND  |     | +   |
| Ge 162 | Oligodendroglioma| ND  | ND  | ++  |     |
| Ge 356 | Oligodendroglioma| ++  | +++ | +   |     |
| Ge 357 | Oligodendroglioma| ++  | +++ | +   |     |
| Ge 262 | Astrocytoma II   |     | +++ | ND  | ND  |
| Ge 279 | Astrocytoma II   | +/− |     |     | ++  |
| Ge 333 | Astrocytoma II   | ++  | +++ | +   |     |
| Ge 407 | Astrocytoma II   | ND  | ND  | ++  |     |
| Ge 458 | Astrocytoma II   | ND  | ND  | ++  |     |
| Ge 149 | Astrocytoma III  |     | +   | ND  | ND  |
| Ge 199 | Astrocytoma III  | ++  |     | ND  | ND  |
| Ge 278 | Astrocytoma III  | ++  |     | ND  | ND  |
| Ge 280 | Astrocytoma III  | +   |     | ND  | ND  |
| Ge 296 | Astrocytoma III  | +   | +   | ND  | ND  |
| Ge 299 | Astrocytoma III  | +   |     | +++ |     |
| Ge 328 | Astrocytoma III  | +   |     | ND  | ND  |
| Ge 388 | Astrocytoma III  |     |     | ++  |     |
| Ge 242 | Glioblastoma     |     | +   | ++  |     |
| Ge 258 | Glioblastoma     | +++ |     | +++ |     |
| Ge 293 | Glioblastoma     |     |     | +   |     |
| Ge 305 | Glioblastoma     |     | +++ | ND  | ND  |
| Ge 319 | Glioblastoma     | +++ | +/− | +   |     |
| Ge 324 | Glioblastoma     |     | +   | ++  |     |
| Ge 360 | Glioblastoma     | +   | ++  | +   | +/− |
| Ge 394 | Glioblastoma     | ND  | ND  | +/− |     |
| Ge 400 | Glioblastoma     | ND  | ND  | +   |     |
| Ge 403 | Glioblastoma     | ND  | ND  |     | +   |

Expression on the majority or on few tumour cells was graded according to the intensity of the staining as follows: +/− very weak; + weak; ++ medium; +++ strong. ND: not done.

JAM-B

Figure 5:
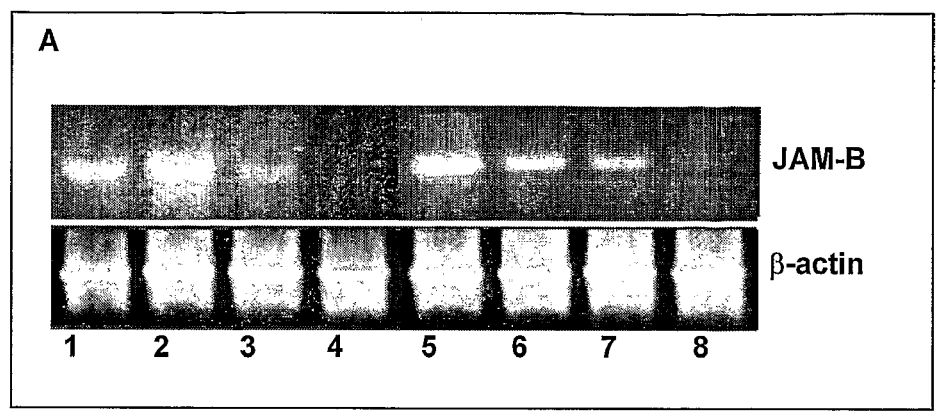
FIG. 5: JAM-B expression in human gliomas. A. RT-PCR for human JAM-B on glioma cell lines. Lanes 1, 3, 7: astrocytomas (grade III) Ge182, Ge328 and Ge299 respectively, lanes 2, 4, 5, 6: glioblastomas Ge258 and Ge360, Ge224 and Ge242 respectively, lane 8: oligoastrocytoma Ge314. B. Cytofluorimetric analysis of JAM-B expression on Ge258 human glioblastoma cells. The histogram shows the profile obtained with the anti-JAM-B polyclonal antibody (black open curve) and the isotype control antibody (gray-filled curve). C. Western blot of human JAM-B in normal human brain (epilepsy biopsy) (lane 1), Ge258 human glioblastoma biopsy (lane 2) and Ge 258 human glioblastoma cell line (lane 3).
Figure 5:
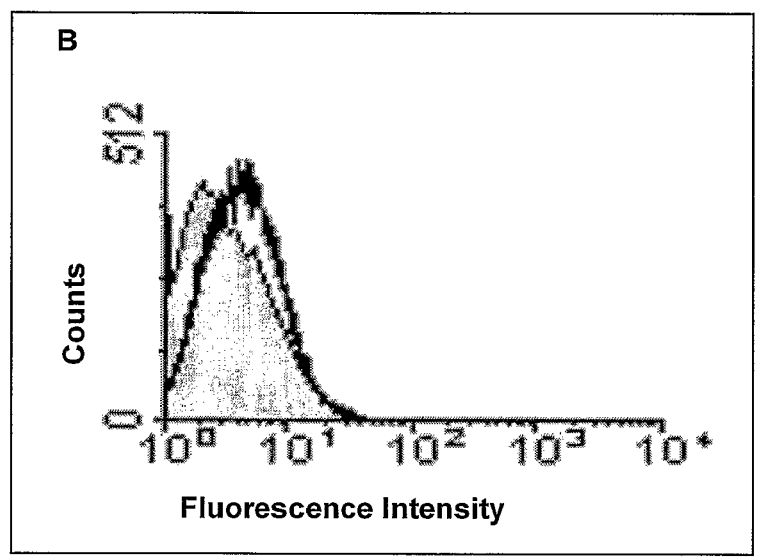
Figure 5:
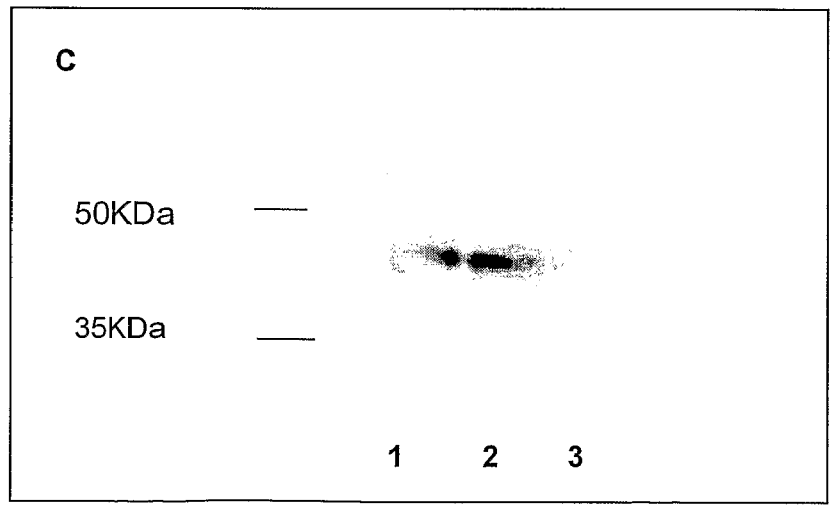

Expression of JAM-B mRNA was first investigated by RT-PCR analysis in a series of human astrocytoma/glioma cell lines of different malignant grade (FIG. 5 A). Expression of JAM-B mRNA was more heterogeneous than JAM-C. Few glioblastoma cell lines did not express JAM-B and others showed weak expression (FIG. 5 A). The expression of JAM-B protein by tumour cells was then confirmed by FACS analysis and immunoprecipitation of selected glioma cell lines (FIGS. 5 B and C). In the Ge258 glioblastoma cell line the level of JAM-B protein on the surface of tumour cells was lower than that of JAM-C (FIG. 5 B). By Western blot analysis we detected two slightly different molecular weight bands (FIG. 1 C). These two apparently different forms of the protein might represent two different states of glycosylation of JAM-B. This was already described for other members of the JAM family, in particular for JAM-A. Furthermore, Western blot analysis revealed the presence of JAM-B protein in a normal human brain sample (epilepsy biopsy).

Then, JAM-B protein expression was analysed by immunohistochemistry on a series of human astrocytomas/gliomas of different malignant grade (N=19) (FIG. 6) and (Table 5).

Figure 6:
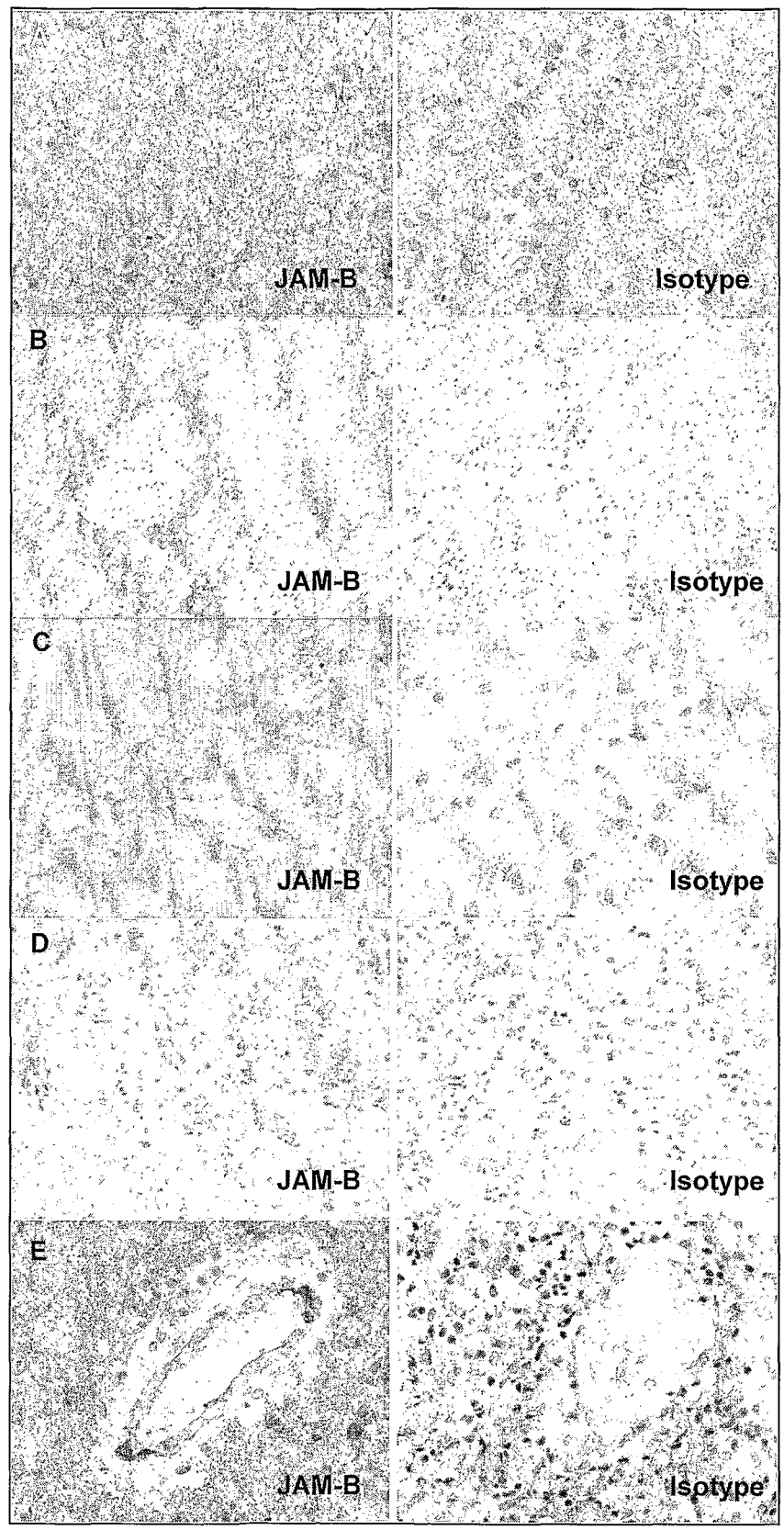
FIG. 6: Heterogeneous JAM-B expression in human astrocytomas as assed by immunohistochemistry (IHC). A. Ge299 astrocytoma (grade III) showing strong expression of JAM-B on all tumour cells. B. Ge242 giant cell glioblastoma. Intra-tumour heterogeneity for JAM-B expression can be observed. C. Higher magnification of Ge242 glioblastoma showing membrane expression of JAM-B on monstrous giant cells. D. Ge394 glioblastoma with heterogeneous expression of JAM-B. E. Blood vessel expressing JAM-B in Ge258 glioblastoma (Magnification: A 40×, B 10×, C 40×, D 20×, E 40×).

As expected, we found JAM-B expression on blood vessels (FIG. 6 E). The pattern of JAM-B expression by endothelial cells appeared different from that of JAM-C (FIGS. 4 A and B). JAM-B was uniformly distributed on the endothelial cell membranes and was absent at sites of cell-cell junctions (FIG. 6 E). This is in accordance with previous reports where JAM-B ectopically expressed in MDCK cells diffusely distributed on the cell membranes. In addition to vascular endothelial cells, an unexpected expression of JAM-B was also observed on the surface of glioma tumour cells in tumours of different grade of malignancy (FIG. 6).

The pattern of expression of JAM-B on tumour cells differed from that of JAM-C for its uniform distribution on the cell membranes and the absence of increased expression at sites of cell-cell contact (FIG. 6). However, similarly to what observed for JAM-C, intra-tumour heterogeneity was detected (FIGS. 6 B, C, and D) with regions where JAM-B was completely absent on the surface of tumour cells (FIGS. 6 B and D), and regions where it was significantly expressed (FIGS. 6 B and D). These findings suggested that similarly to JAM-C, glioma cells might also abnormally express JAM-B.

Figure 7:
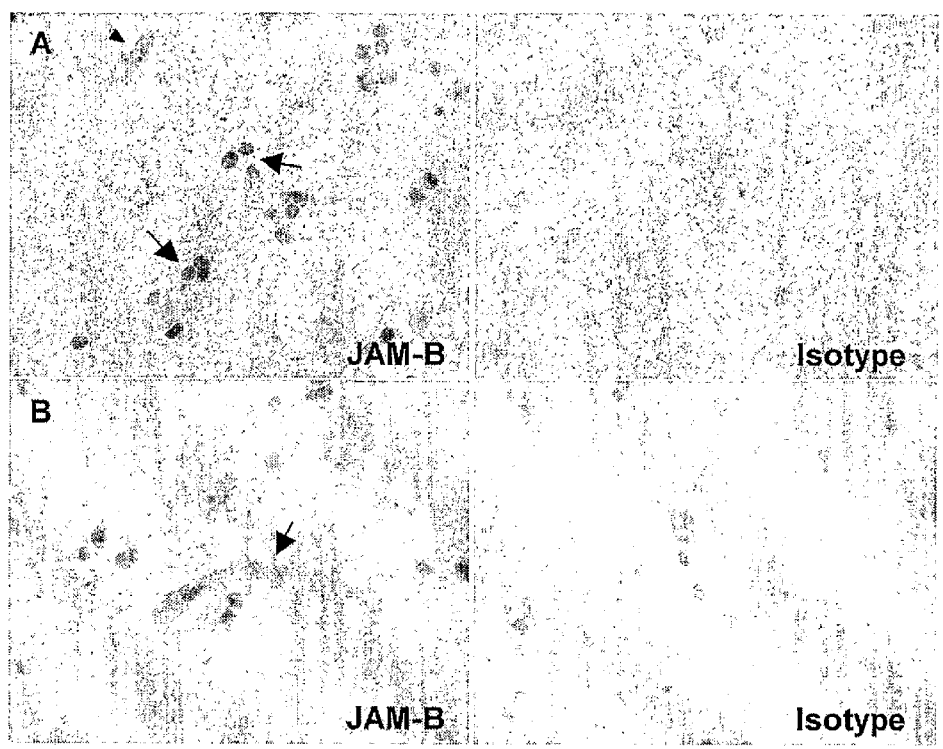
FIG. 7: JAM-B expression on oligodendrocytes and blood vessels on non-tumoral human brain as detected by immuno-histochemistry. A. JAM-B expression on oligodendrocytes on non-tumoral human brain (normal brain tissue adjacent to Ge258 glioblastoma biopsy). Arrows indicate strongly positive oligodendrocytes close to neuronal cells. The arrowhead indicates a positive capillary. B. Expression of JAM-B on blood vessel (indicated by the arrow) in normal brain tissue adjacent to Ge258 glioblastoma biopsy (Magnification: A 40×, B 40×).

To confirm this hypothesis we took advantage of the availability of non-tumoral human brain biopsies to investigate the expression of JAM-B in non-tumoral astrocytes. In the non-tumoral human brain samples (normal tissue adjacent to Ge258 glioblastoma) we observed an expected expression of JAM-B on vascular endothelial cells (FIGS. 7 A and B) and a strong JAM-B expression on oligodendrocytes cell bodies (FIG. 7 A). Again the pattern of JAM-B expression in oligodendrocytes was very different from that of JAM-C (FIG. 4 B), since it was not restricted to points of oligodendrocyte-neuron contacts but it was rather present at high levels on the entire membrane of the oligodendrocyte cell body. Similarly JAM-B was uniformly distributed on the membrane of vascular endothelial cells and not limited to endothelial cell-cell contacts as observed for JAM-C (FIG. 7 B). Non-tumoral astrocytes did not appear to express JAM-B. However, as mentioned for JAM-C, since this is not an extensive analysis of normal human brain, we cannot exclude that JAM-B might be expressed at some levels in astrocytes of particular brain structures.

Overall these findings suggested that astrocytic tumour cells abnormally up-regulated the expression of the JAM-B protein and that high levels of the protein on their membrane might represent a specific gain for their malignant phenotype as observed for JAM-C.

Example 2

JAM-C and JAM-B Expression in GL261 Mouse Glioma

Results
JAM-C

Figure 8:
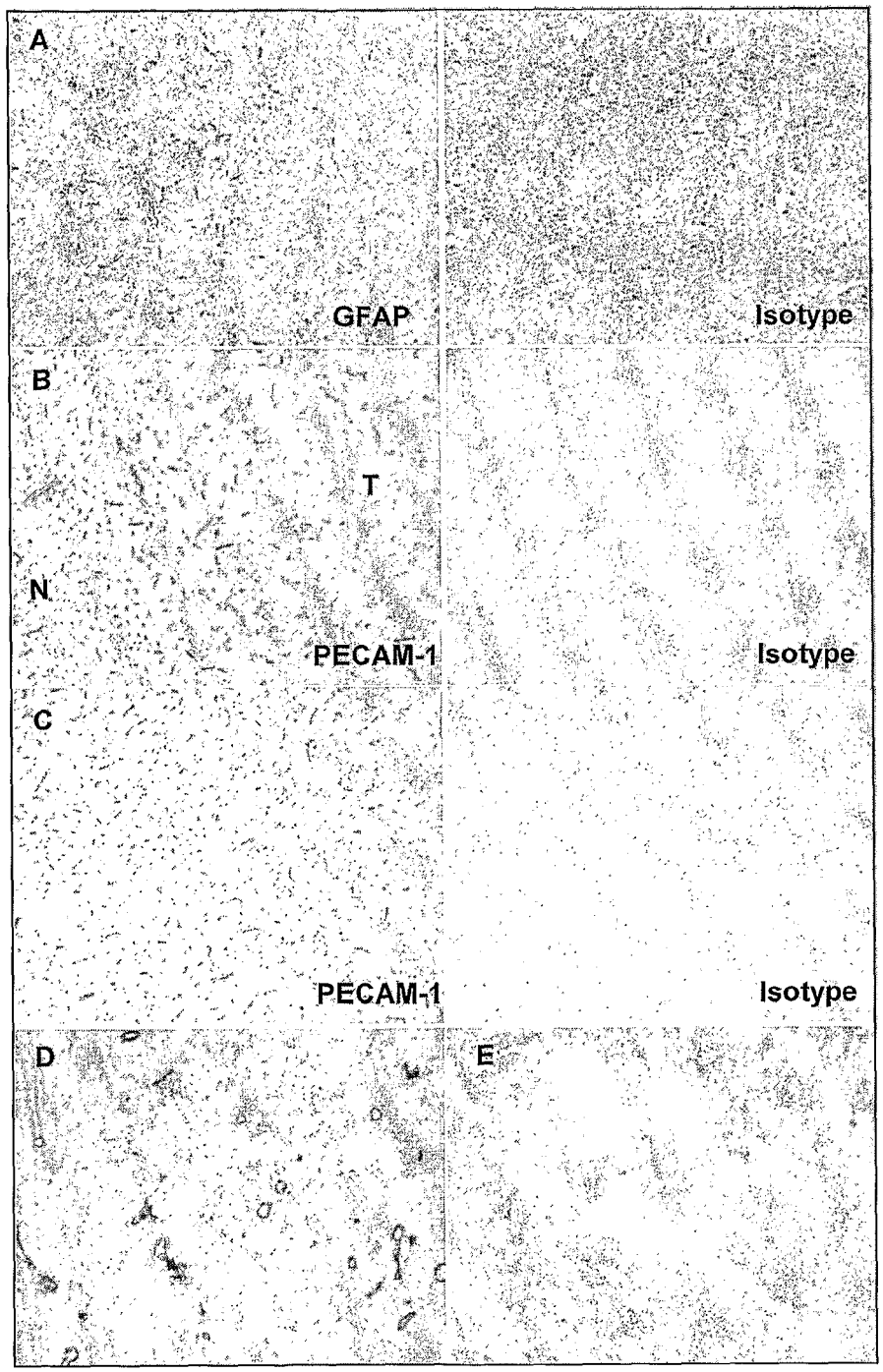
FIG. 8: The GL261 mouse glioma model shows histo-pathological features of human glioblastoma. A. GL261 cells express the GFAP marker for astrocytes in a heterogeneous way typically observed in human glioblastoma. B. Prominent vascularisation induced by GL261 cells stereotaxically implanted in C57BL/6 mouse brain. The tumour associated vessels (highlighted by PECAM-1 staining) show increased density and size compared to the normal mouse brain (see C) (T indicates the tumour mass, N indicates the surrounding normal brain). C. Vascularisation of a normal C57BL/6 mouse brain. The vessels (highlighted by PECAM-1 staining) have smaller size and show lower density compared to those induced by GL261 tumour (see B). D. Large areas of necrosis associated with GL261 tumour growing subcutaneously in C57BL/6 mouse. Notice the islands of tumour cells surviving around blood vessels highlighted by PECAM-1 staining. E. Large areas of necrosis associated with GL261 tumour growing intra-cerebrally in C57BL/6 mouse. As in D tumour cells survive around blood vessels highlighted by PECAM-1 staining. (Magnifications: A 10×, B 2.5×, C 2.5×, D 5×, E 5×).

To investigate the role of JAM-C and possibly JAM-B in gliomagenesis and progression, we selected the GL261 mouse model of human glioma. GL261 cells were originally derived from a tumour induced by intra-cerebral injection of 3-methylcholantrane in syngeneic C57BL/6 mice (Ausman et al., 1970). GL261 cells recapitulate the major features of human glioblastoma, since we could observe not only a very high proliferation rate, invasiveness in the normal brain tissues, and heterogeneous expression of the astrocyte marker GFAP (FIG. 8 A), but also the characteristic histopathological features of human glioblastomas: prominent vascularisation and necrosis (FIGS. 8 B, C, D, and E).

Figure 9:
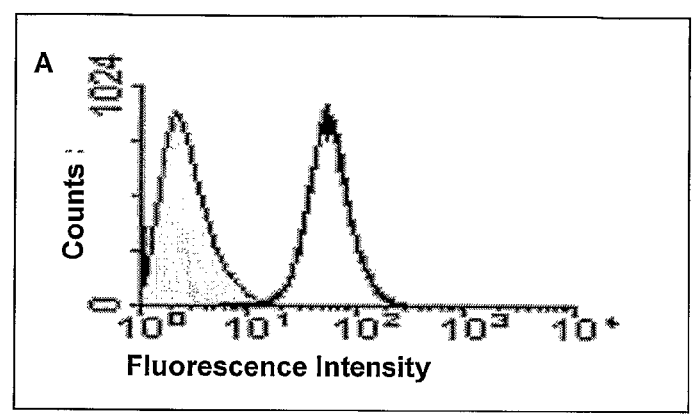
FIG. 9: JAM-C expression in GL261 mouse glioma. A. Cytofluorimetric analysis of JAM-C expression on GL261 glioma cells. The histogram shows the staining profile obtained with the anti-JAM-C monoclonal antibody (black open curve) and the isotype control antibody (gray-filled curve). B. Immunoprecipitation of mouse JAM-C in GL261 mouse glioma cells. Lane 1: pre-immune rabbit serum, lane 2: polyclonal anti-mouse JAM-C. C. and D. Immunohistochemistry for mouse JAM-C on C57BL/6 mouse brain stereotaxically implanted with GL261 cells. The glioma growing in the C57BL/6 mouse brain (denoted by a dashed line) shows the majority of GL261 tumour cells expressing high levels of JAM-C. (Magnification: C 20×, D 40×).
Figure 9:
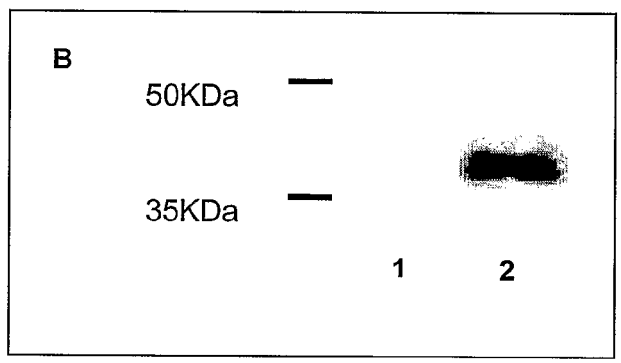
Figure 9:
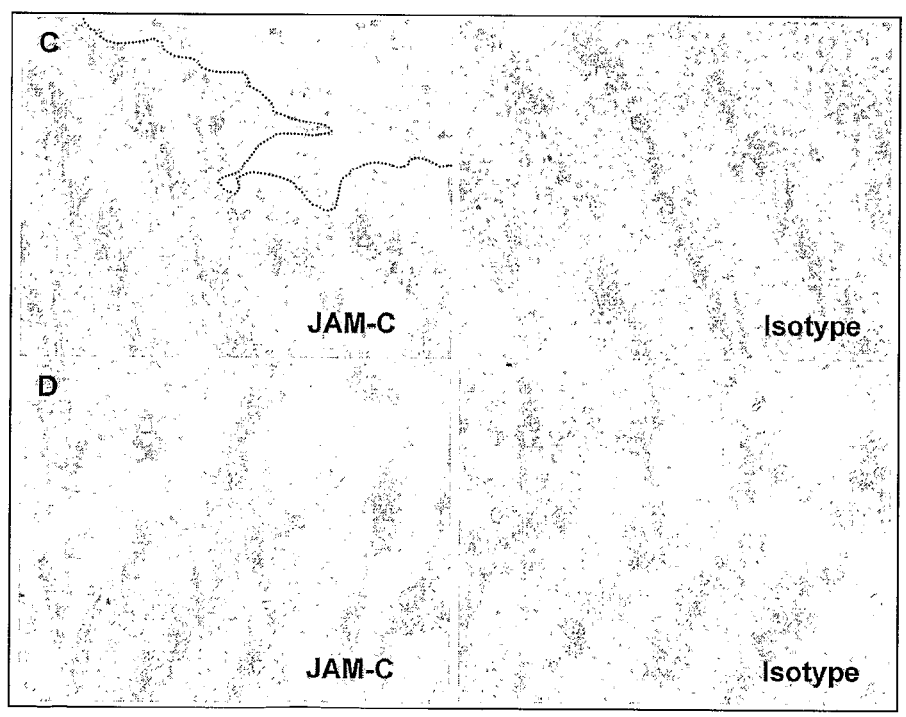
Figure 10:
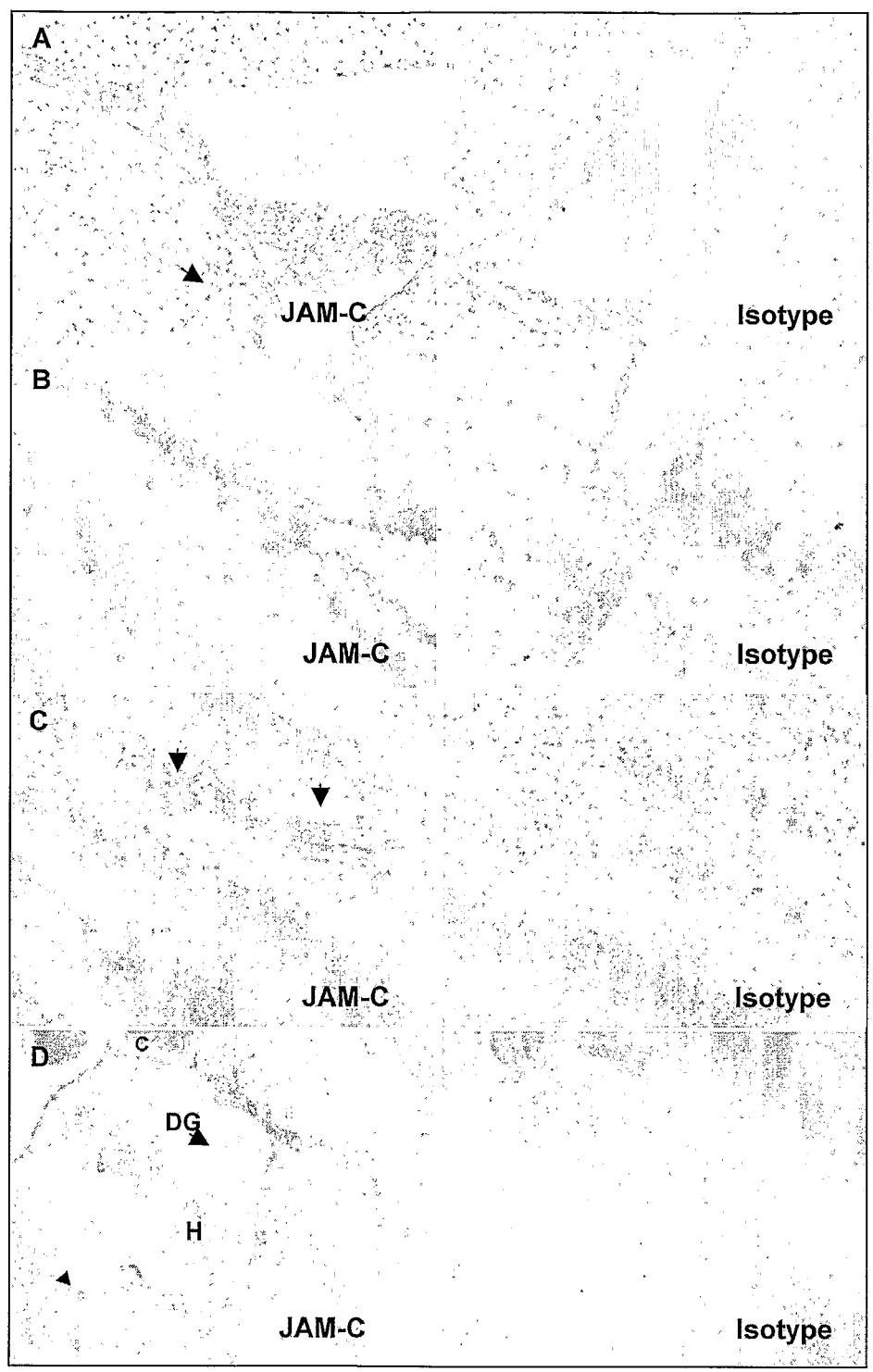
FIG. 10: Expression of JAM-C in C57BL/6 normal mouse brain. A. All ependymal cells lining the ventricles strongly express JAM-C. The arrow indicates stained vascular endothelial cells B. Higher magnification of JAM-C immunostaining on ependymal cells. C. JAM-C stained blood vessels are indicated by arrows. D. Low magnification of the mouse brain showing intense JAM-C staining on little blood vessels (arrowhead) and the entire layer of ependymal cells lining the ventricular system. The hippocampus is visible (H) with the dentate gyrus (DG and arrow) and a small part of the cerebellum (C) (Magnification: A 10×, B 20×, C 10×, D 2.5×).

We first analysed JAM-C expression on GL261 mouse glioma cells by FACS analysis and immunoprecipitation. JAM-C protein was highly expressed at the surface of GL261 mouse glioma cells (FIGS. 9 A and B). Furthermore, when GL261 cells were stereotaxically implanted into the brain of syngeneic C57BL/6 mice they showed high levels of JAM-C protein expression on the cell membranes and aberrant up-regulation as compared to the normal surrounding mouse brain tissue (FIGS. 9 C and D). In the normal mouse brain JAM-C was detected on vascular endothelial cells (FIGS. 10 A and C) and in ependymal cells all along the ventricular system (FIGS. 10 A, B and D). Astrocytes did not show JAM-C expression.

These data indicated that, as observed in several human astrocytomas of different malignant grade, the GL261 mouse glioma cells aberrantly express high levels of JAM-C protein. Therefore, the GL261 glioma, thanks to its biologic features highly reminiscent of those of human glioblastoma and to the very high levels of JAM-C expression represents an ideal model for investigations of the role of this protein for the development and progression of this tumour.

JAM-B

Figure 11:
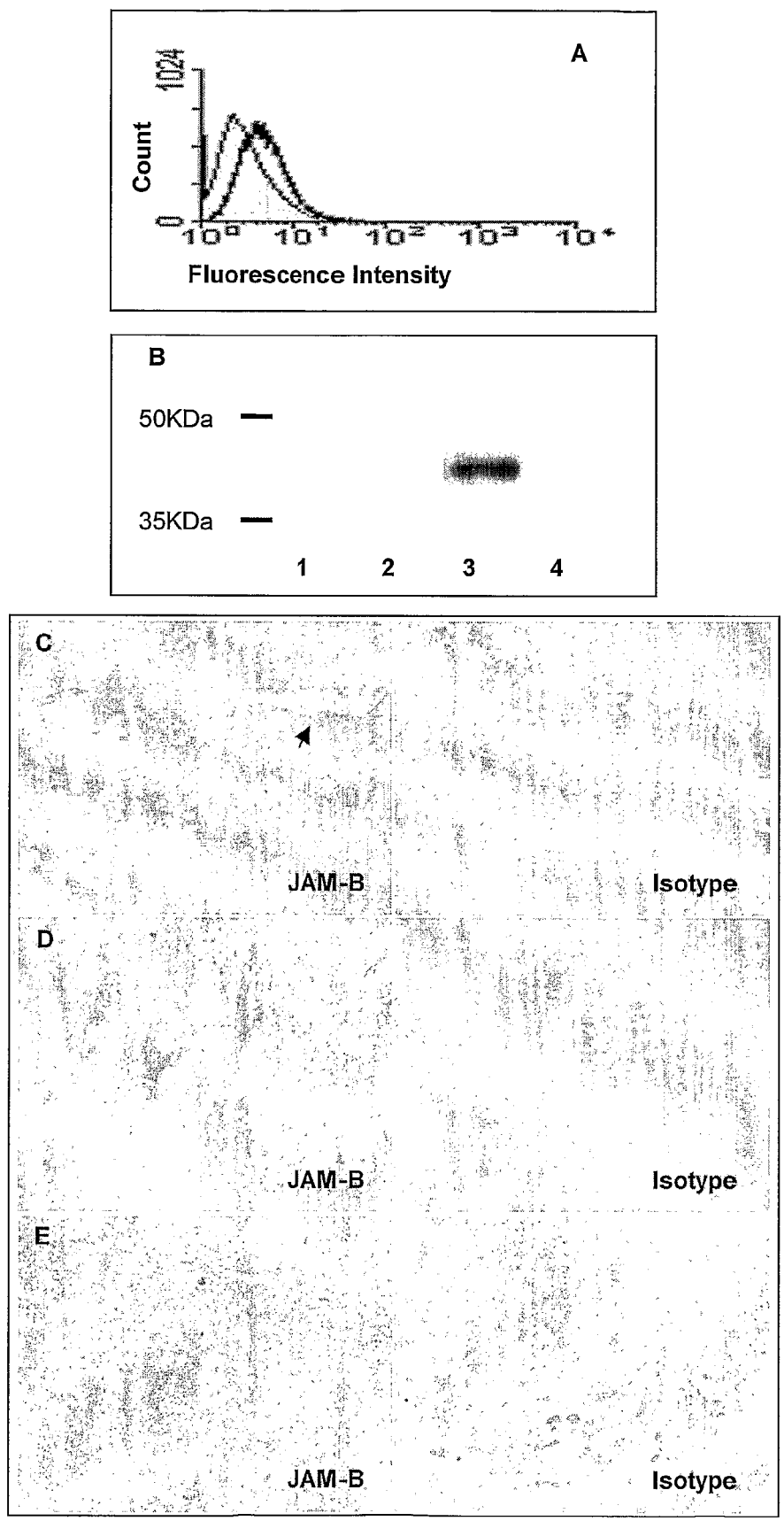
FIG. 11: JAM-B expression in mouse GL261 glioma. A. Cytofluorimetric analysis of JAM-B expression on GL261 mouse glioma cells. The histogram shows the profile obtained with the anti-JAM-B monoclonal antibody (black open curve) and the isotype control antibody (gray-filled curve). B. Immunoprecipitation of mouse JAM-B in GL261 cells. Lane 1: pre-immune rabbit serum, Lane 2: monoclonal isotype control, Lane 3: polyclonal anti-JAM-B antibody, Lane 4: monoclonal anti-JAM-B antibody. C., D., E., Immunohistochemistry for JAM-B on brains of C57BL/6 mice stereotaxically implanted with GL261 cells. JAM-B is expressed at the surface of the majority of GL261 cells (C,D,E) with strong levels on groups of them (C and D). A blood vessel expressing high levels of JAM-B is indicated by the arrow in C. (Magnification: C, D, E 20×).

JAM-B expression on GL261 mouse glioma cells was detected by FACS analysis and immunoprecipitation (FIGS. 11 A and B). The JAM-B protein was expressed at the surface of GL261 mouse glioma cells although at lower level than JAM-C.

This pattern of expression was then confirmed by immunohistochemistry on brains derived from C57BL/6 mice stereotaxically implanted with GL261 mouse glioma cells. Expression of JAM-B protein was found at low levels on the membrane of the majority of tumour cells and at strong levels on some groups of GL261 cells (FIGS. 11 C and E).

Figure 12:
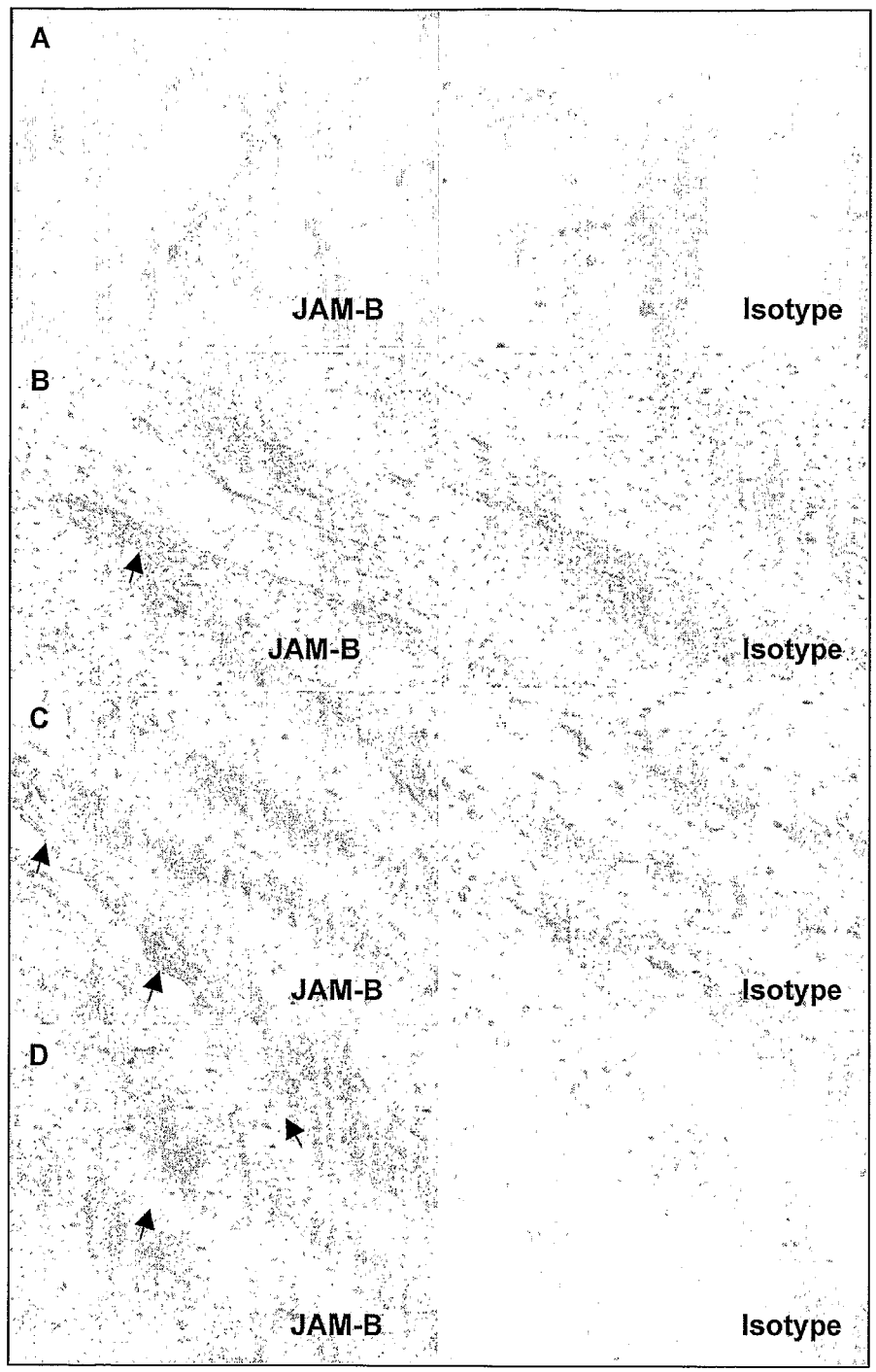
FIG. 12: Expression of JAM-B in the wild-type mouse brain. A. JAM-B is expressed by vascular endothelial cells at high levels. B. JAM-B is strongly expressed by ependymal cells (indicated by the arrow). C. Higher magnification of B showing high levels of JAM-B expression on ependymal cells along the ventricle (indicated by the arrows). D. Low levels of JAM-B expression appear to be present around structures where JAM-B is absent (two of them are indicated by the arrows).

In the normal mouse brain tissue JAM-B was detected at high levels on blood vessels (FIG. 12 A) and ependymal cells lining the ventricles (FIGS. 12 B and C), and possibly at a uniform low level in the entire glial cell compartment (FIG. 12D). This was suggested by the observation that low levels of JAM-B immunoreactivity appeared to surround structures of the normal mouse brain where JAM-B seemed to be completely absent (FIGS. 12 B, C, and D). The identity of such structures remains to be clarified but they might represent the corpus callosum (FIG. 12 C) and myelinated fibre tracts (FIG. 12 D).

Taken as a whole these findings indicated that in mouse GL261 glioma the JAM-B protein was expressed on the membrane of the great majority of tumour cells with particularly high levels in a subset of the tumour cell population.

Example 3

Anti-JAM-C Antibody has Minor Inhibitory Effect on Heterotopic Glioma Growth and Angiogenesis To investigate the relevance of JAM-C expression for GL261 glioma development in vivo, we first injected GL261 cells subcutaneously into C57BL/6 syngeneic mice and treated them with intra-peritoneal injections of anti-JAM-C blocking D33 antibody, isotype control 9B5 antibody, or PBS.

Results

Figure 13:
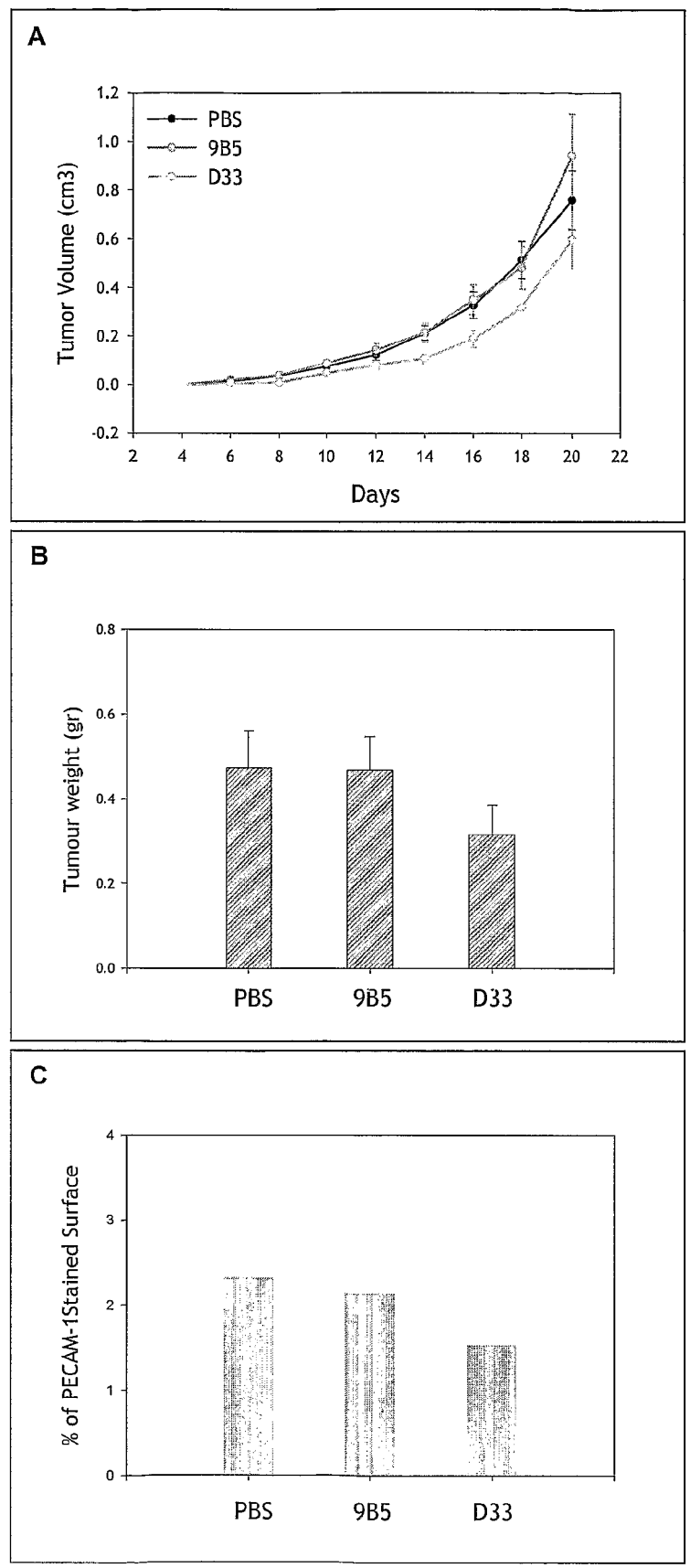
FIG. 13: Anti-JAM-C blocking D33 antibody has an effect on subcutaneous GL261 glioma growth and tumour associated angiogenesis. A. Mean tumour volumes overtime in mice subcutaneously injected with GL261 cells and treated with PBS, isotype control antibody or anti-JAM-C antibody. The graph represents the data of two separate experiments with a total number of 17 mice (PBS), 16 mice (isotype control 9B5 antibody) and 16 mice (anti-JAM-C D33 antibody). Bars represent means±SEM. B. Mean tumour weights. Bars represent means±SEM C. Quantification of tumour associated angiogenesis. The graph shows de degree of vascularisation of a group of tumours (7 per treatment) grown in mice treated with PBS, isotype control 9B5 or anti-JAM-C D33 antibody. Bars represent means±SD.

Treatment of the mice with D33 anti-JAM-C antibody moderately reduced subcutaneous tumour growth overtime (FIG. 13 A) as compared to isotype control 9B5 antibody or PBS. This resulted in reduced tumour weights at sacrifice in mice that received anti-JAM-C D33 antibody treatment compared to isotype control 9B5 antibody or PBS treatments (FIG. 13 B). Since another monoclonal anti-JAM-C antibody (H33) was recently shown to reduce in vivo angiogenesis associated with a mouse Lewis Lung Carcinoma (Lamagna et al., 2005a), we thought to analyse whether a similar effect was responsible for the observed reduction in subcutaneous GL261 glioma growth. Therefore, to analyse the degree of tumour vascularisation, tumour vessels were stained with an anti-PECAM -1 monoclonal antibody (GC51) and the percentage of the stained surface relative to the entire cryosection tumour area was quantified. Treatment with the anti-JAM-C blocking D33 antibody partially reduced tumour associated angiogenesis as compared to isotype control 9B5 antibody or PBS treatment (FIG. 13 C). The extent of angiogenesis inhibition was very similar to that previously described for the H33 anti-JAM-C monoclonal antibody, suggesting that the D33 and H33 anti-JAM-C antibodies might act through similar mechanisms. However, despite a similar inhibitory effect on in vivo tumour associated angiogenesis, in vivo subcutaneous GL261 glioma growth was not significantly inhibited.

Therefore, these results suggested that the in vivo heterotopic growth of GL261 glioma was partially impaired by anti-JAM-C D33 blocking antibody, that this might have occurred through inhibition of tumour associated angiogenesis, and that the incomplete efficacy of the D33 anti-JAM-C antibody in restraining GL261 glioma growth might be ascribed to the peculiarity of this tumour type. In particular, the anti-angiogenic effect of D33 anti-JAM-C antibody might not have been sufficient to inhibit the growth of highly aggressive GL261 cells. Alternatively, these findings might suggest that JAM-C expressed by glioma cells might be important for the growth of the tumour in its natural environment, and that targeting JAM-C on orthotopically growing GL261 gliomas might have a different outcome.

Example 4

Figure 14:
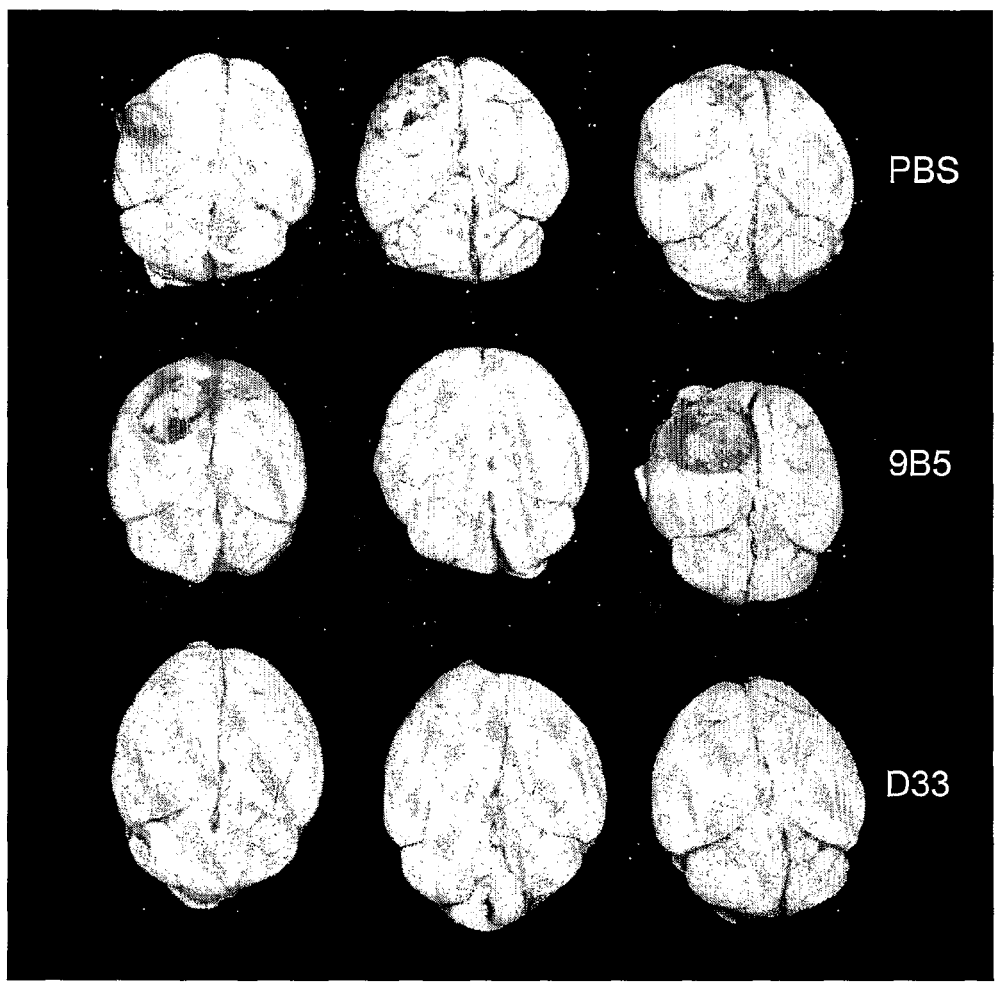
FIG. 14: Macroscopic appearance of brains of C57BL/6 mice stereotaxically implanted with GL261 cells and treated with PBS, isotype control antibody 9B5 or anti-JAM-C antibody D33. Extensive tumour masses are visible at the site of tumour implantation (left hemisphere) in PBS and 9B5 treated mice while they are undetectable in D33 treated mice.
Figure 15:
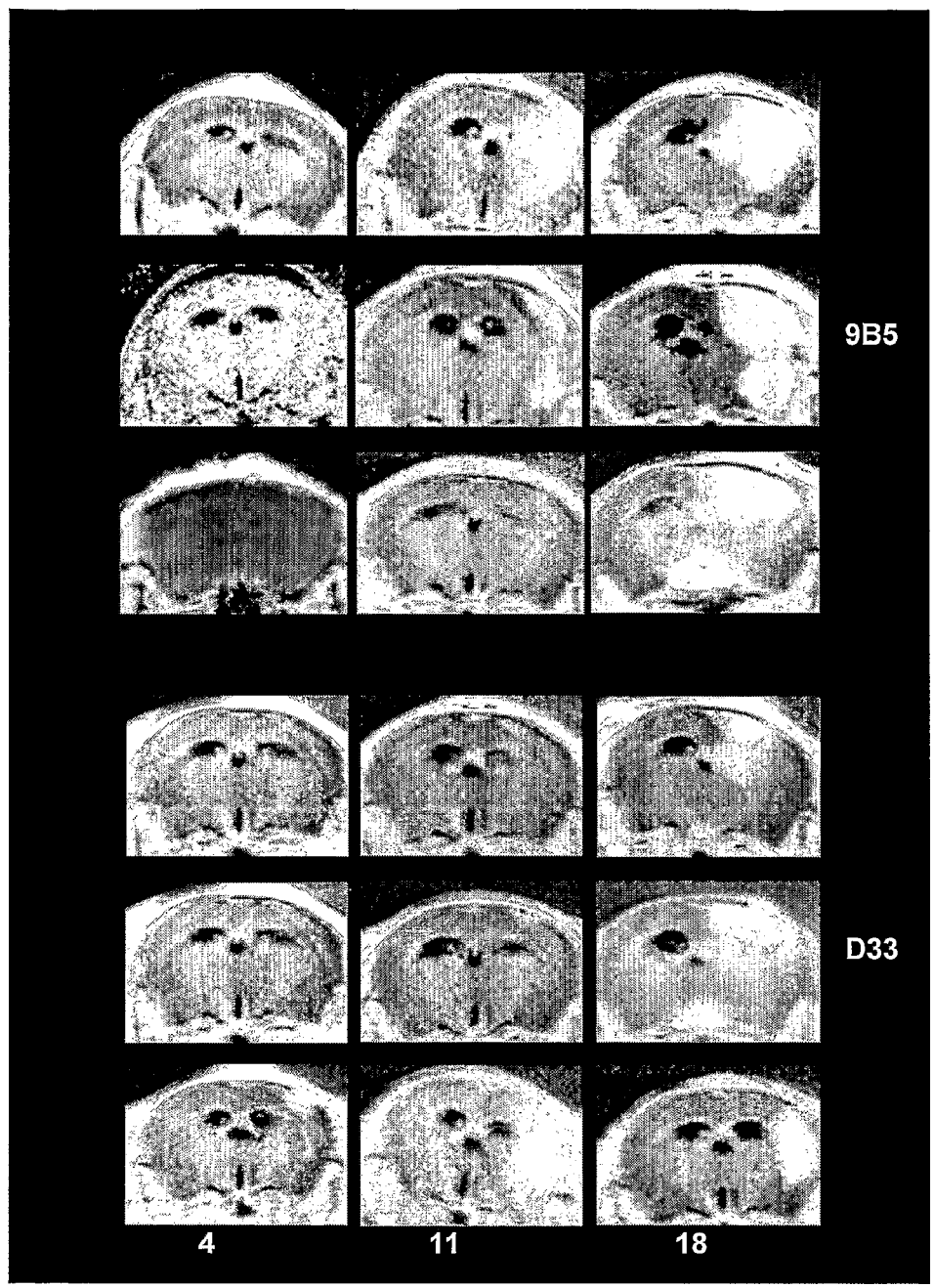
FIG. 15: Anti-JAM-C blocking D33 antibody inhibits intra-cerebral GL261 glioma growth. MRI images of GL261 gliomas grown intra-cerebrally in mice treated with isotype control 9B5 (3 mice) or anti-JAM-C D33 antibody (3 mice). The images were acquired at days 4, 11 and 18 post tumour cell implantation and show a significant reduction in tumour size in mice treated with anti-JAM-C antibody at day 18.
Figure 16:
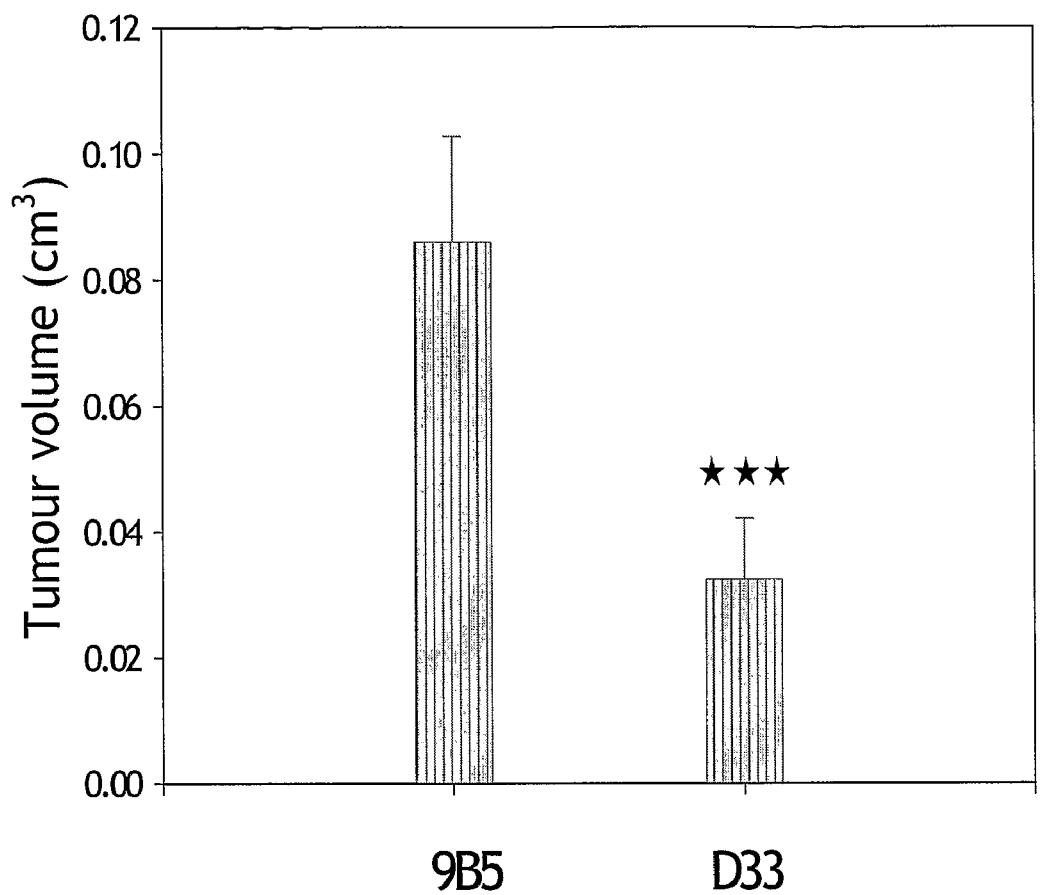
FIG. 16: Anti-JAM-C D33 antibody treatment significantly reduces orthotopic GL261 glioma growth. Intra-cerebral tumour volumes of GL261 gliomas grown in mice treated with anti-JAM-C D33 antibody are significantly smaller than those of mice treated with isotype control 9B5 antibody (p=<0.001). Tumour volumes were calculated from MRI images acquired at day 18 post tumour cell implantation and represent the values obtained from 6 and 5 mice treated with 9B5 or D33 antibody, respectively. Bars represent means±SD.

Anti-JAM-C Antibody Significantly Inhibits Orthotopic GL261 Glioma Growth and Spreading To test this last hypothesis we decided to investigate the effect of anti-JAM-C blocking D33 antibody treatment on intra-cerebral GL261 gliomas. To this end GL261 cells were stereotaxically implanted into the brain of C57BL/6 mice which then received intra-peritoneal injections of either blocking anti-JAM-C D33 antibody, isotype control 9B5 antibody, or PBS. At sacrifice at day 20 post tumour cell implantation, the macroscopic appearance of brains derived from mice treated with anti-JAM-C D33 antibody was strikingly suggestive of glioma growth inhibition as compared with that of mice treated with isotype control 9B5 antibody or PBS (FIG. 14). Therefore, in order to monitor and quantify intra-cerebral tumour growth, we stereotaxically implanted GL261 glioma cells into the brain of C57BL/6 mice, treated them with anti-JAM-C D33 antibody or isotype control 9B5 antibody, (as described above), and analysed the brains with Magnetic Resonance Imaging (MRI) at days 4, 11, and 18 post tumour cell implantation (FIG. 15). At day 4 post GL261 cell implantation we could hardly detect tumour cells in the brains of all the mice analysed. At day 11 post implantation all tumours were small and not significantly different in size between the anti-JAM-C blocking D33 antibody and isotype control 9B5 antibody treated mice. At day 18 post GL261 cell implantation, tumour sizes were significantly smaller in anti-JAM-C blocking D33 antibody as compared to isotype control 9B5 antibody treated mice (FIG. 15). Quantification of all tumour volumes revealed a highly significant inhibition in GL261 intra-cerebral tumour growth at day 18 post cell implantation in mice treated with the anti-JAM-C blocking D33 antibody (FIG. 16).

Figure 17:
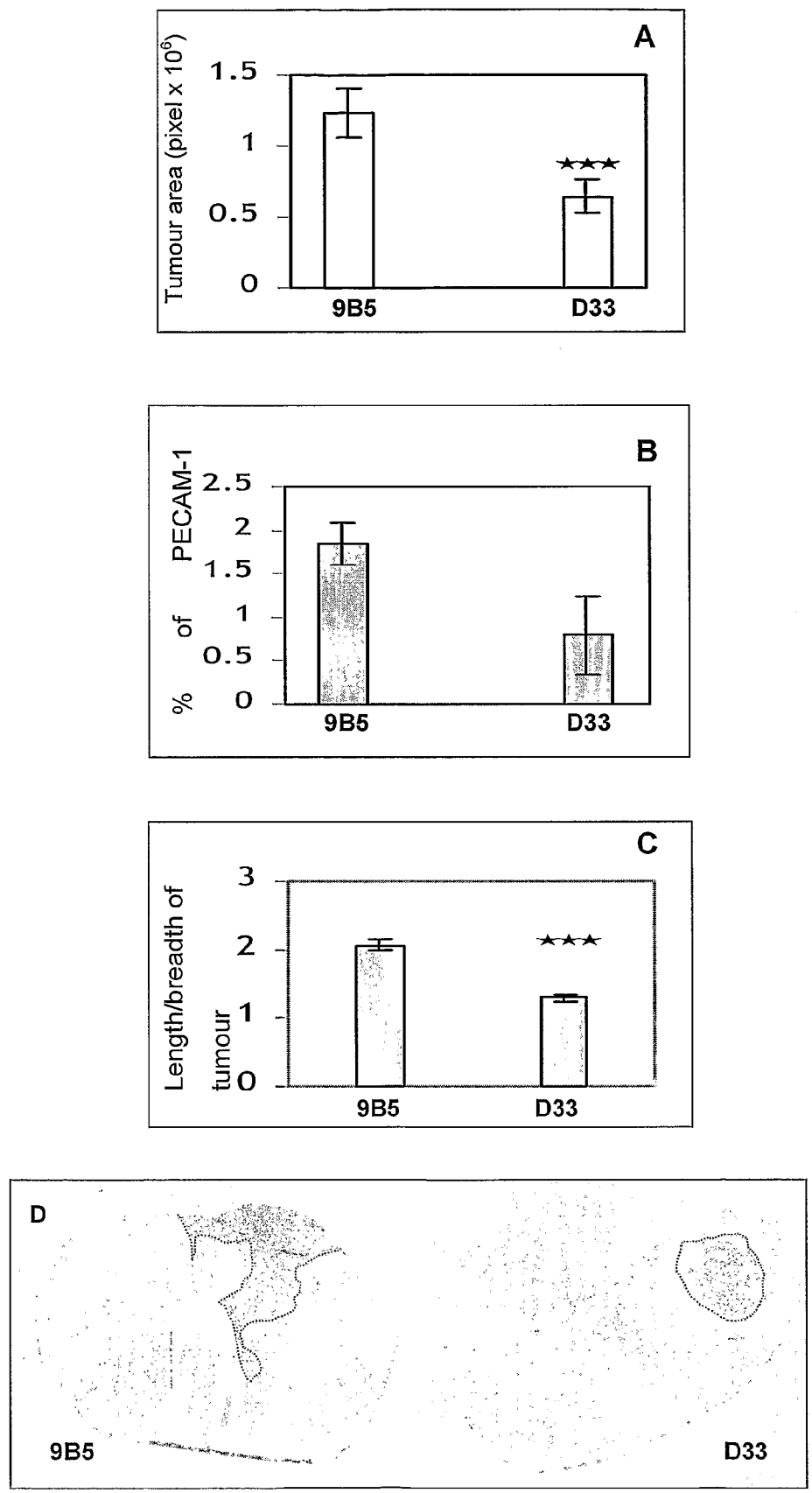
FIG. 17: Anti-JAM-C D33 antibody inhibits intra-cerebral GL261 glioma growth reduces tumour associated angiogenesis and affects tumour shape. A. Tumour areas of GL261 glioma grown in mice treated with anti-JAM-C D33 antibody are significantly smaller than those of mice treated with 9B5 isotype control antibody (p=0.049). Bars represent means±SEM. B. Anti-JAM-C D33 antibody treatment shows a trend in reducing GL261 glioma associated angiogenesis as calculated by the percentage of PECAM-1 stained surface on tumour sections. Bars represent means±SEM. C. GL261 gliomas grown in mice treated with anti-JAM-C D33 antibody show significantly more rounded shapes as determined by the length/breadth ratio of tumour areas (p=0.001). Bars represent means±SEM. D. Representative images of the shapes of GL261 gliomas grown in the brain of mice treated with anti-JAM-C D33 antibody or 9B5 isotype control antibody. The tumour areas are outlined by a dashed line. (Images were acquired with Nikon Scan at 4× magnification). All the data were derived from the analysis of three mice per treatment.

To investigate the mechanisms through which the anti-JAM-C D33 antibody mediated inhibition of orthotopic GL261 glioma growth we first analysed whether, as observed for subcutaneously growing tumours, inhibition of angiogenesis might have been a possible mechanism of action of the anti-JAM-C D33 antibody. We therefore performed PECAM-1 stainings of blood vessels on cryosections of the brains derived from mice which were stereotaxically implanted with GL261 glioma cells and received either anti-JAM-C D33 antibody or isotype control 9B5 antibody treatments. The percentage of PECAM-1 stained surface was then quantified relative to the total tumour area on each section (FIG. 17 B).

Results

As observed for subcutaneously growing GL261 gliomas, treatment with anti-JAM-C D33 antibody reduced tumour associated angiogenesis of orthotopically grown GL261 gliomas as compared to isotype control 9B5 antibody treatment, although this did not reach the level of significance. In addition, quantification of tumour areas revealed a significant inhibition of intra-cerebral GL261 glioma growth in mice that received anti-JAM-C D33 antibody compared to isotype control 9B5 treatments (FIG. 17 A). Furthermore, we observed significantly different tumour shapes between GL261 gliomas grown in mice treated with anti-JAM-C D33 antibody or isotype control 9B5 antibody (FIGS. 17 C and D). GL261 gliomas treated with anti-JAM-C D33 antibody showed a round shape without evidence of long distance tumour dissemination (FIG. 17 D). In contrast, G1261 gliomas treated with isotype control 9B5 antibody propagated in a more disseminated way with tumour cells migrated at long distances from the core lesion (FIG. 17 D). These differences in tumour shape suggested that the anti-JAM-C D33 antibody might have not only inhibited tumour growth and reduced associated angiogenesis but also affected the capacity of GL261 glioma cells to spread in the normal brain tissue.

Overall these results indicated that anti-JAM-C blocking D33 antibody strongly inhibited the spreading of GL261 glioma cells in the normal brain tissues and the orthotopic growth of the tumour. Compared to the slight reduction of subcutaneous GL261 glioma growth obtained with the anti-JAM-C D33 treatment, these last findings might mainly be explained with the two following hypothesis.

First, the anti-JAM-C D33 antibody treatment might have been more efficient on intra-cerebrally growing tumours because of the reduced number of GL261 cells implanted ($2\times10^4$) in the brain as compared to the subcute ($10^6$). The GL261 mouse model of glioma is extremely aggressive as observed for human glioblastomas. This limits the number of cells that can be implanted into the mouse brain since as few as $2\times10^4$ cells can develop into a tumour that extends to an entire brain hemisphere in just 20 days only. Often an extra-cranial tumour growth was also observed underscoring the impressive aggressiveness of this glioma tumour model. On the other hand GL261 cells grown subcutaneously give rise to measurable tumours when injected at higher concentrations than in the brain. These observations imply that if the anti-tumour effect of the anti-JAM-C D33 antibody is due to inhibition of tumour associated angiogenesis, the antibody might have had a more pronounced effect on tumours arising from a smaller number of implanted tumour cells.

Second, in the brain, the anti-JAM-C D33 antibody might have not only impaired tumour associated angiogenesis, as in subcutaneously growing tumours, but acted also through other mechanisms, as evidenced by its effect on tumour spreading, suggesting that JAM-C expressed on glioma might be relevant for its development into its natural environment. In this case, JAM-C on glioma cells might interact and/or crosstalk with molecules that are constituents of the brain environment and trigger signals important to enhance glioma development. In this context the anti-JAM-C D33 antibody, in addition to inhibition of angiogenesis might also block important signals for the expansion of glioma.

Example 5

Suppression of JAM-C Expression in GL261 Mouse Glioma Cells by RNA Interference

In order to investigate whether expression of JAM-C by glioma cells could represent an advantage for the acquisition and/or progression of their malignant phenotype in particular in their natural environment and the potential mechanisms through which this could be accomplished, we used GL261 cells to generate two cell lines which differentially expressed JAM-C. In one cell line JAM-C expression was knocked-down (GL261-233RC) and in the other it was highly expressed (GL261-233R). These two cell lines are extremely useful tools for gene expression and in vitro functional analysis as well as for in vivo studies of the relevance of glioma expressed JAM-C for the development and biology of the tumour. To generate them, we first suppressed JAM-C expression in GL261 cells by RNA interference (RNAi). To this end we used the pSuper.gfp/neo vector, which allows the expression of short hairpin RNA (shRNA) sequences that are subsequently processed by the cellular RNAi machinery to give rise to small interfering RNAs (siRNAs). The siRNAs target for degradation the specific mRNA to which they are complementary.

Figure 18:
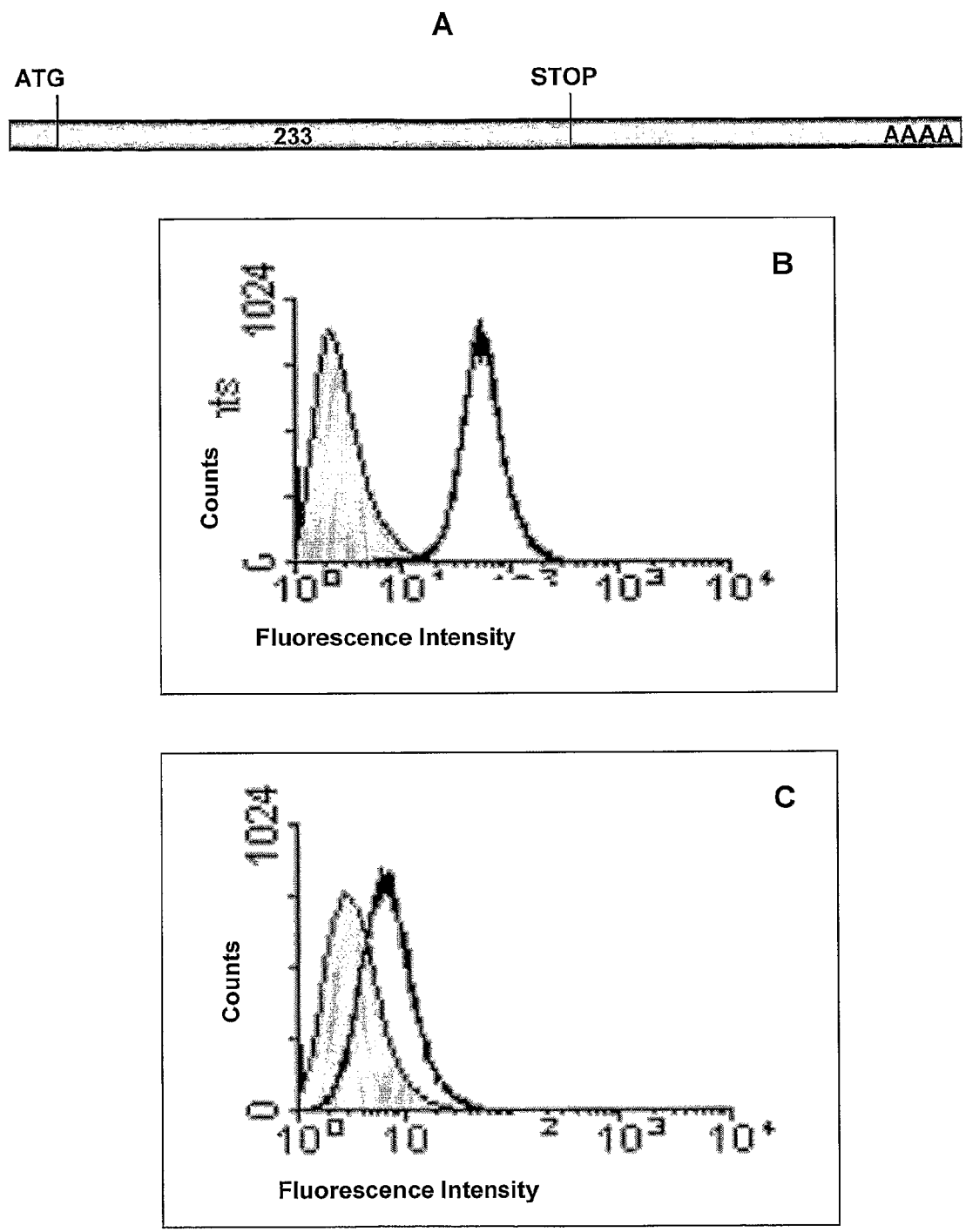
FIG. 18: Suppression of JAM-C expression by RNA interference in GL261 cells. A. Schematic representation of the mouse JAM-C mRNA showing the RNAi 233 target sequence used to target the JAM-C mRNA for degradation. B. and C. Flow cytometry analysis of JAM-C expression in GL261 cells (B) and GL261-233 (C) cells transfected with the pSuper.gfp/neo vector allowing expression of the shRNA 233 target sequence (see A) for the mouse JAM-C mRNA. The level of JAM-C protein expression (black open curve) on GL261-233 (C) cells is highly reduced as compared to the mother GL261 (B) cells. The gray-filled curve shows the isotype control antibody profile.

Therefore several pSuper.gfp/neo vector constructs containing different RNAi target sequences for the mouse JAM-C mRNA were generated and stably transfected in the GL261 cells (FIG. 18 A). The derived cell lines were then analysed for JAM-C expression by FACS analysis. In one of these cell lines, the GL261-233, expression of the JAM-C protein on the surface of tumour cells was significantly reduced as compared to the mother GL261 cell line (FIGS. 18 B and C).

Figure 19:
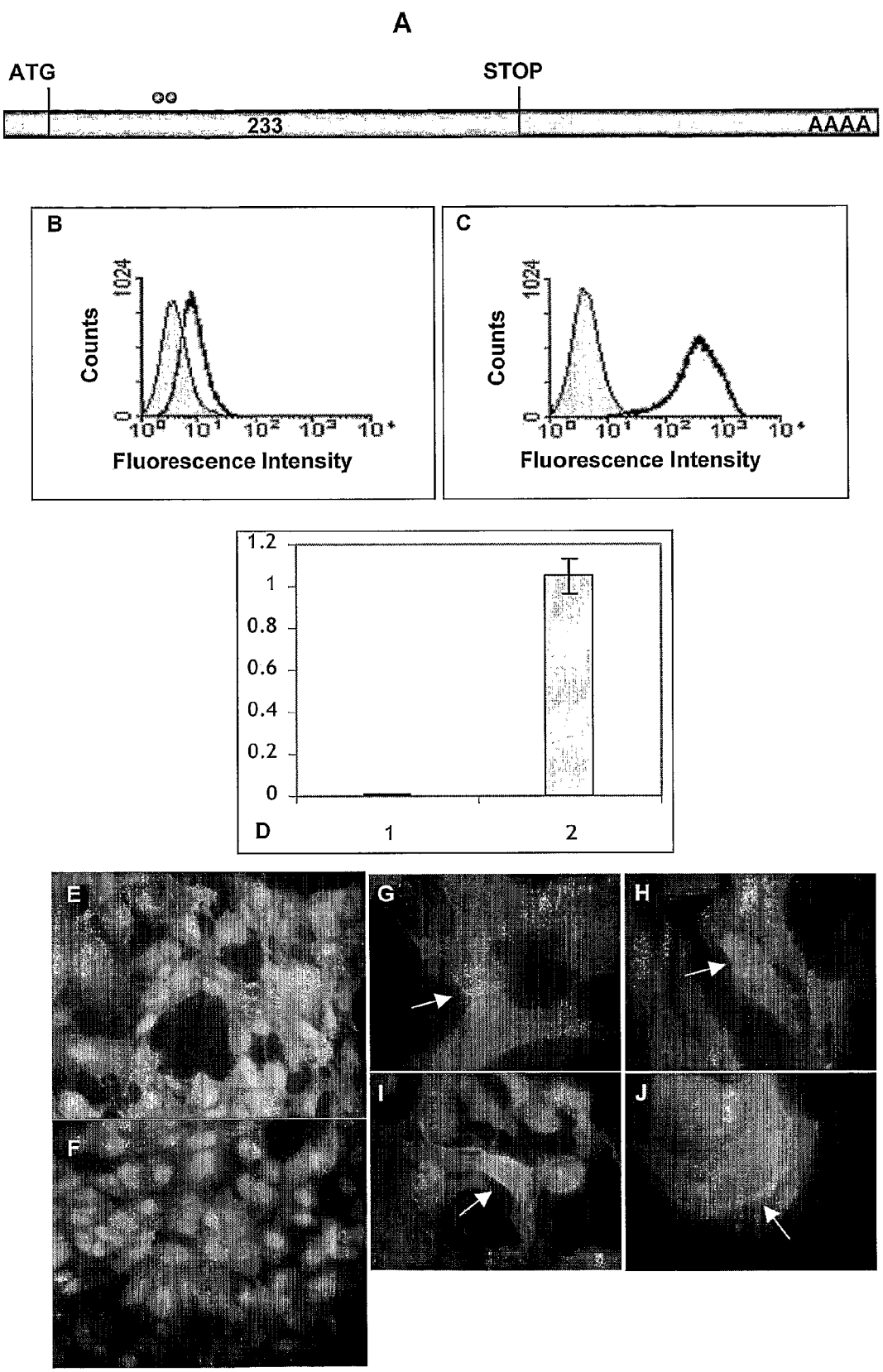
FIG. 19: Rescuing of JAM-C expression in GL261-233 cells. A. Schematic representation of the mouse JAM-C mRNA showing the 233 RNAi target sequence and the two silent point mutations introduced to generate an RNAi resistant JAM-C mRNA. B. and C. Flow cytometry analysis of JAM-C expression in GL261-233RC (B) and GL261-233R (C) cells. The level of JAM-C protein expression (black open curve) on GL261-233R cells is completely rescued (98.8% of cells express JAM-C) compared to the control GL261-233RC (B) cells which show levels of JAM-C expression similar to the mother GL261-233 cells (7% of the cells express JAM-C) (FIG. 19C). The grey-filled curve shows the isotype control antibody profile. D. Real Time PCR for the mouse JAM-C mRNA in GL261-233RC (lane 1) and GL261-233R (lane 2) cells. The y axis indicate the relative amount of mRNA. The level of JAM-C mRNA was 222 fold higher in GL261-233R compared to GL261-233RC cells (p<0.0001). Bars represent means±SD. E and F. Expression of JAM-C in GL261-233R (E) and GL261-233RC (F) cells as detected by immunofluorescence. G, H, I, J. Expression of JAM-C in GL261-233R cells in different sites of the cell membrane. Strong expression of JAM-C is detected at sites of cell-cell contacts (G and J, indicated by the arrow), in restricted points on the cell surface (H, indicated by the arrow), and distributed on the cell membrane in sites not involved in cell-cell adhesion (I) (Magnifications: E and F 40×; G, H, I 63×; J 100×).

From this JAM-C knock-down GL261-233 cell line we then derived two other stable cell lines: a JAM-C rescued cell line (GL261-233R), and the corresponding rescued control cell line (GL261-233RC) (FIG. 19).

The GL261-233R cell line was obtained by transfecting GL261-233 cells with the pcDNA3 expression vector containing the mouse JAM-C cDNA harbouring two silent point mutations into the 233 RNAi target sequence (FIG. 19 A). By this way the cells expressed the endogenous RNAi sensitive and the exogenous mutant RNAi resistant JAM-C mRNAs. The GL261-233RC cell line was obtained by transfecting GL261-233 cells with the mock pcDNA3 vector.

Results

By FACS analysis, the GL261-233R showed re-expression of high levels of JAM-C protein, while the GL261-233RC cells looked still JAM-C knock-down as the mother GL261-233 cells (FIGS. 19 B and C). The significant difference in the levels of JAM-C expression between these two cell lines was also observed at the RNA level by Real Time PCR. This analysis revealed a 222 fold change in the JAM-C mRNA levels between GL261-233RC and GL261-233R cells (FIG. 19 D). Immunofluorescence analysis of JAM-C expression in the two cell lines confirmed the presence of high levels of the JAM-C protein on the membrane of GL261-233R cells, whilst it was almost undetectable in GL261-233RC cells (FIGS. 19 E and F). In addition, we could observe JAM-C at different sites on the cell membranes, including sites of cell-cell contacts (FIGS. 19 G and J) and in restricted points on the cell surface (FIG. 19 H).

Example 6

Gene Expression Analysis of GL261 Cells Differentially Expressing JAM-C

To unveil whether JAM-C expressed by glioma cells might contribute to the achievement of a cancerous phenotype and the mechanisms through which this could be accomplished we first analysed the gene expression pattern resulting from a differential expression of JAM-C on glioma cells. To this end, GL261-233R and GL261-233RC cell lines were first compared by Affymetrix microarray.
Results This analysis showed 49 genes up-regulated and 15 down-regulated in the JAM-C GL261-233R rescued cells as compared to the JAM-C knock-down GL261-233RC control cells. These differentially expressed genes belonged to several types of protein families and cellular pathways, which are described below (Table 6).
Transcription Factors Up-Regulated in GL261-233R Cells Among the transcription regulators, two proto-oncogenes were up-regulated in GL261-233R cells, the FBJ osteosarcoma proto-oncogene (c-Fos) and Fos-like antigen 2 (FosL2).
Protein Kinases Up-Regulated in GL261-233R Cells Protein kinases up-regulated in GL261-233R cells included p21-activated Kinase 3 (Pak3), a brain specific isoform of the PAK protein family, which are important effectors in the cascade of Rho family small GTPases.
Membrane Receptors Up-Regulated or Downregulated in GL261-233R Cells Among membrane receptors up-regulated in GL261-233R cells we found the Poliovirus Receptor (PVR), an IgSf molecule, and Tetraspanin 6 (Tspan6), a member of a large family of proteins forming membrane clusters that participate in several signal transduction processes. A ligand of Tspan6, Prostaglandin F2 receptor negative regulator (Ptgfrn) was also up-regulated in GL261-233R cells.

The membrane transporter Very Low Density Lipoprotein Receptor (VLDLR) was significantly downregulated in GL261-233R cells. This receptor promotes the catabolism of the uPA-plasmin proteolytic system, therefore decreasing the amount of active proteases at the surface of the cells.
Growth Factors Up-Regulated in GL261-233R Cells Brain Derived Neurotrophic factor (BDNF) was a known growth factor whose expression was increased in GL261-233R cells. BDNF is a key neurotrophin regulating cell survival, proliferation and cytoskeleton remodelling in the nervous system through an RTK receptor, the Tyrosine Kinase receptor B (TrKB).
Rho Family Proteins In GL261-233R cells we detected enhanced expression of Rap Guanine Nucleotide Exchange Factor 2 (RapGEF2) which, as mentioned in the introduction, is one member of the GEF family of Rho small GTPases positive regulators.
Cytoskeleton-Related Proteins Several cytoskeleton-related genes were up-regulated in JAM-C expressing GL261-233R cells, notably the Actin Filament Associated Protein (AFAP), an activator of Src family kinases in response to cellular signals directly effecting actin filament organization.

Importantly, JAM-A and JAM-B mRNA levels did not differ between GL261-233RC and GL261-233R cells (data not shown), indicating the specificity of the RNAi silencing vector.

TABLE 6

Genes up-regulated (+) or down-regulated (−) in GL261-233R compared to GL261-233RC cells by Affymetrix microarray analysis.

| Gene Symbol | Description | Fold | p-value | Protein Family |
|---|---|---|---|---|
| Fos | FBJ osteosarcoma oncogene | +1.44 | 0.0000 | Transcription Factor |
| FosL2 | Fos-Like antigen 2 | +1.90 | 0.006 | Transcription Factor |
| PAK3 | p21-activated Kinase 3 | +1.69 | 0.0000 | kinase |
| Tspan6 | Tetraspanin 6 | +1.30 | 0.0024 | Receptor |
| PVR | Poliovirus Receptor | +1.53 | 0.087 | Receptor |
| BDNF | Brain Derived Neurotrophic Factor | +1.74 | 0.0000 | Growth Factor |
| RapGEF2 | Rap guanine nucleotide exchange factor | +1.38 | 0.0000 | Guanine Nucleotide Exchange Factor |
| Ptgfrn | Prostaglandin F2 receptor negative regulator | +2.38 | 0.0004 | IgSf molecule |
| AFAP | Actin Filament Associated Protein | +1.97 | 0.093 | Cytoskeleton protein |
| Eps8 | EGF-pathway substrate 8 | 1.34 | 0.0000 | Peptidase |
| VLDLR | Very Low Density Lipoprotein Receptor | −3.95 | 0.0001 | Receptor Transporter |

The fold change increases or decreases in mRNA levels for these genes were not very high, which was not surprising in light of the fact that JAM-C, as a membrane protein, is unlikely to directly regulate gene transcription. However, the set of genes differentially expressed in GL261-233RC and GL261-233R cell lines strongly suggested that JAM-C expression on the membrane of glioma cells might cause a cascade of intracellular signals, mainly through activation of protein kinases, which might be relevant to glioma development and progression. In particular, up-regulation of RAPGEF2 and PAK3 suggested activation of the Rho family small GTPases pathway and Fos, FosL2 and PVR suggested activation of the MAPK-ERK pathway since the expression of all of them is induced by activation of this signalling cascade. In addition, the up-regulation of the AFAP gene suggested that the c-Src non-receptor tyrosine kinase might be activated in JAM-C over-expressing glioma cells. Moreover, c-Src activation would be the up-stream event to the other above mentioned cascades of intracellular signals.

Overall the set of genes up-regulated in glioma cells expressing high levels of JAM-C suggested that JAM-C might significantly contribute to the malignant behaviour of gliomas. In particular, activation of c-Src would lead to stimulation of several cellular processes including cell motility and invasion.

Figure 20:
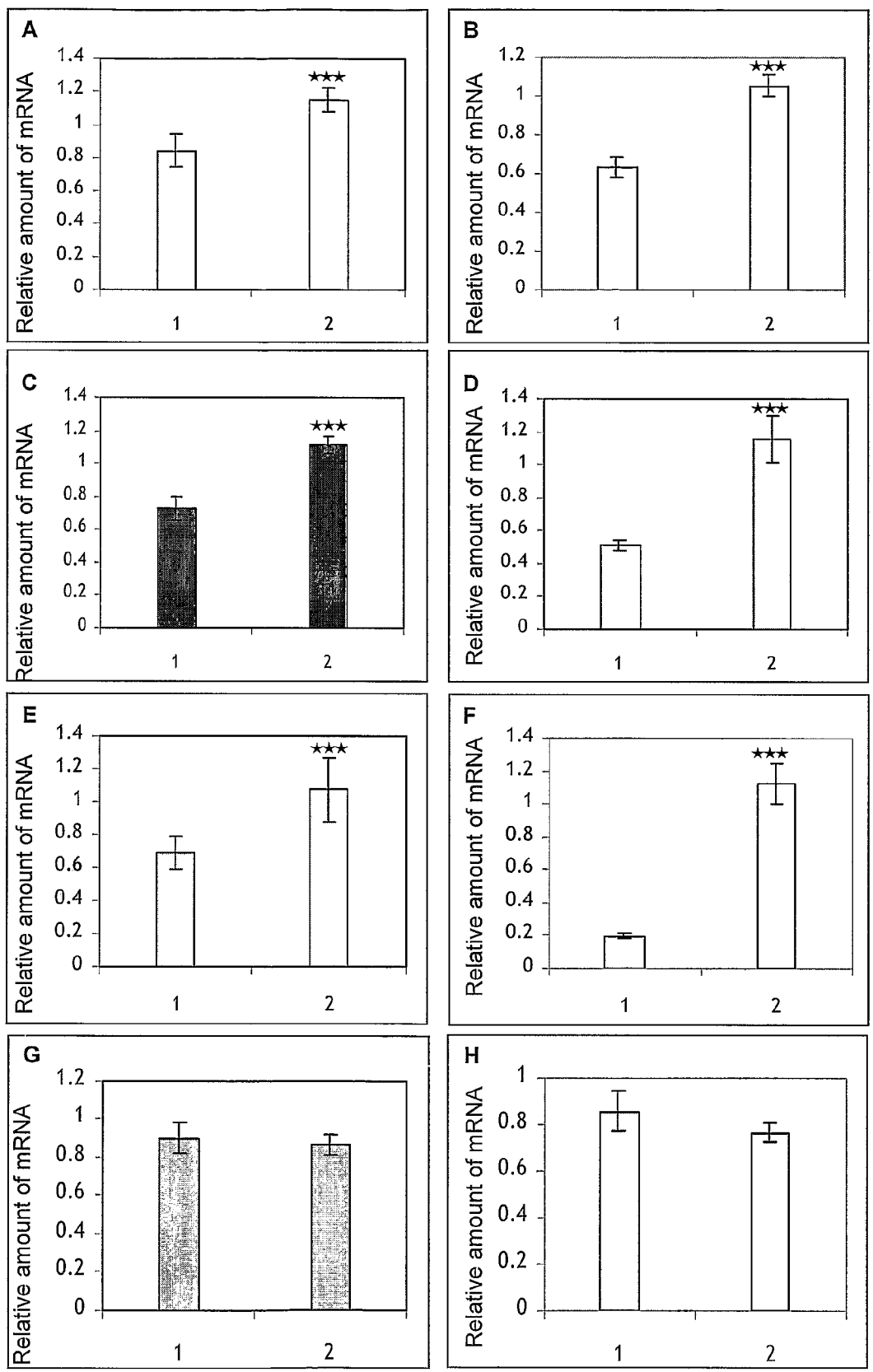
FIG. 20: Relative amount of mRNAs for genes up-regulated by microarray analysis in GL261-233R (lane 2) compared to GL261-233RC (lane 1) cells as detected by Real Time PCRs. A. RapGEF2 (fold change: 1.36; p<0.001). B. PAK3 (fold change: 1.66; p<0.0001). C. Fos (fold change: 1.53; p<0.0001). D. FosL2 (fold change: 2.28; p<0.001). E. PVR (fold change: 1.55; p<0.01). F. AFAP (fold change: 5.67; p<0.0001). G. GAPDH (Control gene). H. Tubulin 2 (Control gene). Bars represent means±SD.
Figure 21:
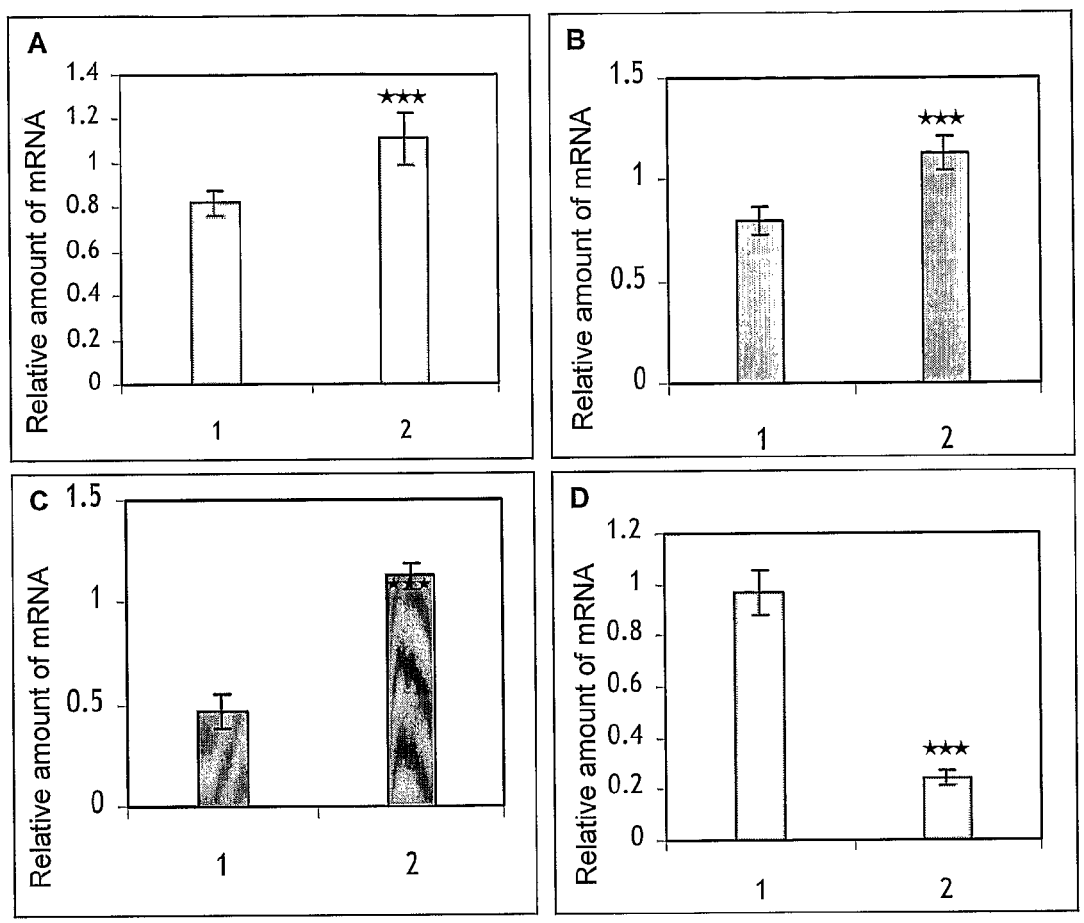
FIG. 21: Relative amount of mRNAs for genes up-regulated or down-regulated by microarray analysis in GL261-233R (lane 2) compared to GL261-233RC (lane 1) cells as detected by Real Time PCRs. A. BDNF (fold change: 1.35; p<0.01). B. Tspan6 (fold change: 1.41; p<0.001). C. Ptgfrn (fold change: 2.39; p<0.0001). D. VLDLR (fold change: 0.25; p<0.0001). Control genes are shown in FIG. 21. Bars represent means±SD.

To validate our microarray data and hypothesis on the significance of JAM-C expression for glioma cell malignancy, we first confirmed the upregulation and downregulation of different genes in GL261-233R cells by Real Time PCR. Five different RNA samples for each of the two GL261-233R and GL261-233RC cell lines were used to perform quantitative PCRs. As shown in FIG. 20 and FIG. 21 all the genes differentially expressed by microarray analysis showed similar pattern of expression by Real Time PCR. Furthermore among these genes the mRNA levels of the AFAP gene were significantly higher in the GL261-233R cell line than in GL261-233RC as detected by Real Time PCR (fold change: 5.67) than by microarray analysis (fold change: 1.97). These results confirmed the hypothesis that high levels of JAM-C expression on the membrane of glioma cells might cause a cascade of intra-cellular signals mediated by an active c-Src proto-oncogene affecting several cellular behaviours that are crucial for glioma development.

Example 7

Over-Expression of JAM-C in Glioma Cells Activates the c-SRC Proto-Oncogene

The c-Src proto-oncogene, the cellular counterpart of the v-SRC Rous Sarcoma Virus, is the prototype of a family of non-receptor tyrosine kinases including Lyn, Fyn, LcK, HcK, Fgr, Blk and Yes. c-Src kinase activity is regulated by several mechanisms comprising phosphorylation at specific tyrosine residues. In particular tyrosine 419 (in the human protein) or tyrosine 408 (in the mouse protein) is autophosphorylated when c-Src is recruited to the cell membrane and is essential for full c-Src kinase and transforming activity.

Recruitment of c-Src to the cell membrane is induced by active RTKs, through direct protein-protein binding, by adhesion molecules at sites of cell-extracellular matrix contacts and cell-cell contacts. Therefore, we hypothesised that in our GL261-233R cells elevated levels of JAM-C at the cell membrane could enhance homophilic and/or heterophilic JAM-C adhesive interactions and thus provoke recruitment and activation of c-Src. Several possibilities could be envisaged. First, JAM-C could be engaged in homophilic trans-interactions, given the abundance of JAM-C on the surfaces of GL261-233R adjacent cells. Second, JAM-C could establish heterophilic trans-interactions, for example with its homolog JAM-B or other members of the same IgSf (including the up-regulated PVR in GL261-233R cells). Third, JAM-C could establish in cis associations possibly with integrins, since this has already been shown for its homolog JAM-A protein with $\alpha_v\beta_3$ integrin in endothelial cells, and microarray analysis showed expression of mRNAs for several integrins in GL261-233R cells. Finally all these types of protein-protein connections might increase either the levels of total c-Src protein or/and the state of its activation.

Figure 22:
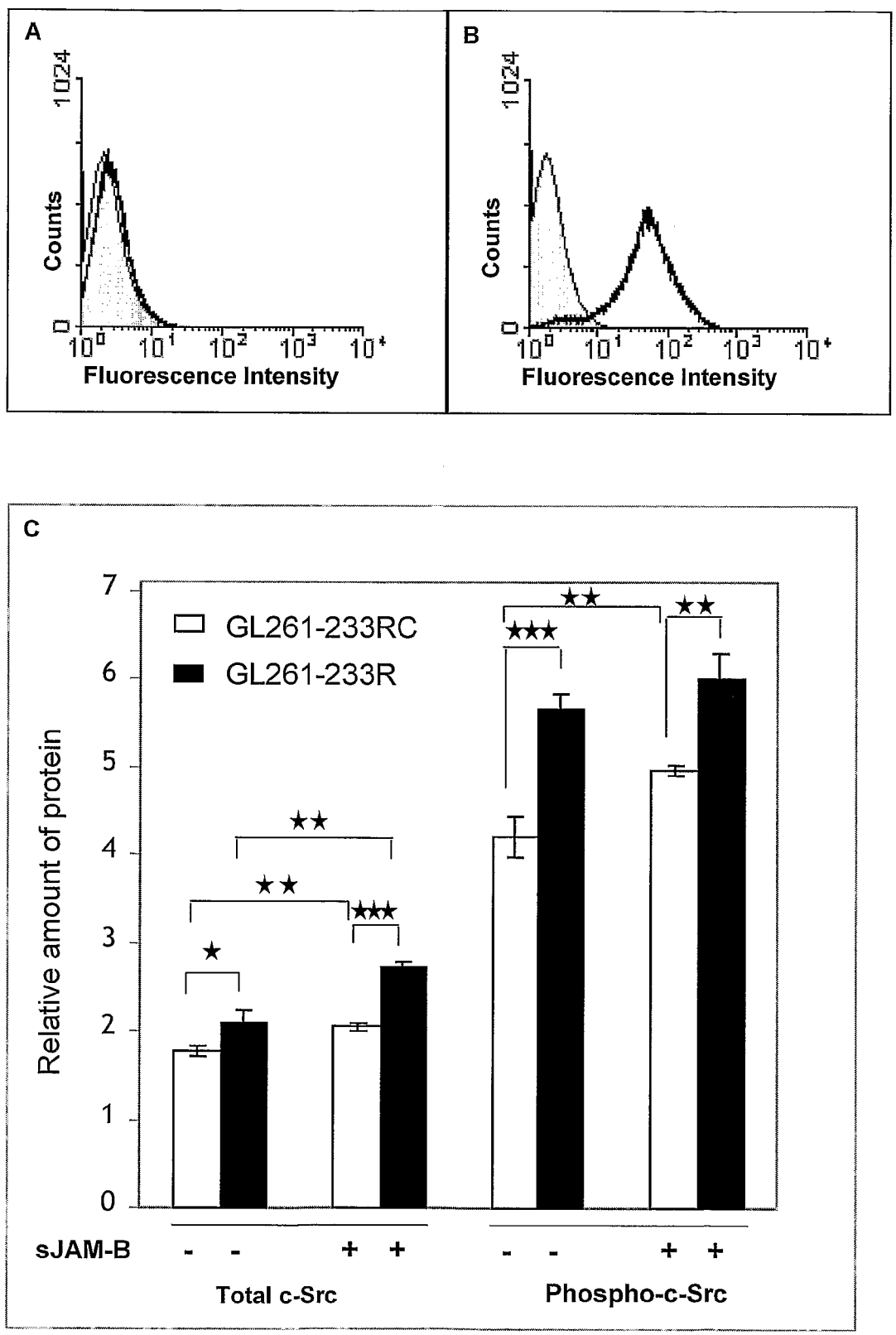
FIG. 22: Overexpression of JAM-C and its trans-interaction with JAM-B in glioma cells activate the c-Src proto-oncogene. A. Flow cytometry analysis of soluble JAM-B binding to the surface of GL261-233RC JAM-C knock-down cells. The histogram shows the profile obtained by incubating the cells with sJAM-B-Fc chimera and secondary anti-human Fc antibody (black open curve) and the secondary anti-human Fc antibody only (gray-filled curve). B. Flow cytometry analysis of soluble JAM-B binding to the surface of GL261-233R JAM-C rescued cells. The histogram shows the profile obtained by incubating the cells with sJAM-B-Fc chimera and secondary anti-human Fc antibody (black open curve) and the secondary anti-human Fc antibody only (gray-filled curve). C. Quantification of total levels of c-Src protein and active phosphorylated c-Src in GL261-233R (black bars) and GL261-233RC (white bars) cells and in the same cells upon exposure to sJAM-B-Fc chimera protein. GL261-233R cells show significant higher levels of c-Src protein and active phopshorylated c-Src compared to GL261-233RC cells. Exposure of GL261-233RC and GL261-233R cells to a sJAM-B protein causes increases in c-Src protein levels but to a significant higher extent in JAM-C over-expressing GL261-233R cells. sJAM-B protein causes increases in phosphorylated c-Src protein levels in GL261-233RC cells. Bars represent means±SD. (One asterisk: p=0.02; two asterisks: p≦0.005; three asterisks: p<0.001).

To test this hypothesis we analysed the amount of total c-Src protein and the degree of its phosphorylation at the activating tyrosine 408 in GL261-233RC and GL261-233R cells by ELISA.
Results GL261-233R cells expressing high levels of JAM-C showed significant higher levels of total c-Src protein as compared to the GL261-233RC JAM-C knocked down cells (FIG. 22). Furthermore, the amount of active phosphorylated c-Src protein was also significantly higher in GL261-233R cells compared to GL261-233RC cells (FIG. 22). These findings suggested that high JAM-C expression at the surface of glioma cells results in increased levels and kinase activity of the c-Src proto-oncogene. Since our expression analysis demonstrated that not only JAM-C but also its homolog protein JAM-B was highly and abnormally expressed in glioma cells of both human and mouse origin, we thought that this increased expression might find at least in part a reason in that trans-interaction between JAM-C and JAM-B could also result in increased c-Src levels and/or activity. Therefore, the amount of total and 408 tyrosine phosphorylated c-Src protein were analysed in GL261-233RC and GL261-233R cells after exposure to a chimeric soluble JAM-B protein. Soluble JAM-B increased the levels of total c-Src protein in both GL261-233RC and GL261-233R cells, but in these last one to a much higher extent. Moreover, soluble JAM-B augmented also the levels of active phosphorylated c-Src, but in this case a significant increase was observed only in GL261-233RC cells. This suggests that the levels of phosphorylated c-Src present in GL261-233R cells might be saturating and therefore a further increase by soluble JAM-B can only occur in GL261-233RC cells which express background levels of JAM-C.

Overall, these findings suggest that high levels of JAM-C expressed on the membrane of glioma cells result in c-Src increased protein amount and activation. This could theoretically be the result of homophilic trans-interactions of JAM-C on juxtaposing cells, of JAM-C cis-interactions with integrins or JAM-C trans-interactions with JAM-B, which we demonstrated to be expressed by GL261 glioma cells. This last mechanism is likely to be involved as demonstrated by the increase in c-Src protein levels and activation in GL261-233RC cells and in c-Src protein levels in GL261-233R cells.

Example 8

Determination of Binding Characteristics of the JAM-C Binding Antibody D33 by Surface Plasmon Resonance The surface plasmon resonance assays were performed on a BIAcore 2000 instrument using a CM5 sensor chip (Biacore AB), and kinetic parameters were determined with the manufacturer's BIAevaluation 4.1 software. The chip surface of flowcell 3 and 4 was first activated by injection of 50 µl of a 1:1 mixture of 0.1 M N-hydroxysuccinimide and 0.4 M N-ethyl-N'-(dimethylaminopropyl)carbodiimide.

Soluble flag-tagged recombinant human JAM-C protein (up to the QEMEV sequence) was produced in BOSC cells and purified through an anti flag column. Purified recombinant human flag-tagged JAM-C (at a concentration of 1 µg/ml) was immobilized at a flow rate of 20 µl/min in sodium acetate pH 5.0 at 25° C. onto flow cell 4 of the CM5 sensor chip. Remaining active groups on the chip were blocked with 1 M ethanolamine-HCl pH 8.5. The immobilization resulted in 155 resonance units (RUs) for human flag-tagged JAM-C.

Monoclonal antibody D33 was injected at concentrations ranging from 1 to 100 µg/ml (6.67-667 nM) in 50 µl HBS-EP buffer [0.01 M HEPES (pH 7.4), 0.15 M NaCl, 3 mM EDTA, 0.005% surfactant P20] at a flow rate of 20 µl/min. Samples were injected for 150 seconds, dissociated for 100 seconds, regenerated for 60 seconds using 10 mM 5 glycine at pH 1.5 and then stabilized for about 1 min before the next injection. The analyte was simultaneously passed over a blank flow cell, and this baseline was subtracted from the experimental flow cell. The monoclonal antibody D33 was found not to interact with the blank flow cell.

Figure 28:
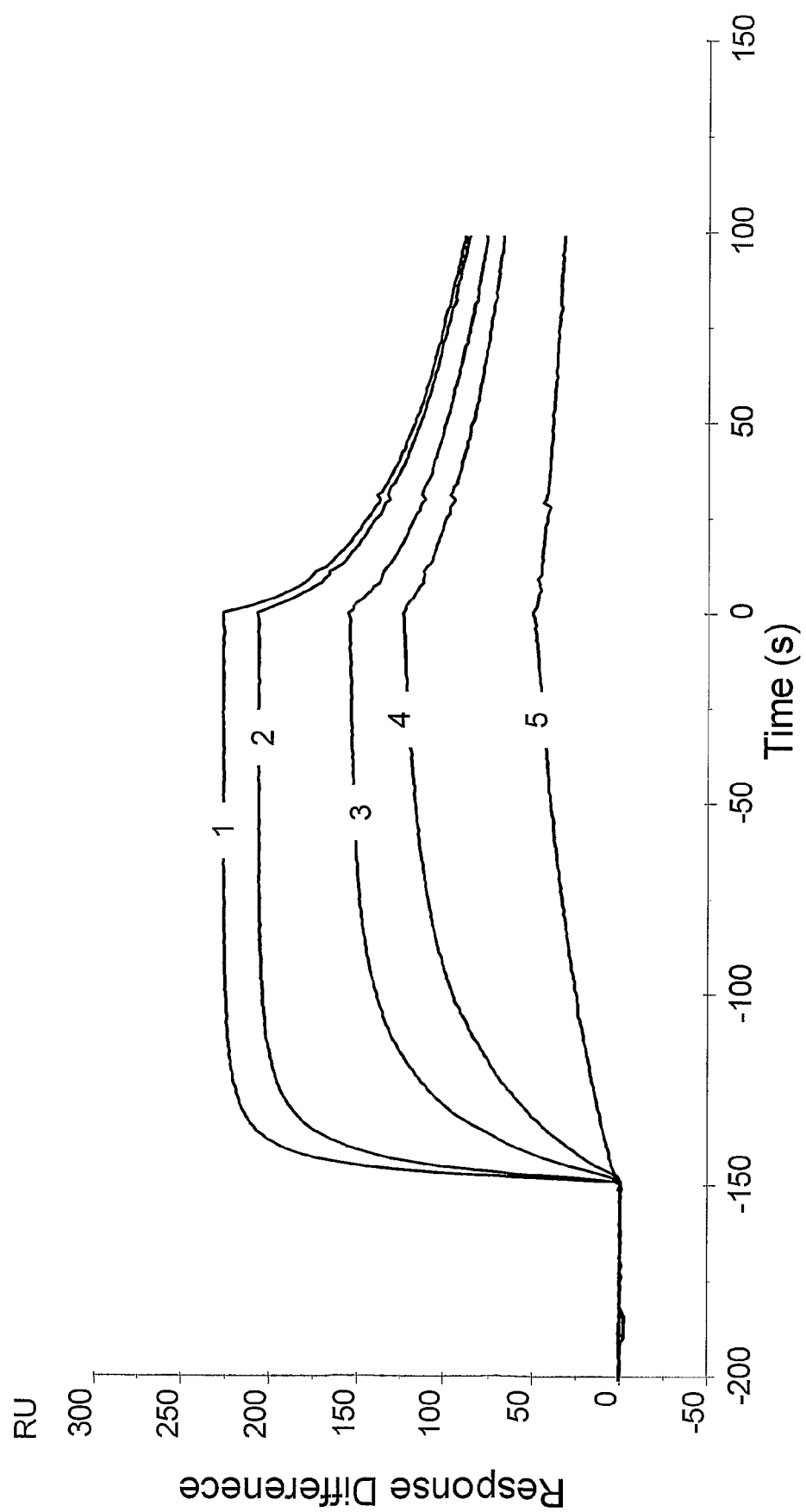
FIG. 28 Binding characteristics of antibody JAM-C blocking antibody D33 were determined by surface plasmon resonance assay on a BIAcore 2000 instrument. JAM-C blocking antibody D33 was used as analyte in different concentrations (1=666.5 nM; 2=333.3 nM; 3=66.66 nM; 4=33.33 nM and 5=6.666 nM) and flown over a chip coated with 155 resonance units (RUs) of JAM-C and an uncoated chip as a reference.
Figure 29:
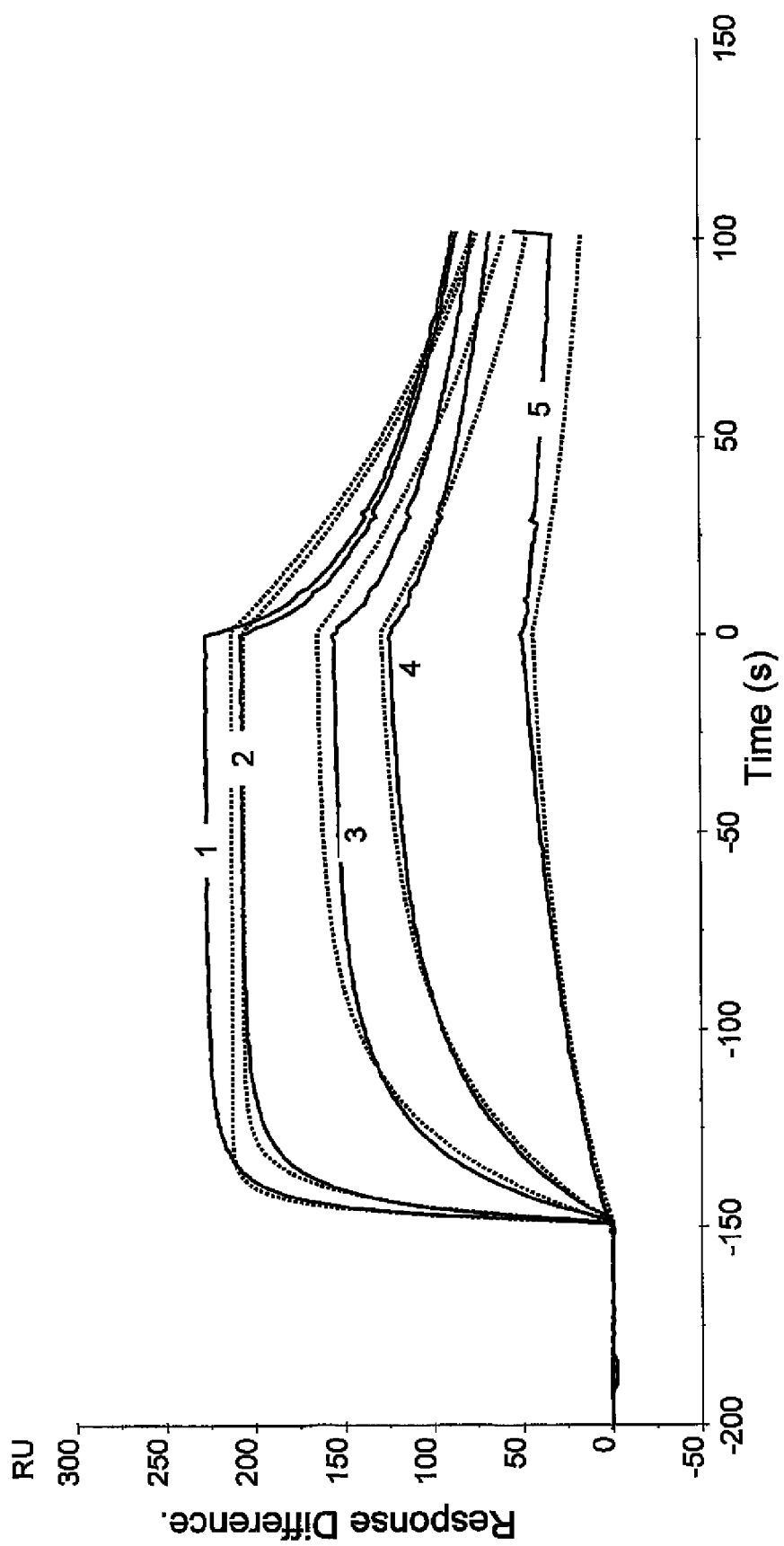
FIG. 29 The raw data of the of the surface plasmon resonance assay with the JAM-C blocking antibody D33 were analysed according to the 1:1 langmuir fit model. The analysis provides the affinity of the D33 antibody to the JAM-C antigen on the chip. Based on the 1:1 interaction the $k_a$, $k_d$ and $K_D$ constants can be calculated.
Figure 30:
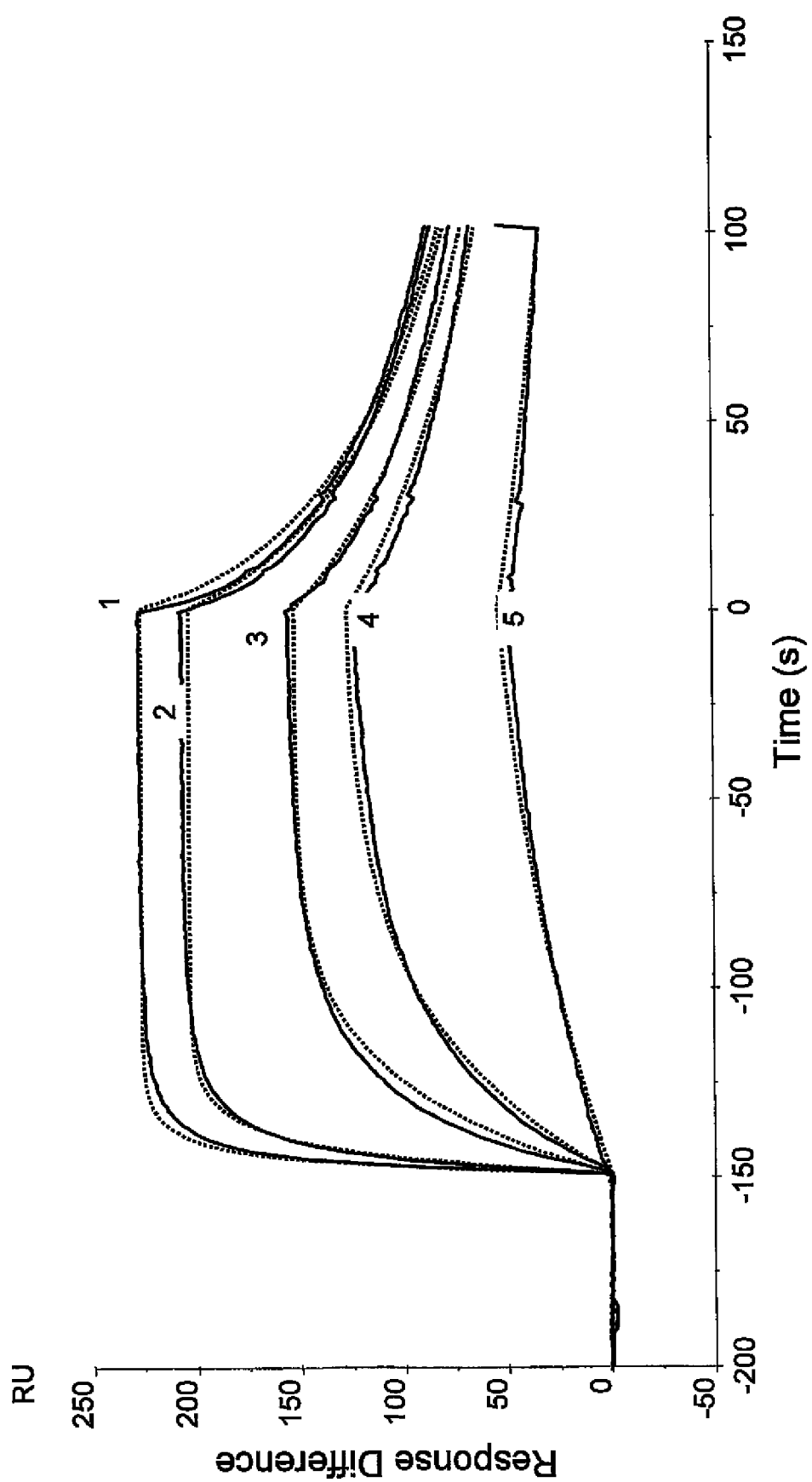
FIG. 30 The raw data of the of the surface plasmon resonance assay with the JAM-C blocking antibody D33 were analysed according to the bivalent fit model which takes into consideration the bivalent nature of the antibody.

The results are shown in Tables 7 to 9. After subtraction of each response value from the control cell, association and dissociation rate constants were determined by simultaneous $K_a/K_d$ calculation of the binding and dissociation curves using global data analysis (FIG. 28). Calculation using 1:1 Langmuir model (FIG. 29) and bivalent model (FIG. 30) (BIAevaluation 4.1. BIAcore AB) was performed.

Results
A) 1:1 Langmur Fit

TABLE 7

| Sample | RI (RU) | Concentration of analyte (nM) | Response equilibrium (RU) | $k_{obs}$ (1/s) |
|---|---|---|---|---|
| 1 | 0 | 1333 | $2.13 \times 10^2$ | $3.17 \times 10^{-1}$ |
| 2 | 0 | 666.7 | $2.06 \times 10^2$ | $1.63 \times 10^{-1}$ |
| 3 | 0 | 133.33 | 165 | $4.09 \times 10^{-2}$ |
| 4 | 0 | 66.67 | $1.32 \times 10^2$ | $2.56 \times 10^{-2}$ |
| 5 | 0 | 13.33 | 50.6 | $1.33 \times 10^{-2}$ |

TABLE 8

| $k_a$ (1/Ms) | $k_d$ (1/s) | $R_{max}$ (RU) | $K_A$ (1/M) | $K_D$ (M) | $Chi_2$ |
|---|---|---|---|---|---|
| $2.30 \times 10^5$ | $1.02 \times 10^{-2}$ | $2.20 \times 10^2$ | $2.24 \times 10^7$ | $4.46 \times 10^{-8}$ | $8.75 \times 10^1$ |

B) Bivalent Fit

TABLE 9

| Sample | $k_{a1}$ (1/Ms) | $k_{d1}$ (1/s) | $k_{a2}$ (1/RUs) | $k_{d2}$ (1/s) | $R_{max}$ (RU) | RI (RU) | Concentration of analyte (nM) | $Chi_2$ |
|---|---|---|---|---|---|---|---|---|
|   | $1.26 \times 10^5$ | 0.0571 | $4.07 \times 10^{-3}$ | 0.0616 | 383 |   |   | 12.2 |
| 1 |   |   |   |   |   | 0 | 666.5 |   |
| 2 |   |   |   |   |   | 0 | 333.3 |   |
| 3 |   |   |   |   |   | 0 | 66.66 |   |
| 4 |   |   |   |   |   | 0 | 33.33 |   |
| 5 |   |   |   |   |   | 0 | 6.666 |   |

The dissociation constant $k_d$ of monoclonal antibody D33 as determined by surface plasmon resonance using solid phase JAM-C and the monoclonal antibody D33 as analyte is about $10^{-2}$ s$^{-1}$ to $5 \times 10^{-2}$ s$^{-1}$.

Summary of the Results Obtained in the Examples

Here we have demonstrated that JAM-C and JAM-B are abnormally expressed by glioma tumour cells. Whilst some tumours exhibited diffuse overexpression of JAM-C and/or JAM-B, intra-tumour heterogeneity was also observed, with tumour cells expressing high levels of JAM-C or JAM-B on their membranes, and tumour cells that appeared not to express the proteins. This heterogeneity might reflect the intrinsic nature of gliomas, which show a very high genetic instability resulting in the presence of different clonal populations within a single tumour. However, intra-tumour heterogeneity for JAM-C and JAM-B expression might also suggest that JAM-C and JAM-B can be up-regulated by single tumour cells that activate specific cellular processes. For example, as discussed in the introduction, glioma cells migrate and invade as single cells, already in early stages of malignancy. This implies that these isolated cells have to activate cellular processes as adhesion, cytoskeleton rearrangements and extracellular matrix degradation. Up-regulation of JAM-C or JAM-B on single glioma cells might therefore reflect the specific functions that those cells are accomplishing in the more general context of the tumour. No correlation was found with tumour grade, suggesting that up-regulation of JAM-C and JAM-B might occur early during tumour development.

The importance of JAM-C expression by glioma for its in vivo development was explored using the GL261 mouse glioma model. We demonstrated that GL261 cells, which show typical features of human glioblastoma, express high levels of JAM-C on their membranes. An anti-JAM-C antibody treatment had a partial inhibitory effect on heterotopically growing GL261 gliomas which was most likely the consequence of partial inhibition of tumour associated angiogenesis. In contrast, anti-JAM-C antibody treatment had a very significant inhibitory effect on orthotopically growing GL261 gliomas. In this case we observed inhibition of tumour-associated angiogenesis as for subcutaneously growing tumours, but in addition the spreading of the tumour in the normal brain tissues was affected, as detected by a different tumour shape in the brain of mice which were treated with the anti-JAM-C antibody. This suggests that in the brain, the anti-JAM-C antibody affected not only tumour associated angiogenesis but also other cellular processes in particular glioma spreading.

We have then demonstrated by gene expression analysis of GL261 glioma cells differentially expressing JAM-C that the overexpression of this protein on the surface of glioma cells up-regulates a series of genes that are effectors of signalling cascades important for tumour development. In particular, we have detected up-regulation of genes downstream to the MEK-ERK pathway (Fos, FosL2 and PVR) and of effectors of the Rho family small GTPases pathway (RAPGEF2, PAK3).

A crucial molecule up-stream of these cascades is the c-Src proto-oncogene. Indeed we have demonstrated that overexpression of JAM-C by glioma cells causes an increase in c-Src protein levels and activation. In addition, since activation of c-Src is an event that can occur as a consequence of adhesion contacts, we have shown that adhesive interactions between JAM-C on the surface of glioma cells and soluble JAM-B provoke an augmentation of c-Src protein levels, indicating that the up-regulation of both molecules might significantly contribute to glioma malignancy.

Overall these findings raise several important biological questions. In particular, our expression analysis of JAM-C in human gliomas suggests that JAM-C might be localised at sites of cell-cell contacts and on the entire cell membrane. Therefore, it is not clear how the cellular distribution of JAM-C might be regulated and what might be the biological significance of different sub-cellular localisations.

In addition, our findings suggest that high levels of JAM-C on the surface of glioma cells might represent a significant advantage for the achievement of a cancerous phenotype. This raises the question of how JAM-C might impact on the behaviours of glioma cells and possibly also of their extracellular environment, for example by inducing tumour associated angiogenesis.

Furthermore, our results suggest that JAM-C, expressed by either glioma tumour cells and/or endothelial cells, might be important for glioma associated angiogenesis. This raises the question of whether and how JAM-C expressed by glioma cells might have any effect on the process of neovascularisation and how JAM-C expressed by endothelial cells might function in the regulation of this process.

Finally, our data show that targeting JAM-C with an anti-JAM-C antibody has different outcomes in glioma growth inhibition when the tumour is grown subcutaneously or intracerebrally. This raises the question of how JAM-C expressed by glioma cells might act in different environmental contexts and how it might translates to the cells important cues coming from these diverse contexts affecting the development of the tumour.

Several hypotheses can be formulated to answer these multiple questions.

Sub-cellular Localisation of JAM-C.

Analyses of JAM-C sub-cellular distribution have been performed on MDCK cells ectopically expressing JAM-C. In these cells JAM-C was shown to co-localise to tight junctions with Occludin or ZO-1 by confocal microscopy analysis (Aurrand-Lions et al., 2001a). This distribution is consistent with JAM-C function in tight junction formation and maintenance of cell polarity. However, in intestinal epithelial cells JAM-C was shown to colocalise with desmoplakin in desmosomal structures, suggesting that in these cells JAM-C might be involved in functions different from tight junction formation and cell polarity. Since to date no analysis of JAM-C expression and sub-cellular localisation have been reported on tumour cells, it is not known whether the cellular distribution of JAM-C in normal and transformed malignant cells might be similar. Here we have observed JAM-C expression on glioma cells at both sites of cell-cell contacts and on the entire cell membrane by immunohistochemistry and immunofluorescence. Our data, although requiring further confirmation by confocal microscopy analysis, suggest that in glioma tumour cells JAM-C might have different sub-cellular localisations. Whether this reflects a peculiarity of glioma cells or of cancer cells in general and whether it is linked to particular functions of JAM-C in these cells remains to be clarified. However, we can suppose that the activation of certain signalling pathways in cancer cells might cause a redistribution of JAM-C from tight junctions to other sites of the cell membrane where JAM-C might play functions different form tight junction formation or maintenance of cell polarity. Indications already exists that JAM-C serine phosphorylation regulates its membrane localisation. We suppose that stimuli causing intracellular signals that activate protein kinases or phosphatases might alter the state of JAM-C phosphorylation at specific aminoacid residues and displace it from tight junctions. It is known that the pro-inflammatory cytokines TNFα and IFNα and the VEGF provoke redistribution of JAM-A and JAM-C, respectively, on the membrane of endothelial cells. In addition, it has been shown that Hepatocyte Growth Factor (HGF), which is implicated in breast cancer cell metastasis, disrupts tight junctions in these cells by modulating expression of tight junction proteins, including JAM-A, and causing tyrosine phosphorylation of ZO-1. This suggests that the signals that are triggered downstream of cytokines or growth factors may cause a change in JAM-C sub-cellular localisation.

Another mechanisms through which JAM-C localisation at tight junctions might potentially be regulated could be by changes in intracellular binding partners. In particular the cytoplasmic tight junction protein AF6, which interacts with JAM-A, harbours a binding site which can be competitively occupied by either the tight junction protein ZO-1 or Ras and the Rho family small GTPases protein Rap-1. This suggests that the integrity of tight junctions can be perturbed by signals that activate Ras or Rap-1 and that promote their binding to AF6. This would release ZO-1 and potentially JAM-A from tight junction structures. Whether JAM-C can associate with AF6 and function in a way similar to JAM-A is not known, but the high homology between JAM family members suggest that this might occur.

The potential regulation of JAM-C cellular distribution by growth factors and Rho family small GTPases is intriguing and strongly suggests that the intracellular pathways activated in gliomas might significantly influence the localisation of this protein in the cell.

Overall, we can suppose that the constitutive activation of pathways crucial for tumour development through genetic abnormalities would possibly disrupt the integrity of tight junctions. In this way tumour cells would not only detach from adjacent cells, which is necessary for motility and invasion but also make JAM-C available for functions implicated in cancer development and progression, such as cell adhesion, dissemination and stimulation of angiogenesis.

Mechanisms of JAM-C Action on Glioma Tumour Cells

So far, the adhesion molecule JAM-C has not been the subject of thorough investigations in human cancers. No conclusive data are available concerning its expression or possible functions in malignant cells. Here, we have observed an abnormal up-regulation of JAM-C expression in glioma cells and we provided evidence that this is of significant relevance for several malignant functions of the tumour cell itself and for the induction of changes in its environment necessary for its expansion. Several mechanisms can be hypothesised through which JAM-C might have such an impact on the biology of glioma.

It is well established that JAM-C can engage in homotypic trans-interactions and in heterotypic trans-interactions with JAM-B. In addition, heterotypic trans-interactions between JAM-C and leukocyte integrins and heterotypic cis-interactions between JAM-A and integrin $\alpha_v\beta_3$ have been reported. We therefore hypothesise that over-expression of JAM-C by glioma cells might lead to multiple adhesive contacts, namely JAM-C-JAM-C and JAM-C-JAM-B on opposing glioma cells, and between JAM-C and integrins on the surface of glioma cells. The result of these adhesive contacts would be the recruitment and activation of the proto-oncogene c-Src at the cell membrane of glioma cells over-expressing JAM-C. This would be mediated at least in part by Actin Filament Associated Protein (AFAP). AFAP was first identified as a binding partner for c-Src. In addition, AFAP contains several protein binding modules and interacts with actin filaments directly serving as a platform for the construction of larger signalling complexes. AFAP activates c-Src in response to cellular signals that alter its conformation.

The consequences of activating c-Src by glioma cells are multiple and can have a strong impact on glioma malignant behaviour.

Figure 23:
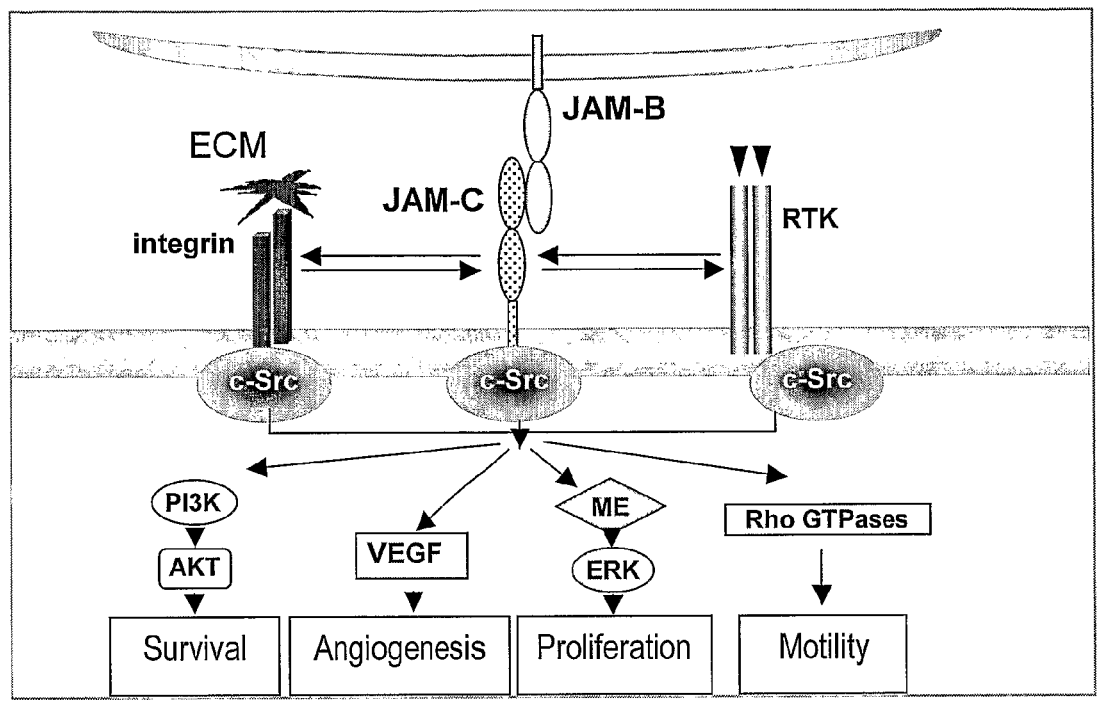
FIG. 23: Model of JAM-C function in glioma cells. JAM-C (white, dotted globular structure) on the membrane of a glioma cell establishes multiple adhesive contacts: in trans with JAM-B (light grey globular structure) on the surface of an opposing cell, in cis with integrins (dark grey parallelepipeds) and in cis with RTKs (white/black parallelepipeds). The result of these multiple interactions and of integrins binding to their extracellular matrix ligands and RTKs stimulation by growth factors is the recruitment and activation of the c-Src non receptor tyrosine kinase at the cell membrane. C-Src activates crucial intracellular pathways leading to increased cell survival, proliferation, induction of angiogenesis and motility/invasion.

Aberrant high levels of c-Src have been reported in a variety of human cancers including astrocytomas (Takenaka et al., 1985). In addition, c-Src activity can be predictive of poor prognosis (Aligayer et al., 2002). A large array of cellular stimuli, including those derived by growth factors, integrin aggregation and adhesive cell-cell contacts lead to the phosphorylation of signalling molecules that are bound by c-Src through its SH2 domain. This binding changes c-Src conformation and phosphorylation state thereby provoking its activation. In the active state c-Src can then associate with structural and signalling proteins resulting in the stimulation of a range of cellular processes comprising cell survival, proliferation, angiogenesis and invasion. As depicted in FIG. 23, c-Src is a master up-stream activator of pathways that are aberrantly stimulated during gliomagenesis and progression, namely the Ras-Raf-MEK-ERK, the PI3K-AKT and the Rho small GTPases pathways. The significance of c-Src activation for glioma development and progression has been demonstrated with transgenic mouse models where the expression of the v-Src gene, the viral constitutively active counterpart of cellular c-Src, was targeted to astrocytes. The majority of the mice showed dysplastic changes of astrocytes and 15% of them developed astrocytomas which further progressed to glioblastoma. In addition, the authors observed co-localised expression of v-Src and VEGF in the neoplastic lesions. These data indicate that c-Src activation can significantly contribute to the progression of astrocytomas. Furthermore, other authors have observed that the orthotopic dissemination of gliomas in c-Src deficient mice was significantly impaired suggesting that c-Src might be relevant for glioma spreading in the brain.

Overall these data imply that overexpression of JAM-C on glioma cells and consequent activation of c-Src finds its reason in the enhancement of the same cascade of signals that are already activated by glioma cells through other means, for example through activation of RTKs. This results in a significant contribution of JAM-C to the malignant behaviour of glioma cells. In particular, our findings strongly suggest that increased levels and kinase activity of c-Src as a consequence of JAM-C overexpression by glioma cells significantly contributes to their invasive properties in the brain and potentially to the stimulation of angiogenesis, the two major malignant features of high grade astrocytoma. In addition, as experimentally demonstrated, over-expression of JAM-B on glioma cells can further increase c-Src levels by interacting with JAM-C on opposing cells thereby augmenting these cascades of malignant processes.

The mechanisms through which JAM-C might contribute to glioma cell invasion in the brain could potentially implicate not only interactions between JAM-C and JAM-B on adjacent cells but also of in cis associations of JAM-C and integrins on the surface glioma cells. Indeed, in cis interactions of JAM-A and integrin $\alpha_v\beta_3$ on endothelial cells have already been demonstrated to be relevant to their migration on vitronectin. In addition, the IgSf molecule PVR, whose expression is augmented in JAM-C over-expressing glioma cells, also co-localises with integrin $\alpha_v\beta_3$ at the leading edge of migrating cells and is strongly involved in glioma invasion on vitronectin. Integrin $\alpha_v\beta_3$ is highly expressed by glioma tumour cells especially at the advancing tumour margin. Indeed this integrin contributes to the process of cell invasion not only by promoting adhesion and migration of tumour cells on the ECM but also by regulating the localisation and activation of proteases at the leading edge of the migrating cell. Therefore, interactions of JAM-C with integrin $\alpha_v\beta_3$ could be envisaged and would have a strong impact on glioma cell invasion.

Indications that JAM-C might participate in integrin signalling comes our observation that Tspan6, Ptgfrn and Eps8 are the up-regulated in JAM-C over-expressing glioma cells.

Tspan6 belongs to the family of tetraspanin trans-membrane proteins that form large clusters on the cell surface by simultaneously engaging in associations with other members of their own family, a variety of integrins and other adhesion molecules. These clusters function as organising platforms to translate numerous extracellular stimuli to the cell by means of tetraspanin intracellular association with signalling molecules, including cytoskeleton proteins. Tetraspanins have been shown to modulate integrin-dependent activities like adhesion strengthening and migration. Several tetraspanins have been linked to progression and metastasis of a variety of tumor types. The Ptgfrn is one tetraspanin molecular partner belonging to the IgSf family of proteins. It might be possible that JAM-C might be engaged in tetraspanin clusters and this might facilitate cooperation between JAM-C and integrin signalling.

The association and synergy with integrin signalling is also suggested by the up-regulation in JAM-C over-expressing glioma cells of Epidermal-growth factor substrate 8 (Eps8). Eps8 is a target of EGF-R-mediated phosphorylation involved in cell proliferation and malignancy. It was shown that accumulation of Eps8 occurred upon integrin aggregation and ligand binding and EGF stimulation. In this work the authors demonstrated that the increases in Eps8 levels were the result of a synergistic collaboration between RTKs and integrin signalling through the MAPK-ERK pathway. The up-regulation of Eps8 in JAM-C over-expressing glioma cells might indicate that JAM-C may be involved in the cascade of integrin signals and crosstalk with RTKs. Since our gene expression analysis was performed on in vitro cultured cells it is possible that this cascade is significantly more activated in vivo where integrin extracellular matrix ligands are present.

Gene expression analysis of JAM-C overexpressing glioma cells showed increased mRNA levels of Fos and FosL2. This might potentially be another way through which JAM-C might add to the malignant phenotype of glioma, cells. c-Fos and FosL2 are proto-oncogenes that by dimerisation with Jun proteins form the AP-1 transcription factor. AP-1 recognises specific responsive elements in the promoter of target genes. AP-1-induced genes comprise important regulators of cell proliferation, such as cyclins, of apoptosis or invasion, including MMPs and uPA/uPAR, and of angiogenesis such as VEGF. Multiple oncogenic signalling pathways converge on the AP-1 transcription factor. The transforming activity of c-Fos has been recognised in a variety of cancers and increased expression of Fos family members appears as an important step in tumour progression. FosL2, albeit ineffectively triggering oncogenic transformation, is abundant in Ras-and Src-transformed murine and chicken fibroblasts, and it has been suggested to function in the maintenance and progression of the transformed state. Although the levels of up-regulation of Fos and FosL2 in glioma cells over-expressing JAM-C were not very high as detected by microarray and Real Time PCR analysis, we suppose that in vivo, where the same cells can find their appropriate extracellular matrix ligands, the intensity and duration of the intracellular signals that lead to Fos and FosL2 expression might be significantly enhanced. Fos and FosL2 expression can occur downstream of the MAPK-ERK pathway, which as mentioned above can be synergistically activated by integrins engaged in associations with their extracellular matrix ligands and stimulation of RTKs by their growth factors. Therefore, the potential implication of JAM-C in the crosstalk between integrins and RTKs, as discussed above, might result in significant activation of their signals in the in vivo environment and in increased levels of expression of Fos family members. Fos proteins, by virtue of their large spectrum of target genes implicated in the neoplastic process would potentially enhance the malignancy of glioma.

Mechanisms of Anti-JAM-C Antibody Inhibition of Tumour-Associated Angiogenesis

Our data have shown that an anti-JAM-C antibody reduced angiogenesis associated to the GL261 mouse glioma grown both subcutaneously or intra-cerebrally, although without reaching the levels of significance. Similar findings have been reported with another ant-JAM-C antibody which reduced the in vivo neovascularisation associated to a mouse Lewis Lung Carcinoma (Aurrand-Lions et al., 2001a; Lamagna et al., 2005a). The authors attributed this anti-angiogenic effect to the impairment in macrophages recruitment to the tumour mass. Macrophages secrete a variety of pro-angiogenic factors that can significantly promote the process of angiogenesis. It is possible that in our glioma model, the recruitment of a monocyte/macrophage population to the tumour bed might have been affected by the treatment with the anti-JAM-C antibody. This is certainly an interesting topic requiring further investigations. However, targeting JAM-C on both glioma cells and endothelial cells with the anti-JAM-C antibody could inhibit angiogenesis by several other mechanisms.

The activation of c-Src through overexpression of JAM-C by glioma cells has direct consequences on the production of VEGF by the tumour cells. c-Src activation has been shown to be required for hypoxia-induced VEGF synthesis by activating STAT3 which forms a complex with HIF-1 on the promoter of VEGF. Inhibition of c-Src in colon carcinoma cells inhibited VEGF expression and tumour growth. Furthermore, c-Src was shown to regulate the expression of Interleukin-8 (IL-8), a potent tumorigenic and proangiogenic factor in gliomas. Accordingly, pharmacologic inhibition of c-Src kinase activity inhibited VEGF and IL-8 expression and angiogenesis. These findings underscore the importance of c-Src for the production of angiogenic factors by tumour cells and the relevance of targeting c-Src for tumour development. It is possible that JAM-C over-expressed by glioma cells by means of its in vivo adhesive contacts might induce increased angiogenesis by stimulating VEGF production via activation of c-Src, especially in hypoxic areas of the tumour. In this case the anti-JAM-C antibody might reduce the in vivo expression of VEGF by blocking JAM-C mediated activation of c-Src in glioma cells.

On the other hand targeting JAM-C expressed by endothelial cells with the anti-JAM-C antibody could also affect angiogenesis by similar mechanisms. Indeed, endothelial cells expressing a kinase-inactive c-Src were unable to spread and form tube-like structures, two processes fundamental for angiogenesis. Furthermore, several c-Src inhibitors were demonstrated to block endothelial cell sprouting and VEGF-induced permeability. In this context, the anti-JAM-C antibody directed against JAM-C on endothelial cells would prevent JAM-C induction of c-Src activation thereby blocking c-Src mediated angiogenic processes.

As discussed in the introduction, accumulating evidences in recent years suggest the existence of a crosstalk between VEGF/VEGF-R-2 and integrins in the process of angiogenesis stimulation. We speculate that JAM-C in endothelial cell might participate in this crosstalk. The above mentioned indications that JAM-C might be implicated in integrin signalling can be also applied to JAM-C expressed by endothelial cells. Potentially, under angiogenic stimuli JAM-C might associate with integrins important for angiogenesis and synergise in the signalling cascades induced and sustained by integrins cooperation with VEGF-R-2. The cis-association of integrin $\alpha_v\beta_3$ and JAM-A has already been reported and the crucial role played by JAM-A in transducing signals transmitted by bFGF to the MAPK-ERK pathway necessary for endothelial cell proliferation and migration was also shown. An involvement of JAM-C in VEGF and integrin signalling can therefore be supposed. In this case the anti-JAM-C antibody by targeting JAM-C expressed on endothelial cells would not only prevent c-Src mediated expression of VEGF but also interfere with important interactions between JAM-C, integrins and VEGF-R-2 thereby inhibiting their intra-cellular signals crucial for angiogenesis-related cellular processes.

Mechanisms of differential anti-tumour effect of anti-JAM-C antibody on heterotopically and orthotopically growing gliomas Our findings have shown that the growth of the GL261 mouse glioma overexpressing JAM-C can be significantly impaired by an anti-JAM-C antibody when the tumour is propagated in its natural environment. The growth impairment was much less pronounced when the GL261 mouse glioma grew in the non-natural environment of the subcutis. These results suggest that JAM-C is a crucial mediator in the translation to glioma cells of environmental stimuli that have a strong impact on their growth.

Several mechanisms could explain the more significant anti-tumour effect exerted by the anti-JAM-C antibody on orthotopically growing gliomas as compared to heterotopically growing gliomas.

The particular environment of the brain could transmit positive stimuli to glioma cells that could enhance their expansion. JAM-C expressed on the surface of glioma cells could be responsible for transmitting the positive cues coming from the surrounding brain environment through its capacity to communicate with the extracellular compartment through adhesive contacts and with the intracellular compartment through the recruitment of signalling molecules. In this case the growth of GL261 glioma intra-cerebrally would be more pronounced than subcutaneously and the action of an anti-JAM-C antibody would be more significant than subcutaneously where the same environmental stimuli would be absent. In particular the finding that the anti-JAM-C antibody inhibited the normal spreading of GL261 glioma cells in the brain suggests that JAM-C expressed by tumour cells is implicated in the processes of cell migration and invasion in the brain. Cell motility and invasion imply the establishment of adhesive contacts between the cells and the extracellular matrix that are largely mediated by integrins. In addition, integrin signalling upon engagement with the corresponding ligands are mediated by c-Src, which transduces not only signals necessary for cell migration but also positive stimuli for cell proliferation and survival (FIG. 23). It is possible that JAM-C might cooperate and synergise with integrins engaged in adhesions with particular brain extracellular matrix components. In this regard it of notice that a peptide blocking integrins $\alpha_v\beta_3$ and $\alpha_v\beta_5$ had a dramatic inhibitory effect on an orthotopic model of glioblastoma while it was ineffective on the growth of the same tumour in the subcutis (MacDonald et al., 2001). The authors suggested that the microenvironment, particularly the ECM composition and the ECM components specifically produced and deposited by the tumour cells in different organs, might be critical to glioma behaviour.

JAM-C interactions with other IgSf molecules present in the brain might also be possible and could sustain the same signalling cascade activated by integrins. As discussed above, this has been described for the Poliovirus Receptor (PVR/CD155), an IgSf molecule. According to this hypothesis the anti-JAM-C antibody would block JAM-C associations with adhesion molecules expressed in the brain, and integrins engaged in bindings with ECM constituents of the brain.

Another possibility for the differential outcome of anti-JAM-C antibody treatment on orthotopically growing GL261 gliomas compared to heterotopically grown tumours would be an involvement of JAM-C in BDNF signalling. We have detected an up-regulation of BDNF as a consequence of JAM-C overexpression by glioma cells. BDNF belongs to the family of neurotrophins and acts through the RTK receptor TRKB to promote the growth, survival and differentiation of developing and adult neurons in the nervous system. These effects seem to be at least in part the result of BDNF/TRKB induction of the PI3K-AKT pathway. In addition, it has been shown that BDNF can have an autocrine function whereby exogenous BDNF induces the expression of endogenous BDNF. BDNF is induced by the c-Fos oncogene in neuronal cells to regulate their survival. BDNF and its TRKB receptor have been shown to be overexpressed in human cancers particularly those with aggressive behaviours. In addition, BDNF trough TRKB-mediated activation of the PI3K-AKT pathway was shown to generate a potent pro-survival signal which rendered epithelial cells resistant to anoikis and conferred them highly invasive and tumorigenic capacities. Similar findings were reported for myeloma cells where BDNF and TRKB promoted tumour cell survival. BDNF is expressed by endothelial cells, increased upon hypoxia, and it elicits angiogenesis by promoting survival of endothelial cells and up-regulation of VEGF-R-2 expression. It is possible that in glioma cells overexpressing JAM-C, BDNF might be up-regulated by c-Fos and that the abundant levels of BDNF in the surrounding normal brain might trigger an autocrine loop promoting glioma cell survival. In addition, BDNF secreted by glioma cells might stimulate angiogenesis by acting in a paracrine way on endothelial cells. Therefore, in the brain the anti-JAM-C antibody would block important signals conferring survival and angiogenic properties to glioma cells.

Overall the mechanisms through which JAM-C might exert crucial activities in the context of a developing glioma are schematised in FIG. 23. JAM-C, on the membrane of glioma cells might be a fundamental molecule at the interface between the surrounding brain environment and the complex networks of intracellular signals regulating key processes for cancer development. Its potential involvement in diverse adhesive contacts with other members of its own family, for instance JAM-B, with integrins bound to brain ECM ligands and RTKs critical for the stimulation of glioma growth, would make of JAM-C a central molecule in providing glioma cells a range of advantages for their expansion in the brain. A crucial partner in mediating the transmission of these multiple gains from JAM-C to the glioma cell would be c-Src. Activation of c-Src by JAM-C would have a strong impact on the aggressiveness of the glioma cell by virtue of its pleiotropic effects on the intracellular signals implicated in cancerogenesis, and in particular in those crucial for gliomagenesis. In this context, the anti-JAM-C antibody would perturb the important communications mediated by JAM-C between the glioma cell and its natural surroundings and would have dramatic effects on the development of a glioma in the brain.

Conclusions and Perspectives

The work described provides evidences that the adhesion molecules JAM-C and JAM-B are aberrantly overexpressed in human gliomas and that this up-regulation is relevant to glioma malignancy into its natural environment: the brain. An anti-JAM-C antibody strongly inhibited the growth and invasion of a mouse model of human glioma grown in the brain while it was less effective on the growth of the tumour in the subcutis. Indeed, by gene expression analysis of mouse glioma cells differentially expressing JAM-C we have demonstrated that high levels of the protein on the surface of glioma cells are correlated with an up-regulation of genes that are components of the major genetic pathways activated by human gliomas: the MAPK-ERK and Rho family small GTPases pathways. This is achieved by glioma cells through JAM-C mediated increases of the levels and activation of the c-Src non receptor tyrosine kinase, a master up-stream regulator of several cellular pathways and processes abnormally stimulated in human gliomas. The activation of c-Src is likely to be the result of multiple adhesive interactions between JAM-C and other adhesion molecules, as we have experimentally shown for JAM-B.

Materials and Methods

Cell Culture and Antibodies

Human glioma cell lines were established from glioma biopsies by digestion with 0.1% collagenase (Roche Diagnostics Ltd, Rotkreuz, Switzerland) and 0.01% DNAse (Roche Diagnostics Ltd, Rotkreuz, Switzerland) at 37° C. GL261 mouse glioma cells were a generous gift of Geza Safrany. Both human and mouse glioma cells were cultured in DMEM containing 4.5 g/l glucose, 10% FCS and antibiotics (all from Invitrogen). All anti-human and anti-mouse JAM-C and JAM-B rabbit polyclonal antibodies were obtained by immunizing rabbits with the recombinant soluble JAM-C or JAM-B proteins containing the $V_H$-$C_2$ domains. The antibodies were produced by Covalab, Lyon, France. Rat monoclonal antibodies H36 and D33 directed against mouse JAM-C also cross-reacted with human JAM-C and were previously described (Aurrand-Lions et al., 2001a; Aurrand-Lions et al., 2001b; Johnson-Leger et al., 2002b). Rat $IgG_{2a}$ anti-human CD44 (Hermes, 9B5) monoclonal antibody used as isotype control was previously described (Lamagna et al., 2005a). Rat monoclonal antibody against mouse PECAM-1 (GC51) was previously described (ibid.) and the Rat $IgG_{2b}$ isotype control antibody was purchased from BD Pharmingen, San Diego, Calif. Rat monoclonal antibody J3 against mouse JAM-B was obtained by immunization of rat with a recombinant JAM-B molecule containing the $V_H$-$C_2$ domains. Goat anti-rat PE coupled antibody used for FACS analysis was purchased from Southern Biotechnology (Birmingham, USA). Donkey anti-rabbit coupled to HRP used for immunohistochemistry for mouse JAM-C was purchased from Jackson Immunoresearch Laboratories, Inc., West Grove, Pa., USA. Recombinant Mouse JAM-B/Fc Chimera antibody was purchased from R&D, MN, USA.

RT-PCR

Total RNA from cells was extracted using the RNeasy kit (Qiagen). cDNA was obtained from 0.5-1 µg of total RNA employing oligo(dT) and Superscript II reverse transcriptase (Invitrogen). RT-PCR for human JAM-C was performed using primers 5' CTG GGG MG ACA TCC CTG MG 3' (Forward) and 5'AGTGCGGATGTAGTTAACTCC 3' (Reverse). 3 min. of initial denaturation were followed by 35 cycles at 94° C. for 45 sec., 58° C. for 45 sec. and 72° C. for 1 min. A final extension of 10 min. was performed at 72° C. RT-PCR for human α-actin was performed with primers: 5' TGA CGG GGT CAC CCA CAC TGT GCC CAT CTA 3' (Forward) and 5' CTA GM GCA TTT GCG GTG GAC GAT GGA GGG 3'(Reverse). After 1 min. of initial denaturation, 30 cycles were performed at 94° C. for 30 sec., 58° C. for 30 sec., and 72° C. for 30 sec. followed by a final extension at 72° C. for 2 min. RT-PCR for human JAM-B was performed as for JAM-C with primers: 5' AGT AGT CAC ARC AGT AGA GTA C 3' (Forward) and 5' ACT TAT GTT GAG ATC ATC TAC TTG 3' (Reverse).

Flow Cytometry

For analysis of human JAM-C expression Ge258 human glioblastoma were incubated on ice with 5 µg/ml of anti-JAM-C monoclonal antibody H36 or isotype-matched control antibody. After washing with PBS, 0.2% FCS and 0.01% azide, cells were incubated with a goat anti-rat FITC coupled antibody (Jackson Immunoresearch Laboratories, Inc., West Grove, PA, USA).

For analysis of human JAM-B expression Ge258 human glioblastoma were incubated on ice with 5 µg/ml of Goat anti-JAM-B antibody (RD Systems, Minneapolis, Minn., USA) or isotype-mached control antibody. After washing with PBS, 0.2% FCS and 0.01% azide, cells were incubated with a mouse anti-goat FITC coupled antibody (Jackson Immunoresearch Laboratories, Inc., West Grove, Pa., USA).

For analysis of mouse JAM-C expression GL261, GL261-233, GL261-233RC and GL261-233R mouse glioma cells were incubated on ice with 5 µg/ml of rat monoclonal anti-JAM-C H36 antibody or isotype-mached control antibody (BD Pharmingen, San Diego, Calif.). After washing with PBS, 0.2% FCS and 0.01% azide, cells were incubated with a goat anti-rat PE conjugated antibody (Southern Biotechnology, Birmingham, Ala., USA).

For analysis of mouse JAM-B expression, GL261 cells were incubated on ice with 5 µg/ml of J3 rat monoclonal anti-JAM-B antibody or isotype-mached control antibody (BD Pharmingen, San Diego, Calif.). After washing with PBS, 0.2% FCS and 0.01% azide, cells were incubated with a goat anti-rat FITC conjugated antibody (Jackson Immunoresearch Laboratories, Inc., West Grove, Pa., USA).

For analysis of soluble chimeric JAM-B/Fc binding to the surface of GL261-233RC and GL261-233R cells, cells were incubated 25 min on ice with a mix of chimeric JAM-B/Fc antibody at 20 µg/ml and Goat anti-Human PE conjugated antibody (Jackson Immunoresearch Laboratories, Inc., West Grove, Pa., USA) at 20 µg/ml final concentration. Cells were then washed with PBS, 0.2% FCS and 0.01% azide and analysed.

All analyses were performed using a FACScan (Becton Dickinson, Palo Alto, Calif.).

Immunoprecipitation and Western Blotting

Immunoprecipitations of mouse and human JAM-C were performed with polyclonal rabbit anti-JAM-C 501 and 720 respectively, using 50 mM Tris-HCl buffer, pH 7.4, 150 mM NaCl, 0.5% NP40, protease inhibitor mixture (Roche Diagnostics Ltd, Rotkreuz, Switzerland) for lysis. After SDS-PAGE and nitrocellulose membrane transfer of the immunoprecipitates, the biotinylated proteins were revealed with peroxidase coupled streptavidin (Jackson Immunoresearch, Inc., West Grove, Pa., USA) and ECL (Amersham Pharmacia Biotech).

For Western Blotting with polyclonal anti-human JAM-B/VE-JAM antibody (R&D Systems, MN, USA) cells were lysed with 50 mM Tris, 50 NaCl, 0.5% Nonidet P40 containing protease inhibitors cocktail (Roche Diagnostics Ltd, Rotkreuz, Switzerland). Protein concentrations were determined using the BCA kit (Biorad). Then, 50 µg of proteins were subjected to SDS-PAGE and transferred onto a Protan nitrocellulose filter (Whatman Schleicher&Schuell plc, Middlesex, TW8 9BW, UK). The membrane was then blocked with 5% non fat dry milk and incubated overnight at 4° C. with goat-anti-human JAM-B/VE-JAM antibody (R&D Systems, MN, USA) at 1/1000 dilution. After washes with PBS-Tween 0.1% incubation for 1 hour at room temperature with donkey anti-goat HRP-conjugated secondary antibody (Jackson Immunoresearch, Inc., West Grove, Pa., USA) at 1/10000 dilution was performed. After washes detection was performed using chemiluminescent ECL™ Western Blotting Analysis System (Amersham Biosciences, General Electric Company, CT, USA).

Immunohistochemistry

For immunohistochemistry on human brain tumours with polyclonal anti-human JAM-C antibody 720, cryosections were fixed with acetone/methanol (1:1) for 5 minutes at −20° C., then dried 20-30 minutes. Sections were hydrated in PBS 1x then incubated 10 minutes in PBS/0.3% $H_2O_2$ to inhibit endogenous peroxidase activity, and blocked in PBS1x/BSA3%, Tween 0.5%, 10% Human Serum, 10% Normal Goat Serum for 15 minutes at room temperature. After 1 hour and 30 min. incubation with the primary antibody at 1/250 dilution, the sections were washed and Rabbit EnVision+ system-HRP was added (Dako, Denmark) for 30 minutes. After wash with PBS followed by Sodium Acetate 0.1 M pH 4.8, the staining was revealed with AEC (3-Amino-9-ethyl-carbazole, BioGenex, Ca, USA) and counterstained with hematoxylin.

For immunohistochemistry on human brain tumours with polyclonal anti-human JAM-B/VE-JAM antibody (R&D Systems, MN, USA), cryosections were dried for no more than 20 minutes, then fixed 15 min at room temperature in 4% formaldehyde solution (Merck). They were washed in Tris-Tween buffer (Dako, Denmark), then incubated 5 min. in Peroxidase Blocking Reagent (Dako, Denmark) and washed for 15 min. An incubation of 30 min in 10% human serum, 10% Normal Rabbit Serum (Dako, Denmark) was performed before adding the primary antibody for 1 h at a final concentration of 0.3 µg/ml. After washing, the sections were incubated with a Rabbit anti-Goat biotin (Dako, Denmark) for 30 min and then with a streptavidin and biotinyled peroxidase complex (Dako, Denmark). Staining was revealed with 3,3-diaminobenzidine (DAB+, Dako, Denmark) for approximately 2 min and counterstained with hemalun.

For immunohistochemistry of mouse JAM-C, cryosections were dried maximum 20 minutes, fixed in acetone/methanol (1:3) for 5 minutes at −20° C., washed in Tris-Tween Buffer (Dako, Denmark), incubated in Peroxidase Block Reagent (Dako, Denmark), and then washed 15 minutes. Rabbit polyclonal anti-JAM-C antibody 501 or rabbit pre-immune serum (negative control) were then added at a dilution of 1/250, and incubated for 1 hour at room temperature. After washes a horseradish peroxidase coupled donkey anti-rabbit antibody (Jackson Immunoresearch Laboratories, Inc., West Grove, Pa., USA.) was added and the staining revealed by DAB+ (Dako, Denmark).

For immunohistochemistry of mouse JAM-B, cryosections were dried for 20 min maximum, fixed in acetone, washed in Tris-Tween buffer (Dako, Denmark), incubated in Peroxidase Blocking Reagent (Dako, Denmark) and washed for 15 min. Rabbit anti-mouse JAM-B 829 or the corresponding rabbit pre-immune serum (negative control) were then added at a dilution of 1/300 and incubated for 1 hour at room temperature. After washes a horseradish peroxidase coupled donkey anti-rabbit antibody (Jackson Immunoresearch Laboratory, Inc., West Grove, Pa., USA) was added and the staining revealed by 3,3-diaminobenzidine (Dako, Denmark).

Immunohistochemistry for quantification of vessel density in both mouse sub-cutaneous and intra-cerebral tumors, was performed with a monoclonal anti-PECAM-1 (GC51) antibody. Cryosections were dried maximum 20 minutes, fixed in aceton for 5 minutes at −20° C., hydrated in TBS1x (Tris Buffered Saline) and incubated in Peroxidase Block Reagent (Dako, Denmark). Then incubation with Normal Goat Serum (Dako, Denmark) for 15 minutes was performed prior to incubation with anti-PECAM-1 antibody for 1 hour at room temperature at a final concentration of 0.5 µg/ml. After wash, a goat anti-rat horseradish peroxidase coupled antibody (Invitrogen, CA, USA) was added for 30 minutes at room temperature and the staining was revealed with DAB+ (Dako, Denmark).

Tumour Grafts

C57BL/6 mice were from Elevage Janvier (Le Genest St Isle, France). For sucutaneous implantations, 106 tumour cells in PBS were injected on the right flanks in 6-12 weeks old female mice. Mice were treated with intra-peritoneal injections performed every second day with either PBS or PBS containing 150 µg or 200 µg of antibodies (D33 and 9B5), for subcutaneously or intracerebrally implanted mice respectively. Subcutaneous tumour volumes were measured using a caliper and calculated as (length×width$^2$)/2. Implantations in the brain were performed on 11 weeks old female mice with a stereotaxic apparatus as previously described (Walker et al., 2000), using 2×10$^4$ cells in 2 µl of methylcellulose injected at 1 µl/min with equally slow withdrawal of the needle after injection. Intra-cerebral tumour volumes were calculated on serial MRI images. All animal procedures were approved by the Institutional Ethical Committee and the Cantonal Veterinary Office.

Magnetic Resonance Imaging

MRI was performed using a clinical 1.5 T (Philips Intera) unit. The mice were placed in general anaesthesia (0.9% NaCl containing 50% Ketalar and 8% Rompun) in a specially-developed small animal holder (reference). Using a dedicated surface coil, T1-and T2-weighted images in the coronal plane were acquired at first, followed by T1-weighted coronal images with application of Gd-DTPA (administered by i.p. injections of 5 µl/g of mouse weight). The images were exported to an external workstation for post-processing.

Quantification of Vessel Density, Tumour Area and Tumour Shape

For subcutaneous tumours pictures four entire cryosections stained with PECAM-1 antibody were acquired with a Zeiss Axiophot 1 microscope equipped with an Axiocam colour CCD camera, and the recorded images treated on a PentiumIII computer through the AxioVision software.

For intra-cerebrally grown tumours pictures of 7-8 entire brain cryosections stained with PECAM-1 antibody were acquired with a Nikon Scan microscope with automatic scanning of the samples and stitching of the resulting images.

The images were processed in MetaMorph Image Analysis software (Molecular Devices, Union City, Calif., USA). The quantification image processing algorithm applied to those images is composed of several steps described below.

Figure 24:
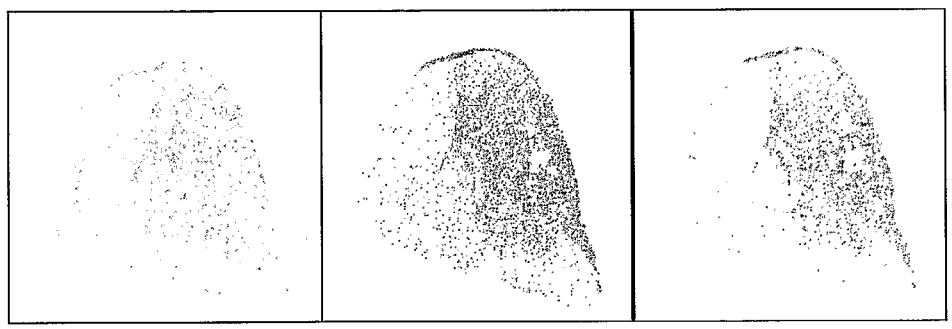
FIG. 24: Quantification image processing of colour CCD images step 1: The image was colour thresholded in the HSI colour space (defined by pixel hue, saturation, and intensity). Thresholding intervals were selected as follows: from 159 to 217 for hue, from 10 to 255 for saturation and from 109 to 255 for intensity. The thresholded area is shown the middle image. The thresholded area elements were filtered with respect to size. Only elements having certain size were retained as shown in the right image.

First, to isolate the tumoral area, the image was colour thresholded in the HSI colour space (defined by pixel hue, saturation, and intensity). Thresholding intervals were selected as follows: from 159 to 217 for hue, from 10 to 255 for saturation and from 109 to 255 for intensity. The thresholded area is shown in FIG. 24 (middle image).

The same thresholding values were used for all images thus providing statistical reference for comparison. The next step of the processing filtered the thresholded area elements with respect to size. Only elements having certain size were retained as shown in FIG. 24 (right image).

Figure 25:
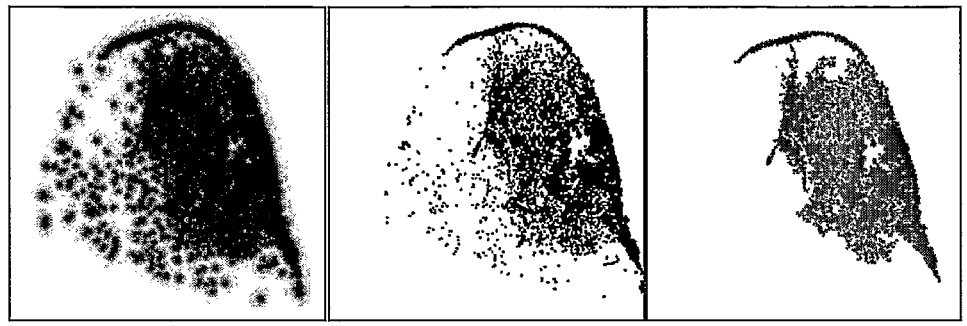
FIG. 25: Quantification image processing of colour CCD images step 2: Definition of the one area of the tumour. The retained individual elements were used to build the distance map shown in the left image. In this map, the colour of pixels represents the distance to the closest tumoral element. This map was used to delimit the area lying in a close neighbourhood of the tumoral elements as shown on the middle part of the figure. The latter was processed to retain only the largest and most representative part of the tumor. This part for the current image is shown on the right. The area of this part was the value corresponding to the total tumour area used for statistical analysis of intra-cerebral tumour areas and shown in FIG. 17.
Figure 26:
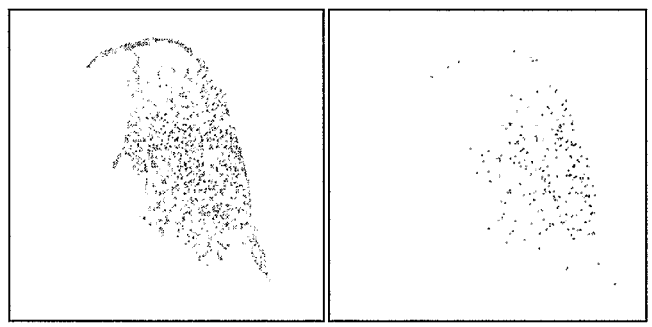
FIG. 26: Quantification image processing of colour CCD images step 3: The obtained total tumour area was analysed for the percentage of surface represented by vessels. The blood vessels were isolated with colour thresholded in the HSI colour space. Thresholding intervals were selected as follows: from 0 to 79 for hue, from 10 to 137 for saturation and from 0 to 242 for intensity. The thresholded area is shown in magenta in the left image. The selected vessels are shown separately on the right part of the figure. The total area of vessels was used for statistical analysis of the percentage of PECAM-1 stained surface relative to the total area of the tumour.

The next processing step was the definition of the one area of the tumour. The retained individual elements were used to build the distance map shown in FIG. 25 (left image). In this map, the colour of pixels represents the distance to the closest tumoral element. This map was used to delimit the area lying in a close neighbourhood of the tumoral elements as shown on the middle part of the figure. The latter was processed to retain only the largest and most representative part of the tumor. This part for the current image is shown on the right. The area of this part was the value corresponding to the total tumour area used for statistical analysis of intra-cerebral tumour areas and shown in FIG. 17. The obtained total tumour area was then analysed for the percentage of surface represented by vessels. The blood vessels were isolated with colour thresholded in the HSI colour space. Thresholding intervals were selected as follows: from 0 to 79 for hue, from 10 to 137 for saturation and from 0 to 242 for intensity. The thresholded area is shown in magenta in FIG. 26 (left image). The selected vessels are shown separately on the right part of the figure.

Figure 27:
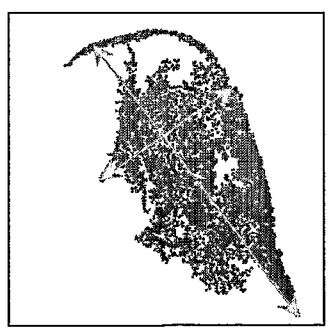
FIG. 27: Quantification image processing of colour CCD images step 4: Two values were used to characterise the form of the tumour: the length and the breadth. The length is defined as the span of the longest chord through the outline of the tumour. In other words the length is the distance between the two most remote points belonging to the tumour. In the figure the parameter is measured as the length of the orange line. The breadth is the calliper width of the tumour outline perpendicular to the longest chord. In the figure this parameter corresponds to the cyan line and represents the largest width of the tumour measured along the orange line. Both, length and breadth were measured for each tumoral area and the ratio length/breadth was used to define the shape of the tumour.

The total area of vessels was used for statistical analysis of the percentage of PECAM-1 stained surface relative to the total area of the tumour. Two values were used to characterise the form of the tumour: the length and the breadth. The length is defined as the span of the longest chord through the outline of the tumour. In other words the length is the distance between the two most remote points belonging to the tumour. In FIG. 27 above the parameter is measured as the length of the orange line. The breadth is the calliper width of the tumour outline perpendicular to the longest chord. In FIG. 27 this parameter corresponds to the cyan line and represents the largest width of the tumour measured along the orange line. Both, length and breadth were measured for each tumoral area and the ratio length/breadth was used to define the shape of the tumour.

Construction of RNAi Vectors and Transfections

The pSuper gfp/neo vector was purchased from Oligoengine Inc, Seattle, USA. To construct the pSuper.gfp/neo-233 vector, a pair of oligonucleotides was designed containing the 19-nt RNAi target sequence derived from the mouse JAM-C mRNA transcript starting at position +233. The forward oligonucleotide included a BglII restriction site at the 5' end, the 19-nt RNAi target sequence in both sense and anti-sense orientation (bold letters) separated by a 9-nt spacer sequence designed to generate a hairpin, and 5 thymidines in a row as termination signal at the 3' end. The reverse oligonucleotide included a HindIII restriction site at the 5' end. Forward oligonucleotide: 5' GAT CCC CGC CAA ACC ACA TAT GTG TAT TCA AGA GAT ACA CAT ATG TGG TTT GGC TTT TTA 3'. Reverse oligonucleotide: 5' AGC TTA AAA AGC CAA ACC ACA TAT GTG TAT CTC TTG MT ACA CAT ATG TGG TTT GGC GGG 3'. The two oligonucleotides were then annealed and cloned into the pSuper gfp/neo vector following the Oligoengine instruction manual. Transfections of GL261 cells were performed with Fugene 6 (Roche Diagnostics Ltd, Rotkreuz, Switzerland). Stable transfectants were selected with 100 µg/ml G418 (Invitrogen, CA, USA). The expression vector used to rescue GL261-233 cells for JAM-C expression, was obtained by PCR introduction of two conservative point mutations into the mouse JAM-C cDNA. Two primers, 5' CAA GTG ACC CTA GGA TTG MT GGA AGA AAA TCC MG ATG GCC AAA CM CGT ATG TGT 3' (Forward) and 5' CCT CAC TCG TCC GGA TGT AGT TAA CAC CGT 3' (Reverse), were used to generate a C to A and an A to G substitutions at positions +240 and +243, respectively, of the mouse JAM-C mRNA. The 686 bp PCR fragment obtained with these primers and digested with AvrII and HpaI endonucleases was used to replace the corresponding wild-type fragment in the mouse JAM-C cDNA cloned into the pcDNA3.1/Neo vector. The new mutant JAM-C cDNA thus obtained was then cloned into the pcDNA3.1/Hygro vector. Both pcDNA3.1/Hygro empty vector (Invitrogen, CA, USA) and pcDNA3.1/Hygro-JAM-C Rescue vector were linearized with FspI endonuclease and transfected into GL261-233 cells with Lipofectamine 2000 (Invitrogen, CA, USA). Stably transfected cells were selected with 200 µg/ml hygromycin (Brunschwig, Basel, Switzerland). By this way two cell lines were obtained GL261-233RC (Rescue control) and GL261-233R (Rescue).

Affymetrix Gene Expression Analysis.

For gene expression analysis GL261-233RC and GL261-233R cells were plated in normal culture medium and 48 hours later, when they reached about 95% of confluency, they were used for total RNA extraction. Total RNA was extracted using the RNeasy kit (Quiagen) and subjected to DNAse treatment according to the manufacturer's protocol. Affymetrix analysis was performed at the Genomic Platform "Frontiers in Genetics" at the University Medical Centre (CMU) Geneva following the procedures described below.

Total RNA (5 μg) from each sample (3 independent samples per cell line were analysed) was reverse-transcribed at 42° C. for 1 h by using 100 pmol of an oligo(dT)$_{24}$ primer containing a 5' T7 RNA polymerase promoter sequence [5'-GGCCAGTGAATTGTAATACGACTCAC-TATAGGGAGGCGG(dT)$_{24}$-3'], 50 mM Tris.HCl (pH 8.3), 75 mM KCl, 3 mM MgCl$_2$, 10 mM DTT, 0.5 mM dNTPs, and 200 units of SuperScript II reverse transcriptase (Invitrogen). The second strand of cDNA was then synthesized by using 40 units of *Escherichia coli* DNA polymerase I, 10 units of *Escherichia coli* DNA ligase, and 2 units of RNase H in a reaction containing 25 mM Tris.HCl (pH 7.5), 100 mM KCl, 5 mM MgCl$_2$, 10 mM (NH$_4$)$_2$SO$_4$, 0.15 mM NAD$^+$, 1 mM dNTPs, and 1.2 mM DTT. The synthesis was carried out at 16° C. for 2 h and was stopped by using EDTA. Then, double-stranded cDNA products were purified by phenol/chloroform extraction and ethanol precipitation. Double-stranded cDNA products were then used for in vitro transcription of Biotinylated complementary RNAs (cRNAs) by T7 RNA Polymerase (ENZO BioArray High Yield RNA transcript-labeling kit, Enzo Biochem). cRNAs were purified by using affinity resin (Qiagen RNeasy spin columns) and randomly fragmented by incubating at 94° C. for 35 min in a buffer containing 40 mM Tris.acetate (pH 8.1), 100 mM potassium acetate, and 30 mM magnesium acetate to produce molecules of 35-200 bases. The labeled cRNA samples were mixed with 0.1 mg·ml$^{-1}$ sonicated herring sperm DNA in a hybridization buffer containing 100 mM 2-N-morpholinoethanesulfonic acid (Mes), 1 M NaCl, 20 mM EDTA, and 0.01% Tween 20, denatured at 99° C. for 5 min, and equilibrated at 45° C. for 5 min before hybridization. The hybridization mix was then transferred to the mouse GeneChip microarray cartridge (430 2.0 Array) and hybridized at 45° C. for 16 h on a rotisserie at 60 rpm. The hybridized arrays were then rinsed and stained in a fluidics station (Affymetrix). The arrays were first rinsed with wash buffer A [6×SSPE (0.9 M NaC/0.06 M NaH$_2$PO$_4$/0.006 M EDTA)/0.01% Tween 20/0.005% antifoam] at 25° C. for 10 min, incubated with wash buffer B (100 mM Mes/0.1 M NaCl/0.01% Tween 20) at 50° C. for 20 min, stained with streptavidin-phycoerythrin (SAPE) (100 mM Mes/1 M NaCl/0.05% Tween 20 containing 10 mg/ml SAPE and 2 mg/ml BSA) at 25° C. for 10 min, washed with wash buffer A at 25° C. for 20 min, and stained with biotinylated anti-streptavidin antibody at 25° C. for 10 min. After staining, arrays were stained with SAPE at 25° C. for 10 min and washed with wash buffer A at 30° C. for 30 min. The probe arrays were scanned twice, and the intensities were averaged with a GeneArray Scanner (Agilent Technologies, Palo Alto, Calif.) by using MAS 5.0 (Affymetrix).

Data Processing and Normalization (GeneChip).

The expression level for each gene was calculated with the following procedure. First, the local background and global background were determined. The array was divided into 16 sectors and local background was estimated from the average of the lowest 2% of probe values in the sector. The global background was estimated by the average of the lowest 5% of the probe-set value. Second, intensity values of probes in a probe set were condensed into a single value to represent the expression value. Within a probe set, probes with negative or zero values as outliers were removed, and the signal intensities of the rest of the probes were averaged to represent the expression level. Third, absolute calls were assigned based on the difference between the expression value of a probe set and the local noise and global background levels. The local noise level was determined as the standard deviation of all pixels in the probe sets. Probe sets with a signal value above the global background plus twice the local noise were called "present"; probe sets with a value less than global background were called "absent"; and probe sets with values greater than global background but less than global background plus twice the local noise were called "marginal." Data from all samples were normalized by scaling the average intensity of the probe sets to a target of 80. Further data-filtering and analysis used GENESPRING software (Agilent).

Analysis of Affymetrix Microarray Data.

The data obtained by Affymetrix analysis were analysed using the Ingenuity Systems software.

Real Time PCR

Single-stranded cDNA templates for real-time RT-PCR analysis were synthesized from the same RNA pools used for the microarray analysis, and from independently derived and extracted secondary samples as described above. cDNA synthesis was carried out by using SuperScript II Reverse Transcriptase (Invitrogen Life Technologies). The sequences of the primers used for Real Time PCR amplifications were the following: for mouse JAM-C: 5' GAA CTC GGA GAC AGG CAC TC 3' (Forward) and 5' TAC TGC CCA GAG TCG TCC TT 3' (Reverse); for mouse c-Fos: 5'GAA TGG TGA AGA CCG TGT CA 3' (Forward) and 5' TCT TCC TCT TCA GGA GAT AGC TG 3' (Reverse); for mouse FosL2: 5'ACG CCG AGT CCT ACT CCA G 3' (Forward) and 5' CAG GCA TAT CTA CCC GGA AC 3' (Reverse); for mouse PAK3: 5' CCA AAT GGG AAC TAC TTG AAC AG 3' (Forward) and 5' CCA AAT GGG AAC TAC TTG AAC AG 3' (Reverse); for mouse PVR: 5' ACG GTG GAG CAT GM AGC 3' (Forward) and 5' GGA CAC GTT TTC AGG TGG AT 3' (Reverse); for mouse BDNF: 5' AGT CTC CAG GAC AGC AAA GC 3' (Forward) and 5' AAG GAT GGT CAT CAC TCT TCT CA 3' (Reverse); for mouse RAPGEF2: 5' TTT CCT TGT GCG TTG CTA TG 3' (Forward) and 5' TGT GM GTC TGC AGG GAG TTT 3' (Reverse); for mouse Tspan6: 5' GGT TGT TTC GCT ACC TGT CG 3' (Forward) and 5' GTG TCA GM ACA TCG CGT ACA 3' (Reverse); for mouse AFAP: 5' GCC ATC GM GTG AAT GCA G 3' (Forward) and 5' CAG CCT CTT CAA CTT GTC CTC 3' (Reverse); for mouse Ptgfrn: 5' TCA MT TGT TCT GTA TCG TCA CTG 3' (Forward) and 5' ACA TCG AAG GCC ATG TCA TC 3' (Reverse); for mouse VLDLR: 5' GGG CCA TCC TTC CTC TCT T 3' (Forward) and 5' GCC MT TCC TCC ACA TCA AG 3' (Reverse); for mouse Tubulin 2: 5' GCA GTG CGG CM CCA GAT 3' (Forward) and 5' AGT GGG ATC MT GCC ATG CT 3' (Reverse); for mouse GAPDH: 5' TCCATGACAACTTTGGCATTG 3' (Forward) and 5' CAG TCT TCT GGG TGG CAG TGA 3' (Reverse).

Taqman assays were performed using the Universal Probe Library (Exiqon, commercialized by Roche Diagnostics) (Mouritzen et al, BioTechniques, p 92, September-October 2004). Amplicons were designed using the web based software provided by Roche (www.roche-applied-science.com) with default parameters in every case.

Assays were tested in standard +/−RT reactions of RNA samples for genomic contamination; in the majority of cases, no amplification was observed, and in the remainder, amplification was at least 10 cycles later in −RT compared with +RT reactions. Amplicon sequences where checked by BLAST against the mouse genome to ensure that they were specific for the gene being assayed. The efficiency of each Taqman assay was tested in a cDNA dilution series (Livak and Schmittgen 2001). All reactions used FastStart TaqMan Probe Master (ROX), complemented with ROX to 300 nM.

All PCRs were run in an ABI 7900 Sequence Detection System (Applied Biosystems) with the following conditions: 50° C. for 2 min, 95° C. for 10 min, and 40 cycles of 95° C. 15 sec/60° C. for 1 min.

Immunofluorescence

For immunofluorescence of mouse JAM-C, cells were washed with PBS and fixed with 4% paraformaldehyde for 15 min at room temperature. Cells were then washed in PBS, 0.2% FCS and 0.01% azide and incubated for 1 hour with polyclonal anti-mouse JAM-C ("526"). After 2 washes, cells were then incubated with an anti-rabbit coupled with Texas Red (Jackson Immunoresearch Laboratory, Inc., West Grove, Pa., USA). In the third wash, DAPI was added for 5 min and the slide was mounted with Mowiol (Calbiochem by EMD Biosciences).

Analysis of c-SRC Protein Levels and Activation

Amounts of total c-Src protein and of active phosphorylated-c-Src were quantified using FACE c-Src ELISA kit (Active Motif, CA, USA). GL261-233RC and GL261-233R cell lines were seeded at day 1 at 20'000 cells/well in a 96 flat well plate in normal medium. At day 2, cells were incubated 30 min on ice and then 20 min at 37° C. with recombinant mouse JAM-B/Fc chimera antibody (R&D, MN, USA) at a final concentration of 5 µg/ml. Cells were then fixed and analysed with c-Src ELISA following the manufacturer's instructions (colorimetric Assay for adherent cells).

Statistical Analysis

All data were analysed for statistical significance using SigmaStat software.

Deposit Information

The hybridoma cell line CRAM-17D33 that produces the rat monoclonal antibody D33 has been accepted as a patent deposit in accordance with the Budapest Treaty of 1977 on 27 Sep. 2006 by the European Collection of Cell Cultures (ECACC) under accession no. 06092701

REFERENCES

The following references, to the extent that they provide exemplary procedural or other details supplementary to those set forth herein, are specifically incorporated herein by reference:

1. Aligayer, H., Boyd, D. D., Heiss, M. M., Abdalla, E. K., Curley, S. A., and Gallick, G. E. (2002). Activation of Src kinase in primary colorectal carcinoma: an indicator of poor clinical prognosis. Cancer 94, 344-351.
2. Arrate, M. P., Rodriguez, J. M., Tran, T. M., Brock, T. A., and Cunningham, S. A. (2001). Cloning of human junctional adhesion molecule 3 (JAM3) and its identification as the JAM2 counter-receptor. J Biol Chem 276, 45826-45832.
3. Aurrand-Lions, M., Duncan, L., Ballestrem, C., and Imhof, B. A. (2001a). JAM-2, a novel immunoglobulin superfamily molecule, expressed by endothelial and lymphatic cells. J Biol Chem 276, 2733-2741.
4. Aurrand-Lions, M., Johnson-Leger, C., Wong, C., Du, P. L., and Imhof, B. A. (2001b). Heterogeneity of endothelial junctions is reflected by differential expression and specific subcellular localization of the three JAM family members. Blood 98, 3699-3707.
5. Ausman, J. I., Shapiro, W. R., and Rall, D. P. (1970). Studies on the chemotherapy of experimental brain tumors: development of an experimental model. Cancer Res 30, 2394-2400.
6. Bendell, J. C., Domchek, S. M., Burstein, H. J., Harris, L., Younger, J., Kuter, I., Bunnell, C., Rue, M., Gelman, R., and Winer, E. (2003). Central nervous system metastases in women who receive trastuzumab-based therapy for metastatic breast carcinoma. Cancer 97, 2972-2977.
7. Binz, H. K., Amstutz, P., Kohl, A., Stumpp, M. T., Briand, C., Forrer, P., Grutter, M. G., and Pluckthun, A. (2004). High-affinity binders selected from designed ankyrin repeat protein libraries. Nat Biotechnol. 22, 575-582.
8. Bitonti, A. J. and Dumont, J. A. (2006). Pulmonary administration of therapeutic proteins using an immunoglobulin transport pathway. Adv. Drug Deliv. Rev 58, 1106-1118.
9. Bitonti, A. J., Dumont, J. A., Low, S. C., Peters, R. T., Kropp, K. E., Palombella, V. J., Stattel, J. M., Lu, Y., Tan, C. A., Song, J. J., Garcia, A. M., Simister, N. E., Spiekermann, G. M., Lencer, W. I., and Blumberg, R. S. (2004). Pulmonary delivery of an erythropoietin Fc fusion protein in non-human primates through an immunoglobulin transport pathway. Proc Natl Acad Sci USA 101, 9763-9768.
10. Chavakis, T., Keiper, T., Matz-Westphal, R., Hersemeyer, K., Sachs, U. J., Nawroth, P. P., Preissner, K. T., and Santoso, S. (2004). The junctional adhesion molecule-C promotes neutrophil transendothelial migration in vitro and in vivo. J Biol Chem 279, 55602-55608.
11. Dall'Acqua, W. F., Damschroder, M. M., Zhang, J., Woods, R. M., Widjaja, L., Yu, J., and Wu, H. (2005). Antibody humanization by framework shuffling. Methods 36, 43-60.
12. Dall'Acqua, W. F., Woods, R. M., Ward, E. S., Palaszynski, S. R., Patel, N. K., Brewah, Y. A., Wu, H., Kiener, P. A., and Langermann, S. (2002). Increasing the affinity of a human IgG1 for the neonatal Fc receptor: biological consequences. J Immunol 169, 5171-5180.
13. Damschroder, M. M., Widjaja, L., Gill, P. S., Krasnoperov, V., Jiang, W., Dall'Acqua, W. F., and Wu, H. (2007). Framework shuffling of antibodies to reduce immunogenicity and manipulate functional and biophysical properties. Mol Immunol 44, 3049-3060.
14. Datta-Mannan, A., Witcher, D. R., Tang, Y., Watkins, J., Jiang, W., and Wroblewski, V. J. (2007a). Humanized IgG1 variants with differential binding properties to the neonatal Fc receptor: relationship to pharmacokinetics in mice and primates. Drug Metab Dispos. 35, 86-94.
15. Datta-Mannan, A., Witcher, D. R., Tang, Y., Watkins, J., and Wroblewski, V. J. (2007b). Monoclonal antibody clearance. Impact of modulating the interaction of IgG with the neonatal Fc receptor. J Biol Chem 282, 1709-1717.
16. Dufner, P., Jermutus, L., and Minter, R. R. (2006). Harnessing phage and ribosome display for antibody optimisation. Trends Biotechnol. 24, 523-529.
17. Dumont, J. A., Bitonti, A. J., Clark, D., Evans, S., Pickford, M., and Newman, S. P. (2005). Delivery of an erythropoietin-Fc fusion protein by inhalation in humans through an immunoglobulin transport pathway. J Aerosol Med 18, 294-303.
18. Edelman, G. M., Cunningham, B. A., Gall, W. E., Gottlieb, P. D., Rutishauser, U., and Waxdal, M. J. (1969). The covalent structure of an entire gammaG immunoglobulin molecule. Proc Natl Acad Sci USA 63, 78-85.
19. Gerber, D. E. and Laterra, J. (2007). Emerging monoclonal antibody therapies for malignant gliomas. Expert. Opin Investig. Drugs 16, 477-494.
20. Ghetie, V., Popov, S., Borvak, J., Radu, C., Matesoi, D., Medesan, C., Ober, R. J., and Ward, E. S. (1997). Increasing the serum persistence of an IgG fragment by random mutagenesis. Nat Biotechnol. 15, 637-640.
21. Gill, D. S. and Damle, N. K. (2006). Biopharmaceutical drug discovery using novel protein scaffolds. Curr Opin Biotechnol. 17, 653-658.

22. Gonzales, N. R., Padlan, E. A., De Pascalis, R., Schuck, P., Schlom, J., and Kashmiri, S. V. (2004). SDR grafting of a murine antibody using multiple human germline templates to minimize its immunogenicity. Mol Immunol 41, 863-872.
23. Grasso, L., Shaohong, L., Nicolaides, N. E., and Sass, P. M. Methods of generating high-production of antibodies from hybridomas created by in vitro immunization. Morphotek, Inc. WO 2004/046330. 3-6-2004.
24. Green, L. L. (1999). Antibody engineering via genetic engineering of the mouse: XenoMouse strains are a vehicle for the facile generation of therapeutic human monoclonal antibodies. J Immunol Methods 231, 11-23.
25. Groves, M. A. and Osbourn, J. K. (2005). Applications of ribosome display to antibody drug discovery. Expert. Opin Biol Ther. 5, 125-135.
26. Hinton, P. R., Johlfs, M. G., Xiong, J. M., Hanestad, K., Ong, K. C., Bullock, C., Keller, S., Tang, M. T., Tso, J. Y., Vasquez, M., and Tsurushita, N. (2004). Engineered human IgG antibodies with longer serum half-lives in primates. J Biol Chem 279, 6213-6216.
27. Hinton, P. R., Xiong, J. M., Johlfs, M. G., Tang, M. T., Keller, S., and Tsurushita, N. (2006). An engineered human IgG1 antibody with longer serum half-life. J Immunol 176, 346-356.
28. Holliger, P. and Hudson, P. J. (2005). Engineered antibody fragments and the rise of single domains. Nat Biotechnol. 23, 1126-1136.
29. Hoogenboom, H. R. (2002). Overview of antibody phage-display technology and its applications. Methods Mol Biol 178, 1-37.
30. Hwang, W. Y., Almagro, J. C., Buss, T. N., Tan, P., and Foote, J. (2005a). Use of human germline genes in a CDR homology-based approach to antibody humanization. Methods 36, 35-42.
31. Hwang, W. Y., Almagro, J. C., Buss, T. N., Tan, P., and Foote, J. (2005b). Use of human germline genes in a CDR homology-based approach to antibody humanization. Methods 36, 35-42.
32. Imhof, B. A. and Aurrand-Lions, M. Vascular adhesion molecules and modulation of their function. WO 00/53749. 14-9-2000.
33. Imhof, B. A. and Aurrand-Lions, M. Angiogenesis inhibiting molecules and their use in the treatment and diagnosis of cancer. WO 2005/050213. 2-6-2005.
34. Johnson-Leger, C. A., Aurrand-Lions, M., Beltraminelli, N., Fasel, N., and Imhof, B. A. (2002a). Junctional adhesion molecule-2 (JAM-2) promotes lymphocyte transendothelial migration. Blood 100, 2479-2486.
35. Johnson-Leger, C. A., Aurrand-Lions, M., Beltraminelli, N., Fasel, N., and Imhof, B. A. (2002b). Junctional adhesion molecule-2 (JAM-2) promotes lymphocyte transendothelial migration. Blood 100, 2479-2486.
36. Kabat, E. A. (1988). Antibody complementarity and antibody structure. J Immunol 141, S25-S36.
37. Kamei, D. T., Lao, B. J., Ricci, M. S., Deshpande, R., Xu, H., Tidor, B., and Lauffenburger, D. A. (2005). Quantitative methods for developing Fc mutants with extended half-lives. Biotechnol. Bioeng. 92, 748-760.
38. Kashmiri, S. V., De Pascalis, R., Gonzales, N. R., and Schlom, J. (2005). SDR grafting—a new approach to antibody humanization. Methods 36, 25-34.
39. Kellermann, S. A. and Green, L. L. (2002). Antibody discovery: the use of transgenic mice to generate human monoclonal antibodies for therapeutics. Curr Opin Biotechnol. 13, 593-597.
40. Kim, J. K., Firan, M., Radu, C. G., Kim, C. H., Ghetie, V., and Ward, E. S. (1999). Mapping the site on human IgG for binding of the MHC class I-related receptor, FcRn. Eur J Immunol 29, 2819-2825.
41. Kontermann, R. E. (2006). Immunoliposomes for cancer therapy. Curr Opin Mol Ther. 8, 39-45.
42. Kretzschmar, T. and von Ruden, T. (2002). Antibody discovery: phage display. Curr Opin Biotechnol. 13, 598-602.
43. Lai, R., Dang, C. T., Malkin, M. G., and Abrey, L. E. (2004). The risk of central nervous system metastases after trastuzumab therapy in patients with breast carcinoma. Cancer 101, 810-816.
44. Lamagna, C., Hodivala-Dilke, K. M., Imhof, B. A., and Aurrand-Lions, M. (2005a). Antibody against junctional adhesion molecule-C inhibits angiogenesis and tumor growth. Cancer Res 65, 5703-5710.
45. Lamagna, C., Meda, P., Mandicourt, G., Brown, J., Gilbert, R. J., Jones, E. Y., Kiefer, F., Ruga, P., Imhof, B. A., and Aurrand-Lions, M. (2005b). Dual interaction of JAM-C with JAM-B and alpha(M)beta2 integrin: function in junctional complexes and leukocyte adhesion. Mol Biol Cell 16, 4992-5003.
46. Lamszus, K., Brockmann, M. A., Eckerich, C., Bohlen, P., May, C., Mangold, U., Fillbrandt, R., and Westphal, M. (2005). Inhibition of glioblastoma angiogenesis and invasion by combined treatments directed against vascular endothelial growth factor receptor-2, epidermal growth factor receptor, and vascular endothelial-cadherin. Clin Cancer Res 11, 4934-4940.
47. Lamszus, K., Kunkel, P., and Westphal, M. (2003). Invasion as limitation to anti-angiogenic glioma therapy. Acta Neurochir. Suppl 88, 169-177.
48. Lazar, G. A., Desjarlais, J. R., Jacinto, J., Karki, S., and Hammond, P. W. (2007). A molecular immunology approach to antibody humanization and functional optimization. Mol Immunol 44, 1986-1998.
49. Li, J., Sai, T., Berger, M., Chao, Q., Davidson, D., Deshmukh, G., Drozdowski, B., Ebel, W., Harley, S., Henry, M., Jacob, S., Kline, B., Lazo, E., Rotella, F., Routhier, E., Rudolph, K., Sage, J., Simon, P., Yao, J., Zhou, Y., Kavuru, M., Bonfield, T., Thomassen, M. J., Sass, P. M., Nicolaides, N. C., and Grasso, L. (2006). Human antibodies for immunotherapy development generated via a human B cell hybridoma technology. Proc Natl Acad Sci USA 103, 3557-3562.
50. Lo, B. K. (2004). Antibody humanization by CDR grafting. Methods Mol Biol 248, 135-159.
51. Lonberg, N. (2005). Human antibodies from transgenic animals. Nat Biotechnol. 23, 1117-1125.
52. Low, S. C., Nunes, S. L., Bitonti, A. J., and Dumont, J. A. (2005). Oral and pulmonary delivery of FSH-Fc fusion proteins via neonatal Fc receptor-mediated transcytosis. Hum. Reprod. 20, 1805-1813.
53. MacDonald, T. J., Taga, T., Shimada, H., Tabrizi, P., Zlokovic, B. V., Cheresh, D. A., and Laug, W. E. (2001). Preferential susceptibility of brain tumors to the antiangiogenic effects of an alpha(v) integrin antagonist. Neurosurgery 48, 151-157.
54. Mandell, K. J. and Parkos, C. A. (2005). The JAM family of proteins. Adv. Drug Deliv. Rev 57, 857-867.
55. Mather, J. P. and Roberts, P. E. JAM-3 and antibodies that bind thereto. Raven Biotechnologies, Inc. WO 20061084078. 10-8-2006.
56. Mirza, M., Hreinsson, J., Strand, M. L., Hovatta, O., Soder, O., Philipson, L., Pettersson, R. F., and Sollerbrant, K. (2006). Coxsackievirus and adenovirus receptor (CAR)

is expressed in male germ cells and forms a complex with the differentiation factor JAM-C in mouse testis. Exp Cell Res 312, 817-830.
57. Mosavi, L. K., Cammett, T. J., Desrosiers, D. C., and Peng, Z. Y. (2004). The ankyrin repeat as molecular architecture for protein recognition. Protein Sci 13, 1435-1448.
58. Muller, W. A. (2003). Leukocyte-endothelial-cell interactions in leukocyte transmigration and the inflammatory response. Trends Immunol 24, 327-334.
59. Nicholson, I. C., Zou, X., Popov, A. V., Cook, G. P., Corps, E. M., Humphries, S., Ayling, C., Goyenechea, B., Xian, J., Taussig, M. J., Neuberger, M. S., and Bruggemann, M. (1999). Antibody repertoires of four-and five-feature translocus mice carrying human immunoglobulin heavy chain and kappa and lambda light chain yeast artificial chromosomes. J Immunol 163, 6898-6906.
60. Nilsson, F. Y. and Tolmachev, V. (2007). Affibody molecules: new protein domains for molecular imaging and targeted tumor therapy. Curr Opin Drug Discov. Devel. 10, 167-175.
61. Nishibori, N., Horiuchi, H., Furusawa, S., and Matsuda, H. (2006). Humanization of chicken monoclonal antibody using phage-display system. Mol Immunol 43, 634-642.
62. O'Brien, S, and Jones, T. (2003). Humanization of monoclonal antibodies by CDR grafting. Methods Mol Biol 207, 81-100.
63. Palmeri, D., van Zante, A., Huang, C. C., Hemmerich, S., and Rosen, S. D. (2000). Vascular endothelial junction-associated molecule, a novel member of the immunoglobulin superfamily, is localized to intercellular boundaries of endothelial cells. J Biol Chem 275, 19139-19145.
64. Pardridge, W. M. (2006). Molecular Trojan horses for blood-brain barrier drug delivery. Curr Opin Pharmacol 6, 494-500.
65. Sampson, J. H., Crotty, L. E., Lee, S., Archer, G. E., Ashley, D. M., Wikstrand, C. J., Hale, L. P., Small, C., Dranoff, G., Friedman, A. H., Friedman, H. S., and Bigner, D. D. (2000). Unarmed, tumor-specific monoclonal antibody effectively treats brain tumors. Proc Natl Acad Sci USA 97, 7503-7508.
66. Santoso, S., Sachs, U. J., Kroll, H., Linder, M., Ruf, A., Preissner, K. T., and Chavakis, T. (2002). The junctional adhesion molecule 3 (JAM-3) on human platelets is a counterreceptor for the leukocyte integrin Mac-1. J Exp Med 196, 679-691.
67. Shields, R. L., Namenuk, A. K., Hong, K., Meng, Y. G., Rae, J., Briggs, J., Xie, D., Lai, J., Stadlen, A., Li, B., Fox, J. A., and Presta, L. G. (2001). High resolution mapping of the binding site on human IgG1 for Fc gamma RI, Fc gamma RII, Fc gamma RIII, and FcRn and design of IgG1 variants with improved binding to the Fc gamma R. J Biol Chem 276, 6591-6604.
68. Sillerud, L. O. and Larson, R. S. (2005). Design and structure of peptide and peptidomimetic antagonists of protein-protein interaction. Curr Protein Pept. Sci 6, 151-169.
69. Takenaka, N., Mikoshiba, K., Takamatsu, K., Tsukada, Y., Ohtani, M., and Toya, S. (1985). Immunohistochemical detection of the gene product of Rous sarcoma virus in human brain tumors. Brain Res 337, 201-207.
70. Tomlinson, I. M. (2004). Next-generation protein drugs. Nat Biotechnol. 22, 521-522.
71. Tsurushita, N., Hinton, P. R., and Kumar, S. (2005). Design of humanized antibodies: from anti-Tac to Zenapax. Methods 36, 69-83.
72. Tuettenberg, J., Friedel, C., and Vajkoczy, P. (2006). Angiogenesis in malignant glioma—a target for antitumor therapy? Crit Rev Oncol Hematol 59, 181-193.
73. Vaughn, D. E., Milburn, C. M., Penny, D. M., Martin, W. L., Johnson, J. L., and Bjorkman, P. J. (1997). Identification of critical IgG binding epitopes on the neonatal Fc receptor. J Mol Biol 274, 597-607.
74. Walker, P. R., Calzascia, T., Schnuriger, V., Scamuffa, N., Saas, P., de Tribolet, N., and Dietrich, P. Y. (2000). The brain parenchyma is permissive for full antitumor CTL effector function, even in the absence of CD4 T cells. J Immunol 165, 3128-3135.
75. Ward, E. S. and Ghetie, V. (1995). The effector functions of immunoglobulins: implications for therapy. Ther. Immunol 2, 77-94.
76. Winter, G., Griffiths, A. D., Hawkins, R. E., and Hoogenboom, H. R. (1994). Making antibodies by phage display technology. Annu Rev Immunol 12, 433-455.
77. Zen, K., Babbin, B. A., Liu, Y., Whelan, J. B., Nusrat, A., and Parkos, C. A. (2004). JAM-C is a component of desmosomes and a ligand for CD11b/CD18-mediated neutrophil transepithelial migration. Mol Biol Cell 15, 3926-3937.

The invention claimed is:

1. A method for treating a patient with glioma comprising administering to the patient an effective amount of an antibody or antigen binding fragment thereof that specifically binds to JAM-C.

2. The method according to claim 1, wherein the antibody or antigen binding fragment thereof that specifically binds to JAM-C inhibits the growth of glioma.

3. The method according to claim 1, wherein the antibody or antigen binding fragment thereof that specifically binds to JAM-C has a dissociation constant $k_d$ of $\geq 10^{-2}$ s$^{-1}$ as determined by surface plasmon resonance using solid phase bound JAM-C and the corresponding antibody binding thereto as analyte.

4. The method according to claim 1, wherein the antibody or antigen binding fragment thereof is linked to another agent selected from: a cytotoxic agent, a radionuclide, a cytokine, a therapeutic agent, an imaging agent or polyethylene glycol (PEG).

5. The method according to claim 1, wherein the glioma is an astrocytoma.

6. The method according to claim 5, wherein the astrocytoma is grade I, grade II or grade III.

7. The method according to claim 5, wherein the astrocytoma is a glioblastoma.

8. The method according to claim 1, wherein the glioma has metastasized.

9. The method according to claim 1, wherein the antibody that specifically binds to JAM-C is selected from:
 (a) the antibody D33, which is produced by the hybridoma cell line that has been deposited at the European Collection of Cell Cultures (ECACC) under accession no. 06092701;
 (b) an antibody comprising the antigen binding region of the antibody according to (a); or
 (c) a humanized or primatized antibody of the antibody according to (a).

10. A method for treating metastasis of a glioma in a patient comprising administering to the patient an effective amount of an antibody or antigen binding fragment thereof that specifically binds to JAM-C and inhibits metastasis of a glioma in said patient.

11. The method according to claim 10, wherein the antibody or antigen binding fragment thereof that specifically binds to JAM-C inhibits the growth of glioma.

12. The method according to claim 10, wherein the antibody or antigen binding fragment thereof that specifically binds to JAM-C has a dissociation constant $k_d$ of $\geq 10^{-2}$ s$^{-1}$ as determined by surface plasmon resonance using solid phase bound JAM-C and the corresponding antibody binding thereto as analyte.

13. The method according to claim 10, wherein the antibody or antigen binding fragment thereof is linked to another agent selected from: a cytotoxic agent, a radionuclide, a cytokine, a therapeutic agent, an imaging agent or a polyethylene glycol (PEG).

14. The method according to claim 10, wherein the glioma is an astrocytoma.

15. The method according to claim 14, wherein the astrocytoma is grade I, grade II or grade III.

16. The method according to claim 14, wherein the astrocytoma is a glioblastoma.

17. The method according to claim 10, wherein the antibody that specifically binds to JAM-C is selected from:
 (a) the antibody D33, which is produced by the hybridoma cell line that has been deposited at the European Collection of Cell Cultures (ECACC) under accession no. 06092701;
 (b) an antibody comprising the antigen binding region of the antibody according to (a); or
 (c) a humanized or primatized antibody of the antibody according to (a).

* * * * *

UNITED STATES PATENT AND TRADEMARK OFFICE
CERTIFICATE OF CORRECTION

PATENT NO. : 8,007,797 B2  
APPLICATION NO. : 12/443231  
DATED : August 30, 2011  
INVENTOR(S) : Pierre-Yves Dietrich et al.

Page 1 of 2

It is certified that error appears in the above-identified patent and that said Letters Patent is hereby corrected as shown below:

Column 27,  
Line 61, "17-MG" should read --17-AAG--.

Column 40,  
Line 55, "10 mM 5 glycine" should read --10 mM glycine--.

Column 50,  
Line 43, "CTG GGG MG ACA TCC CTG MG" should read  
    --CTG GGG AAG ACA TCC CTG AAG--.  
Line 50, "CTA GM GCA" should read --CTA GAA GCA--.  
Line 55, "CAC ARC AGT" should read --CAC AGC AGT--.

Column 52,  
Line 65, "106" should read --$10^6$--.

Column 54,  
Lines 31-33, "AGC TTA AAA AGC CAA ACC ACA TAT GTG TAT CTC TTG MT  
    ACA CAT ATG TGG TTT GGC GGG" should read  
    --AGC TTA AAA AGC CAA ACC ACA TAT GTG TAT CTC TTG  
    AAT ACA CAT ATG TGG TTT GGC GGG--.

Column 54,  
Lines 42-44, "CAA GTG ACC CTA GGA TTG MT GGA AGA AAA TCC MG ATG  
    GCC AAA CM CGT ATG TGT" should read  
    --CAA GTG ACC CTA GGA TTG AAT GGA AGA AAA TCC AAG  
    ATG GCC AAA CAA CGT ATG TGT--.

Signed and Sealed this  
Thirteenth Day of March, 2012

David J. Kappos  
*Director of the United States Patent and Trademark Office*

CERTIFICATE OF CORRECTION (continued)
U.S. Pat. No. 8,007,797 B2

Column 56,
Line 32, "ACG GTG GAG CAT GM AGC" should read
--ACG GTG GAG CAT GAA AGC--.
Line 38, "TGT GM GTC TGC AGG GAG TTT" should read
--TGT GAA GTC TGC AGG GAG TTT--.
Lines 40-41, "GTG TCA GM ACA TCG CGT ACA" should read
--GTG TCA GAA ACA TCG CGT ACA--.
Lines 41-42, "GCC ATC GM GTG AAT GCA G" should read
--GCC ATC GAA GTG AAT GCA G--.
Lines 43-44, "TCA MT TGT TCT GTA TCG TCA CTG" should read
--TCA AAT TGT TCT GTA TCG TCA CTG--.
Lines 46-47, "GCC MT TCC TCC ACA TCA AG" should read
--GCC AAT TCC TCC ACA TCA AG--.
Line 48, "GCA GTG CGG CM CCA GAT" should read
--GCA GTG CGG CAA CCA GAT--.
Lines 48-49, "AGT GGG ATC MT GCC ATG CT" should read
--AGT GGG ATC AAT GCC ATG CT--.

SEQUENCE LISTING

```
<160> NUMBER OF SEQ ID NOS: 37

<210> SEQ ID NO 1
<211> LENGTH: 21
<212> TYPE: DNA
<213> ORGANISM: Artificial
<220> FEATURE:
<223> OTHER INFORMATION: human JAM-C primer forward

<400> SEQUENCE: 1
ctggggaaga catccctgaa g                                                 21

<210> SEQ ID NO 2
<211> LENGTH: 21
<212> TYPE: DNA
<213> ORGANISM: Artificial
<220> FEATURE:
<223> OTHER INFORMATION: human JAM-C primer reverse
```

```
<400> SEQUENCE: 2
agtgcggatg tagttaactc c                                          21

<210> SEQ ID NO 3
<211> LENGTH: 22
<212> TYPE: DNA
<213> ORGANISM: Artificial
<220> FEATURE:
<223> OTHER INFORMATION: human JAM-B primer forward

<400> SEQUENCE: 3
agtagtcaca gcagtagagt ac                                         22

<210> SEQ ID NO 4
<211> LENGTH: 24
<212> TYPE: DNA
<213> ORGANISM: Artificial
<220> FEATURE:
<223> OTHER INFORMATION: human JAM-B primer reverse

<400> SEQUENCE: 4
acttatgttg agatcatcta cttg                                       24

<210> SEQ ID NO 5
<211> LENGTH: 30
<212> TYPE: DNA
<213> ORGANISM: Artificial
<220> FEATURE:
<223> OTHER INFORMATION: human alpha-actin primer forward

<400> SEQUENCE: 5
tgacggggtc acccacactg tgcccatcta                                 30

<210> SEQ ID NO 6
<211> LENGTH: 30
<212> TYPE: DNA
<213> ORGANISM: Artificial
<220> FEATURE:
<223> OTHER INFORMATION: human alpha-actin primer reverse

<400> SEQUENCE: 6
ctagaagcat ttgcggtgga cgatggaggg                                 30

<210> SEQ ID NO 7
<211> LENGTH: 60
<212> TYPE: DNA
<213> ORGANISM: Artificial
<220> FEATURE:
<223> OTHER INFORMATION: mouse JAM-C RNAi primer forward

<400> SEQUENCE: 7
gatccccgcc aaaccacata tgtgtattca agagatacac atatgtggtt tggcttttta  60

<210> SEQ ID NO 8
<211> LENGTH: 60
<212> TYPE: DNA
<213> ORGANISM: Artificial
<220> FEATURE:
<223> OTHER INFORMATION: mouse JAM-C RNAi primer reverse

<400> SEQUENCE: 8
agcttaaaaa gccaaaccac atatgtgtat ctcttgaata cacatatgtg gtttggcggg  60

<210> SEQ ID NO 9
<211> LENGTH: 57
```

```
<212> TYPE: DNA
<213> ORGANISM: Artificial
<220> FEATURE:
<223> OTHER INFORMATION: mouse JAM-C RNAi mutation primer forward

<400> SEQUENCE: 9
caagtgaccc taggattgaa tggaagaaaa tccaagatgg ccaaacaacg tatgtgt        57

<210> SEQ ID NO 10
<211> LENGTH: 30
<212> TYPE: DNA
<213> ORGANISM: Artificial
<220> FEATURE:
<223> OTHER INFORMATION: mouse JAM-C RNAi mutation primer reverse

<400> SEQUENCE: 10
cctcactcgt ccggatgtag ttaacaccgt                                      30

<210> SEQ ID NO 11
<211> LENGTH: 39
<212> TYPE: DNA
<213> ORGANISM: Artificial
<220> FEATURE:
<223> OTHER INFORMATION: T7 RNA polymerase promoter sequence

<400> SEQUENCE: 11
ggccagtgaa ttgtaatacg actcactata gggaggcgg                            39

<210> SEQ ID NO 12
<211> LENGTH: 20
<212> TYPE: DNA
<213> ORGANISM: Artificial
<220> FEATURE:
<223> OTHER INFORMATION: mouse JAM-C primer forward

<400> SEQUENCE: 12
gaactcggag acaggcactc                                                 20

<210> SEQ ID NO 13
<211> LENGTH: 20
<212> TYPE: DNA
<213> ORGANISM: Artificial
<220> FEATURE:
<223> OTHER INFORMATION: mouse JAM-C primer reverse

<400> SEQUENCE: 13
tactgcccag agtcgtcctt                                                 20

<210> SEQ ID NO 14
<211> LENGTH: 20
<212> TYPE: DNA
<213> ORGANISM: Artificial
<220> FEATURE:
<223> OTHER INFORMATION: mouse c-Fos primer forward

<400> SEQUENCE: 14
gaatggtgaa gaccgtgtca                                                 20

<210> SEQ ID NO 15
<211> LENGTH: 23
<212> TYPE: DNA
<213> ORGANISM: Artificial
<220> FEATURE:
<223> OTHER INFORMATION: mouse c-Fos primer reverse

<400> SEQUENCE: 15
tcttcctctt caggagatag ctg                                             23
```

<210> SEQ ID NO 16
<211> LENGTH: 19
<212> TYPE: DNA
<213> ORGANISM: Artificial
<220> FEATURE:
<223> OTHER INFORMATION: mouse FosL2 pimer forward

<400> SEQUENCE: 16
acgccgagtc ctactccag                                                19

<210> SEQ ID NO 17
<211> LENGTH: 20
<212> TYPE: DNA
<213> ORGANISM: Artificial
<220> FEATURE:
<223> OTHER INFORMATION: mouse FosL2 pimer reverse

<400> SEQUENCE: 17
caggcatatc tacccggaac                                               20

<210> SEQ ID NO 18
<211> LENGTH: 23
<212> TYPE: DNA
<213> ORGANISM: Artificial
<220> FEATURE:
<223> OTHER INFORMATION: mouse PAK3 primer forward

<400> SEQUENCE: 18
ccaaatggga actacttgaa cag                                           23

<210> SEQ ID NO 19
<211> LENGTH: 23
<212> TYPE: DNA
<213> ORGANISM: Artificial
<220> FEATURE:
<223> OTHER INFORMATION: mouse PAK3 primer reverse

<400> SEQUENCE: 19
ccaaatggga actacttgaa cag                                           23

<210> SEQ ID NO 20
<211> LENGTH: 18
<212> TYPE: DNA
<213> ORGANISM: Artificial
<220> FEATURE:
<223> OTHER INFORMATION: mouse PVR primer forward

<400> SEQUENCE: 20
acggtggagc atgaaagc                                                 18

<210> SEQ ID NO 21
<211> LENGTH: 20
<212> TYPE: DNA
<213> ORGANISM: Artificial
<220> FEATURE:
<223> OTHER INFORMATION: mouse PVR primer reverse

<400> SEQUENCE: 21
ggacacgttt tcaggtggat                                               20

<210> SEQ ID NO 22
<211> LENGTH: 20
<212> TYPE: DNA
<213> ORGANISM: Artificial
<220> FEATURE:
<223> OTHER INFORMATION: mouse BDNF primer forward

```
<400> SEQUENCE: 22
agtctccagg acagcaaagc                                              20

<210> SEQ ID NO 23
<211> LENGTH: 21
<212> TYPE: DNA
<213> ORGANISM: Artificial
<220> FEATURE:
<223> OTHER INFORMATION: mouse BDNF primer reverse

<400> SEQUENCE: 23
aaggatggtc atcactcttc t                                            21

<210> SEQ ID NO 24
<211> LENGTH: 20
<212> TYPE: DNA
<213> ORGANISM: Artificial
<220> FEATURE:
<223> OTHER INFORMATION: mouse RAPGEF2 primer forward

<400> SEQUENCE: 24
tttccttgtg cgttgctatg                                              20

<210> SEQ ID NO 25
<211> LENGTH: 21
<212> TYPE: DNA
<213> ORGANISM: Artificial
<220> FEATURE:
<223> OTHER INFORMATION: mouse RAPGEF2 primer reverse

<400> SEQUENCE: 25
tgtgaagtct gcagggagtt t                                            21

<210> SEQ ID NO 26
<211> LENGTH: 20
<212> TYPE: DNA
<213> ORGANISM: Artificial
<220> FEATURE:
<223> OTHER INFORMATION: mouse Tspan6 primer forward

<400> SEQUENCE: 26
ggttgtttcg ctacctgtcg                                              20

<210> SEQ ID NO 27
<211> LENGTH: 21
<212> TYPE: DNA
<213> ORGANISM: Artificial
<220> FEATURE:
<223> OTHER INFORMATION: mouse Tspan6 primer reverse

<400> SEQUENCE: 27
gtgtcagaaa catcgcgtac a                                            21

<210> SEQ ID NO 28
<211> LENGTH: 19
<212> TYPE: DNA
<213> ORGANISM: Artificial
<220> FEATURE:
<223> OTHER INFORMATION: mouse AFAP primer forward

<400> SEQUENCE: 28
gccatcgaag tgaatgcag                                               19

<210> SEQ ID NO 29
<211> LENGTH: 21
```

```
<212> TYPE: DNA
<213> ORGANISM: Artificial
<220> FEATURE:
<223> OTHER INFORMATION: mouse AFAP primer reverse

<400> SEQUENCE: 29
cagcctcttc aacttgtcct c                                              21

<210> SEQ ID NO 30
<211> LENGTH: 24
<212> TYPE: DNA
<213> ORGANISM: Artificial
<220> FEATURE:
<223> OTHER INFORMATION: mouse Ptgfrn primer forward

<400> SEQUENCE: 30
tcaaattgtt ctgtatcgtc actg                                           24

<210> SEQ ID NO 31
<211> LENGTH: 20
<212> TYPE: DNA
<213> ORGANISM: Artificial
<220> FEATURE:
<223> OTHER INFORMATION: mouse Ptgfrn primer reverse

<400> SEQUENCE: 31
acatcgaagg ccatgtcatc                                                20

<210> SEQ ID NO 32
<211> LENGTH: 19
<212> TYPE: DNA
<213> ORGANISM: Artificial
<220> FEATURE:
<223> OTHER INFORMATION: mouse VLDLR primer forward

<400> SEQUENCE: 32
gggccatcct tcctctctt                                                 19

<210> SEQ ID NO 33
<211> LENGTH: 20
<212> TYPE: DNA
<213> ORGANISM: Artificial
<220> FEATURE:
<223> OTHER INFORMATION: mouse VLDLR primer reverse

<400> SEQUENCE: 33
gccaattcct ccacatcaag                                                20

<210> SEQ ID NO 34
<211> LENGTH: 18
<212> TYPE: DNA
<213> ORGANISM: Artificial
<220> FEATURE:
<223> OTHER INFORMATION: mouse Tubulin 2 primer forward

<400> SEQUENCE: 34
gcagtgcggc aaccagat                                                  18

<210> SEQ ID NO 35
<211> LENGTH: 20
<212> TYPE: DNA
<213> ORGANISM: Artificial
<220> FEATURE:
<223> OTHER INFORMATION: mouse Tubulin 2 primer reverse

<400> SEQUENCE: 35
agtgggatca atgccatgct                                                20
```

```
<210> SEQ ID NO 36
<211> LENGTH: 21
<212> TYPE: DNA
<213> ORGANISM: Artificial
<220> FEATURE:
<223> OTHER INFORMATION: mouse GAPDH primer forward

<400> SEQUENCE: 36
tccatgacaa ctttggcatt g                                             21

<210> SEQ ID NO 37
<211> LENGTH: 21
<212> TYPE: DNA
<213> ORGANISM: Artificial
<220> FEATURE:
<223> OTHER INFORMATION: mouse GAPDH primer reverse

<400> SEQUENCE: 37
cagtcttctg ggtggcagtg a                                             21
```